(12) United States Patent
Marshall et al.

(10) Patent No.: US 7,918,868 B2
(45) Date of Patent: Apr. 5, 2011

(54) METHOD AND APPARATUS FOR MENISCAL REPAIR

(75) Inventors: Peter Marshall, Bolton, MA (US); Dennis Hubbard, Lancaster, MA (US)

(73) Assignee: Scandius Biomendical, Inc., New Haven, CT (US)

( * ) Notice: Subject to any disclaimer, the term of this patent is extended or adjusted under 35 U.S.C. 154(b) by 792 days.

(21) Appl. No.: 11/805,223

(22) Filed: May 22, 2007

(65) Prior Publication Data

US 2008/0091219 A1 Apr. 17, 2008

Related U.S. Application Data

(60) Provisional application No. 60/802,378, filed on May 22, 2006, provisional application No. 60/921,403, filed on Apr. 2, 2007.

(51) Int. Cl.
*A61B 17/10* (2006.01)
*A61B 17/04* (2006.01)
*A61B 17/12* (2006.01)

(52) U.S. Cl. .................................. 606/144; 606/139

(58) Field of Classification Search ............ 606/139, 606/144, 145, 148
See application file for complete search history.

(56) References Cited

U.S. PATENT DOCUMENTS

| | | | |
|---|---|---|---|
| 659,422 A * | 10/1900 | Shidler | 606/144 |
| 1,855,546 A * | 4/1932 | File | 606/139 |
| 2,012,776 A | 8/1935 | Roeder | |
| 2,880,728 A | 4/1959 | Rights | |
| 4,493,323 A | 1/1985 | Albright et al. | |
| 4,836,205 A | 6/1989 | Barrett | |
| 4,935,027 A | 6/1990 | Yoon | |
| 4,994,074 A | 2/1991 | Bezwada et al. | |
| 5,037,433 A | 8/1991 | Wilk et al. | |
| 5,085,661 A | 2/1992 | Moss | |
| 5,123,914 A | 6/1992 | Cope | |
| 5,250,055 A * | 10/1993 | Moore et al. | 606/148 |
| 5,281,237 A | 1/1994 | Gimpelson | |
| 5,330,488 A * | 7/1994 | Goldrath | 606/148 |
| 5,336,231 A | 8/1994 | Adair | |
| 5,364,410 A | 11/1994 | Failla et al. | |
| 5,391,182 A | 2/1995 | Chin | |
| 5,423,844 A * | 6/1995 | Miller | 606/171 |
| 5,458,609 A | 10/1995 | Gordon et al. | |
| 5,462,560 A | 10/1995 | Stevens | |

(Continued)

FOREIGN PATENT DOCUMENTS

DE 2900265 7/1980

(Continued)

OTHER PUBLICATIONS

International Search Report for corresponding PCT/US07/12163, date of mailing is Jul. 30, 2008 (1 pg).

*Primary Examiner* — (Jackie) Tan-Uyen T Ho
*Assistant Examiner* — Dianne Dornbusch

(57) ABSTRACT

An apparatus for suturing tissue includes first and second needles. A first structure associated with the first needle is adapted and configured to pass a leading portion of the suture from a near side of a tissue to a far side of the tissue. A second structure cooperates with the second needle to capture and secure the suture. Proximal movement of the apparatus after the suture is captured moves the suture from the far side of the tissue to the near side of the tissue.

13 Claims, 76 Drawing Sheets

U.S. PATENT DOCUMENTS

| | | | |
|---|---|---|---|
| 5,499,991 A * | 3/1996 | Garman et al. | 606/148 |
| 5,501,691 A * | 3/1996 | Goldrath | 606/148 |
| 5,531,699 A | 7/1996 | Tomba et al. | |
| 5,544,664 A | 8/1996 | Benderev et al. | |
| 5,562,684 A | 10/1996 | Kammerer | |
| 5,569,269 A | 10/1996 | Hart et al. | |
| 5,573,542 A | 11/1996 | Stevens | |
| 5,601,571 A | 2/1997 | Moss | |
| 5,611,515 A | 3/1997 | Benderev et al. | |
| 5,620,012 A | 4/1997 | Benderev et al. | |
| 5,653,716 A | 8/1997 | Malo | |
| 5,665,096 A | 9/1997 | Yoon | |
| 5,681,333 A | 10/1997 | Burkhart | |
| 5,722,981 A | 3/1998 | Stevens | |
| 5,741,278 A | 4/1998 | Stevens | |
| 5,749,884 A | 5/1998 | Benderev et al. | |
| 5,776,150 A | 7/1998 | Nolan et al. | |
| 5,782,845 A * | 7/1998 | Shewchuk | 606/144 |
| 5,817,112 A * | 10/1998 | Christoudias | 606/148 |
| RE36,020 E * | 12/1998 | Moore et al. | 606/144 |
| 5,842,478 A | 12/1998 | Benderev et al. | |
| 5,895,395 A * | 4/1999 | Yeung | 606/144 |
| 5,897,563 A | 4/1999 | Yoon | |
| 5,921,993 A | 7/1999 | Yoon | |
| 5,938,668 A * | 8/1999 | Scirica et al. | 606/145 |
| 5,941,439 A | 8/1999 | Kammerer et al. | |
| 5,954,732 A | 9/1999 | Hart et al. | |
| 6,022,360 A | 2/2000 | Reimels | |
| 6,045,571 A | 4/2000 | Hill et al. | |
| 6,047,826 A | 4/2000 | Kalinski et al. | |
| 6,059,800 A | 5/2000 | Hart et al. | |
| 6,066,146 A | 5/2000 | Carroll et al. | |
| 6,071,289 A | 6/2000 | Stefanchik et al. | |
| 6,110,183 A | 8/2000 | Cope | |
| 6,113,610 A | 9/2000 | Poncet | |
| RE36,974 E | 11/2000 | Bonutti | |
| 6,171,317 B1 * | 1/2001 | Jackson et al. | 606/148 |
| 6,206,895 B1 | 3/2001 | Levinson | |
| 6,293,961 B2 | 9/2001 | Schwartz et al. | |
| 6,306,159 B1 | 10/2001 | Schwartz et al. | |
| 6,319,271 B1 | 11/2001 | Schwartz et al. | |
| 6,443,963 B1 | 9/2002 | Baldwin et al. | |
| 6,451,024 B1 | 9/2002 | Thompson et al. | |
| 6,491,707 B2 | 12/2002 | Makower et al. | |
| 6,500,184 B1 | 12/2002 | Chan et al. | |
| 6,524,317 B1 | 2/2003 | Ritchart | |
| 6,533,795 B1 | 3/2003 | Tran et al. | |
| 6,605,096 B1 | 8/2003 | Ritchart | |
| 6,638,286 B1 * | 10/2003 | Burbank et al. | 606/157 |
| 6,679,895 B1 | 1/2004 | Sancoff et al. | |
| 6,699,263 B2 | 3/2004 | Cope | |
| 6,770,084 B1 | 8/2004 | Bain et al. | |
| 6,893,448 B2 | 5/2005 | O'Quinn et al. | |
| 6,932,824 B1 | 8/2005 | Roop et al. | |
| 6,972,027 B2 | 12/2005 | Fallin et al. | |
| 6,984,237 B2 | 1/2006 | Hatch et al. | |
| 6,988,985 B2 | 1/2006 | Suzuki et al. | |
| 7,090,690 B2 | 8/2006 | Foerster et al. | |
| 7,118,583 B2 | 10/2006 | O'Quinn et al. | |
| 7,141,057 B2 * | 11/2006 | Burbank et al. | 606/148 |
| 7,147,646 B2 * | 12/2006 | Dana et al. | 606/148 |
| 7,153,312 B1 | 12/2006 | Torrie et al. | |
| 7,156,857 B2 | 1/2007 | Pasricha et al. | |
| 7,166,116 B2 | 1/2007 | Lizardi et al. | |
| 7,211,093 B2 | 5/2007 | Sauer et al. | |
| 7,232,447 B2 | 6/2007 | Gellman et al. | |
| 7,232,448 B2 | 6/2007 | Battles et al. | |
| 7,306,613 B2 | 12/2007 | Kawashima et al. | |
| 7,320,693 B2 | 1/2008 | Pollack et al. | |
| 7,390,328 B2 | 6/2008 | Modesitt | |
| 7,449,024 B2 | 11/2008 | Stafford | |
| 7,625,386 B2 * | 12/2009 | Abe et al. | 606/144 |
| 7,731,726 B2 * | 6/2010 | Belhe et al. | 606/144 |
| 2004/0039442 A1 | 2/2004 | St. Goar et al. | |
| 2004/0122473 A1 | 6/2004 | Ewers et al. | |
| 2004/0249395 A1 | 12/2004 | Mikkaichi et al. | |
| 2005/0021055 A1 * | 1/2005 | Toubia et al. | 606/144 |
| 2006/0069398 A1 | 3/2006 | Suzuki et al. | |
| 2006/0241658 A1 | 10/2006 | Cerundolo | |
| 2007/0118153 A1 | 5/2007 | Funamura et al. | |
| 2007/0179509 A1 | 8/2007 | Nagata et al. | |
| 2007/0282351 A1 | 12/2007 | Harada et al. | |
| 2007/0293876 A1 * | 12/2007 | Abe et al. | 606/144 |
| 2008/0114380 A1 | 5/2008 | Takemoto et al. | |
| 2008/0140092 A1 | 6/2008 | Stone et al. | |
| 2008/0140094 A1 | 6/2008 | Schwartz et al. | |
| 2008/0177288 A1 | 7/2008 | Carlson | |
| 2008/0228204 A1 | 9/2008 | Hamilton et al. | |
| 2008/0243147 A1 | 10/2008 | Hamilton et al. | |
| 2008/0243148 A1 | 10/2008 | Mikkaichi et al. | |
| 2008/0255591 A1 | 10/2008 | Harada et al. | |
| 2008/0269783 A1 | 10/2008 | Griffith | |

FOREIGN PATENT DOCUMENTS

| | | |
|---|---|---|
| JP | 4226643 | 8/1992 |
| JP | 05-161655 | 6/1993 |
| JP | 06-024533 B | 4/1994 |
| JP | 07-328020 | 12/1995 |
| JP | 3331215 B | 8/2003 |
| JP | 2006025932 | 2/2006 |
| JP | 2006025933 | 2/2006 |
| JP | 2006025934 | 2/2006 |
| WO | WO 95/22932 | 8/1995 |
| WO | WO 2004/006782 | 1/2004 |
| WO | WO 2006/037639 | 4/2006 |
| WO | WO 2006/082810 | 8/2006 |

* cited by examiner

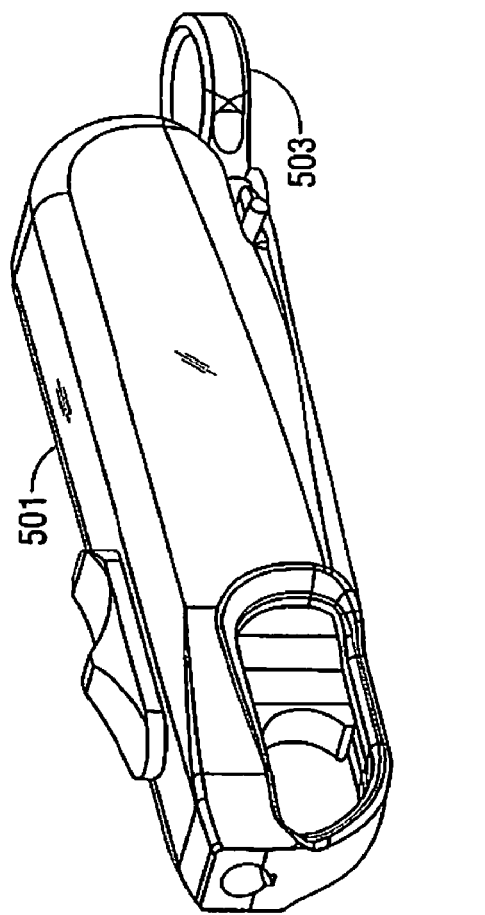
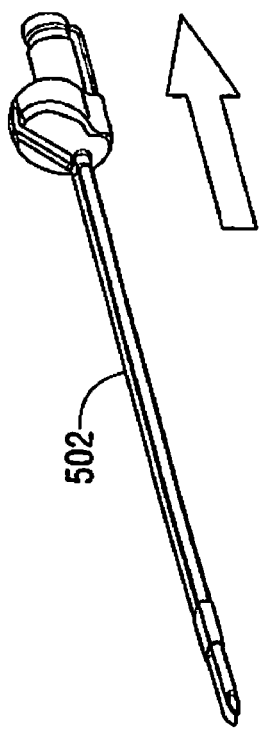
FIG. 98

METHOD AND APPARATUS FOR MENISCAL REPAIR

REFERENCE TO PENDING PRIOR PATENT APPLICATIONS

This patent application claims benefit of:

(i) pending prior U.S. Provisional Patent Application Ser. No. 60/802,378, filed May 22, 2006 by Peter Marshall et al. for METHOD AND APPARATUS FOR MENISCAL REPAIR; and (ii) pending prior U.S. Provisional Patent Application Ser. No. 60/921,403, filed Apr. 2, 2007 by Peter Marshall et al. for METHOD AND APPARATUS FOR MENISCAL REPAIR.

The two above-identified patent applications are hereby incorporated herein by reference.

FIELD OF THE INVENTION

This invention relates to surgical methods and apparatus in general, and more particularly to surgical methods and apparatus for the repair of the meniscus.

BACKGROUND OF THE INVENTION

Looking first at FIGS. 1 and 2, the meniscus 5 is a piece of cartilage located in the knee joint, between the top of the tibia 10 and the bottom of the femur 15. Meniscus 5 serves to facilitate stable movement of the tibia and femur relative to one another, and to absorb shock and to spread load.

Meniscus 5 is frequently damaged (e.g., torn) as the result of injury and/or accident. See, for example, the tear 20 shown in FIG. 3. A damaged meniscus can impede proper motion of the knee joint and cause pain, among other things.

At one time, the standard treatment for a badly damaged meniscus was the partial or complete removal of the meniscus. However, it was subsequently recognized that patients having a partial or complete removal of their meniscus frequently suffered from long term joint problems, e.g., arthritis.

The current trend is toward repairing a damaged meniscus, rather than removing part or all of the meniscus. This approach typically requires that tears in the meniscus be closed. There are currently two approaches to closing a tear in the meniscus: suturing and fastening.

Suturing a tear in the meniscus has heretofore been technically difficult. This is because the knee joint is a relatively tight space and has limited access points, thus making it hard to maneuver suturing instruments and visualization devices. In addition, there are delicate blood vessels and nerves adjacent to the knee joint (e.g., at the back of the knee) which can be easily damaged, particularly by the sharp needles used to place the suture.

Due to the technical difficulties of suturing, fasteners have been developed to close a meniscal tear. Many different types of meniscal fasteners have been produced, e.g., arrows, tacks, T-bars, barbs-and-sutures, screws, etc. However, all of the fasteners developed to date tend to suffer from one or more disadvantages. Among these is the common—and quite significant—disadvantage associated with positioning a rigid component within the interior of the knee. More particularly, all of the fasteners developed to date incorporate at least one rigid component into their design. If the rigid component is not properly positioned at the time of deployment, and/or if the rigid component should subsequently migrate out of position, serious joint abrasion can result.

As a result, there is a significant need for a new and improved method and apparatus for meniscal repair.

SUMMARY OF THE INVENTION

The present invention provides an improved method and apparatus for meniscal repair which addresses the problems associated with the prior art. More particularly, the present invention comprises the provision and use of a novel meniscal suturing system which makes suturing of the meniscus easy, safe and reliable.

In one form of the present invention, there is provided apparatus for suturing tissue, wherein the apparatus comprises:

a housing;
a first needle mounted to the housing;
a second needle mounted to the housing;
a suture having a leading portion and a trailing portion;
a first structure associated with the first needle for passing the leading portion of the suture from a near side of the tissue to a far side of the tissue; and
a second structure associated with the second needle for retracting the leading portion of the suture from the far side of the tissue back to the near side of the tissue.

In another form of the present invention, there is provided apparatus for suturing tissue, wherein the apparatus comprises:

a housing;
a first needle mounted to the housing;
a second needle mounted to the housing;
a suture having a leading portion and a trailing portion;
a first structure associated with the first needle for passing the leading portion of the suture from a near side of the tissue to a far side of the tissue;
a second structure associated with the second needle for retracting the leading portion of the suture from the far side of the tissue back to the near side of the tissue;
a pre-formed, uncinched knot formed in the trailing portion of the suture; and
a support for releasably supporting the pre-formed, uncinched knot relative to the housing.

In another form of the present invention, there is provided a method for suturing tissue, the method comprising the steps of:

providing a suture having a leading portion and a trailing portion, wherein a pre-formed, uncinched knot is formed in the trailing portion of the suture;
passing the leading portion of suture from a near side of the tissue to a far side of the tissue;
retracting the leading portion of the suture from the far side of the tissue back to the near side of the tissue;
passing the retracted leading portion of the suture through the pre-formed, uncinched knot formed in the trailing portion of the suture; and
cinching the knot so as to secure the suture in the tissue.

BRIEF DESCRIPTION OF THE DRAWINGS

These and other objects, features and advantages of the present invention will be more fully disclosed in, or rendered obvious by, the following detailed description of the preferred embodiments of the invention, which is to be considered together with the accompanying drawings wherein like numbers refer to like parts and further wherein:

FIGS. 92-103 are a series of views showing a fifth method and apparatus for repairing a meniscal tear.

DETAILED DESCRIPTION OF THE PREFERRED EMBODIMENTS

First Preferred Method and Apparatus

Figure 1:
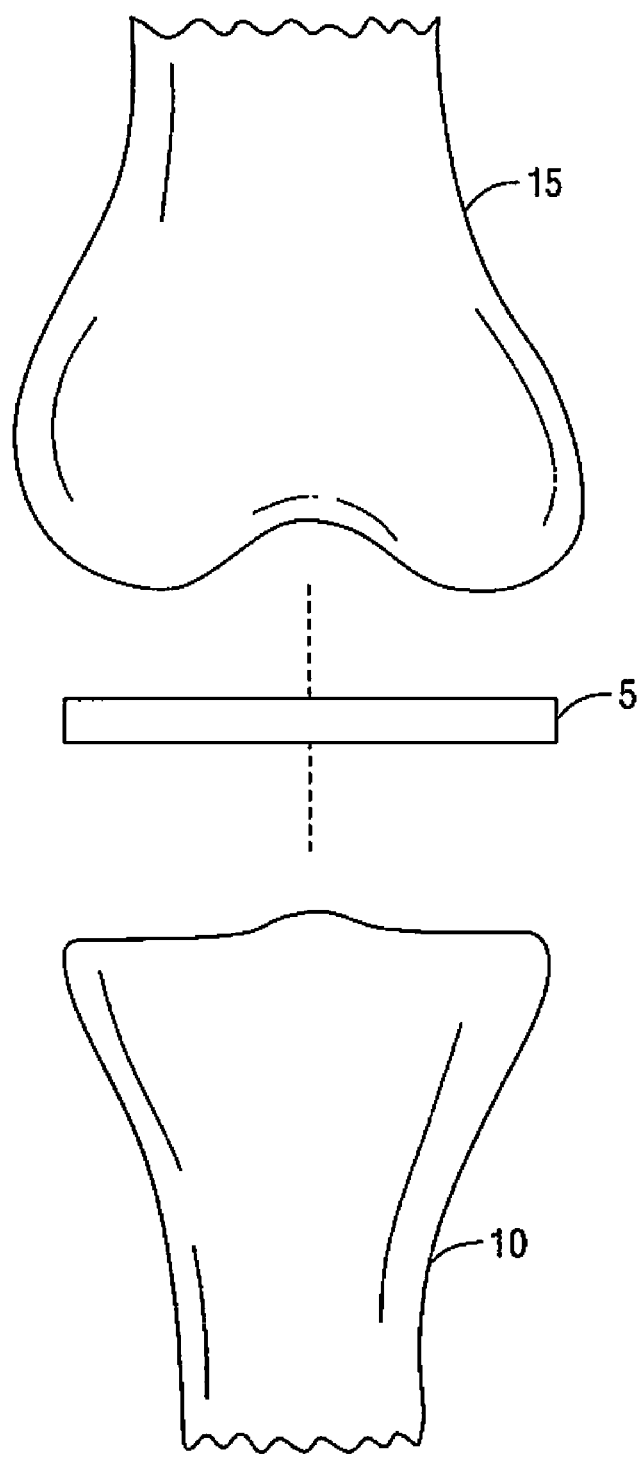
FIG. 1 is a schematic front view of a knee joint.
Figure 2:
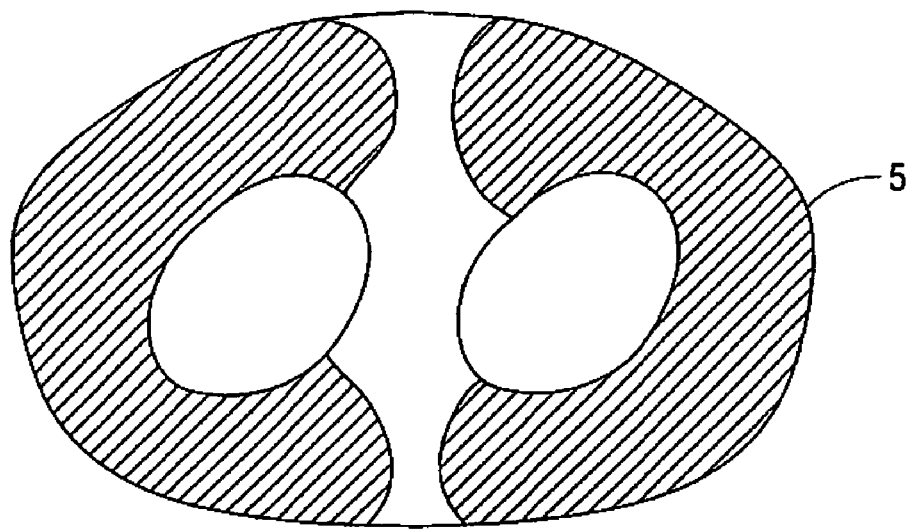
FIG. 2 is a schematic top view, in cross-section, of the meniscus of the knee joint.
Figure 3:
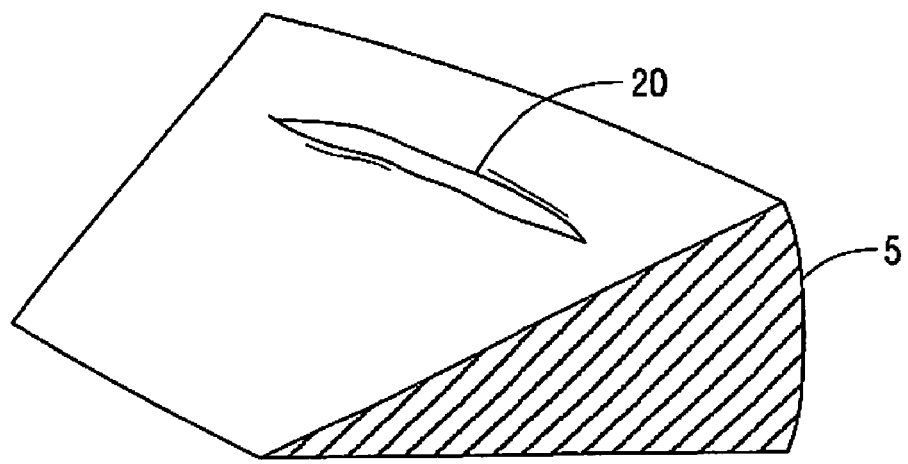
FIG. 3 is a schematic perspective view, in partial section, of the meniscus of the knee joint.
Figure 4:
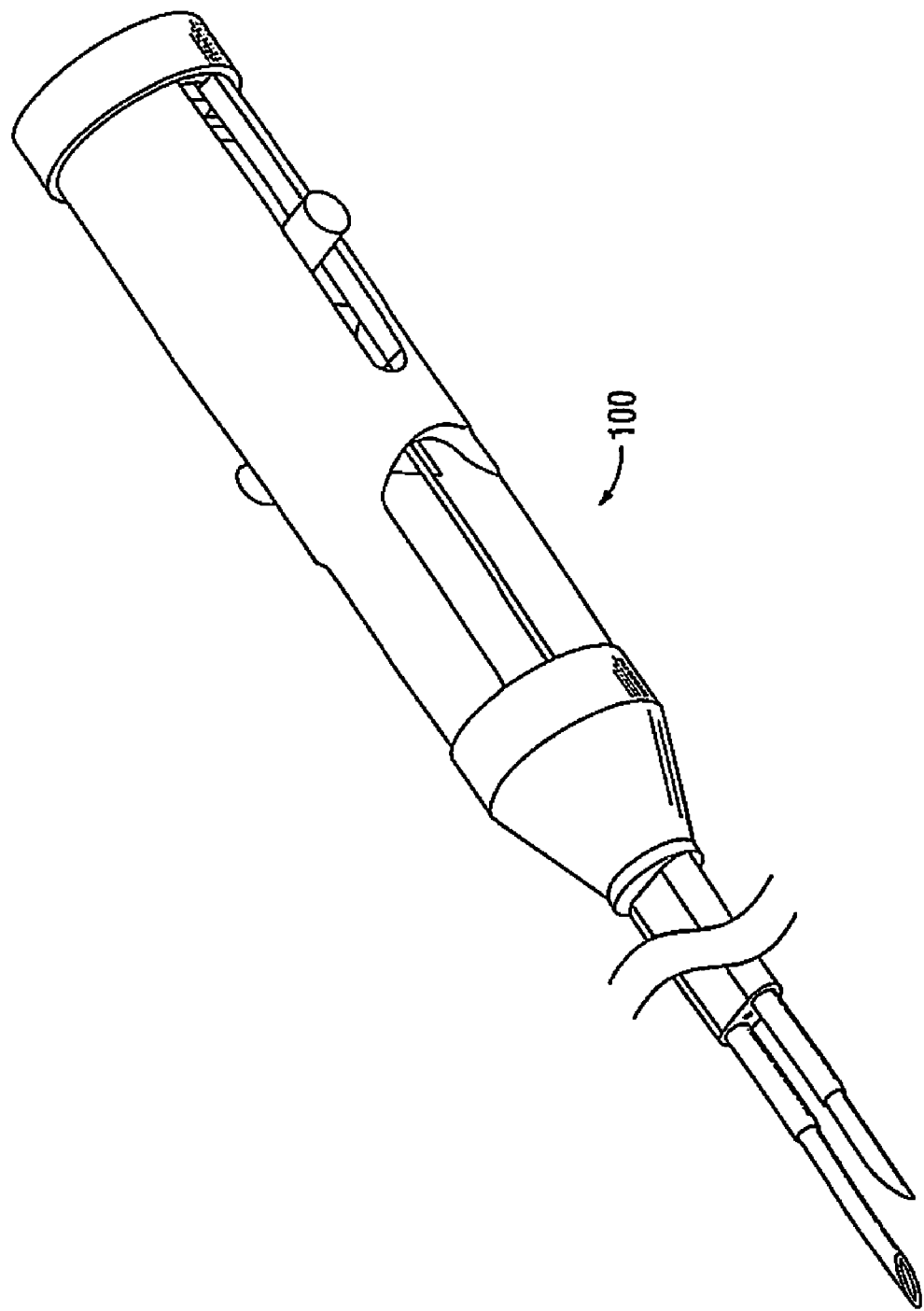
FIGS. 4-16 are a series of views showing a first method and apparatus for repairing a meniscal tear.
Figure 5:
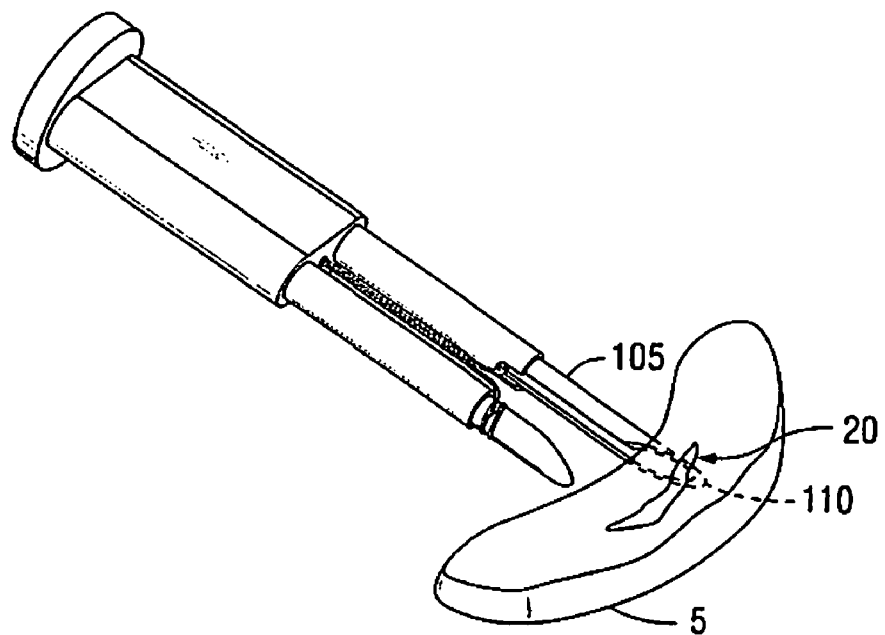

Looking first at FIGS. 4 and 5, there is shown an apparatus 100 for use in closing tear 20 in meniscus 5.

More particularly, in one preferred form of the present invention, and still looking now at FIGS. 4 and 5, a first needle 105 is first advanced so that its distal tip 110 is positioned within, but not completely through, meniscus 5.

Figure 6:
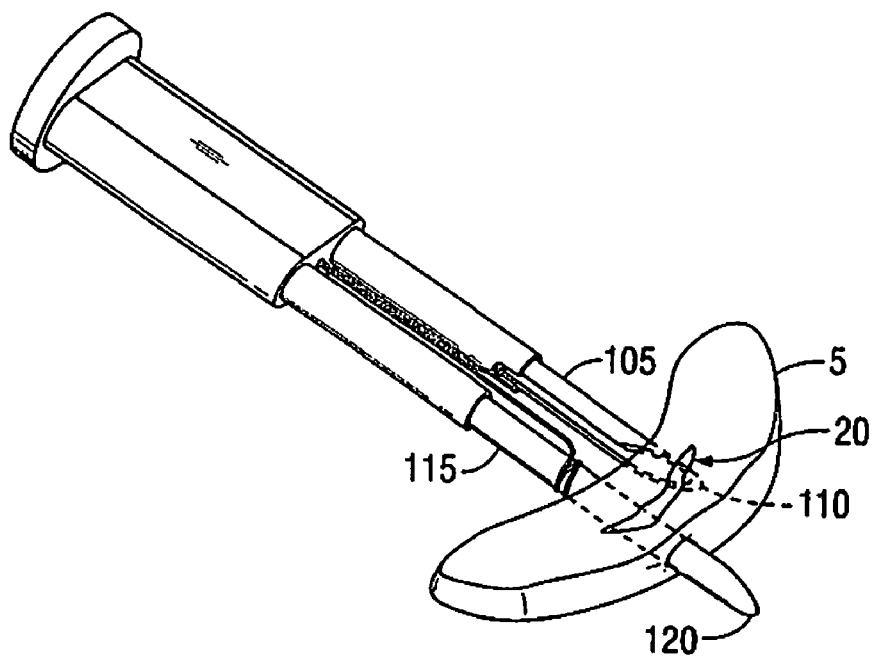

Next, as seen in FIG. 6, a second needle 115 is advanced completely through the meniscus, so that the distal tip 120 of second needle 115 is positioned on the far side of the meniscus.

Figure 7:
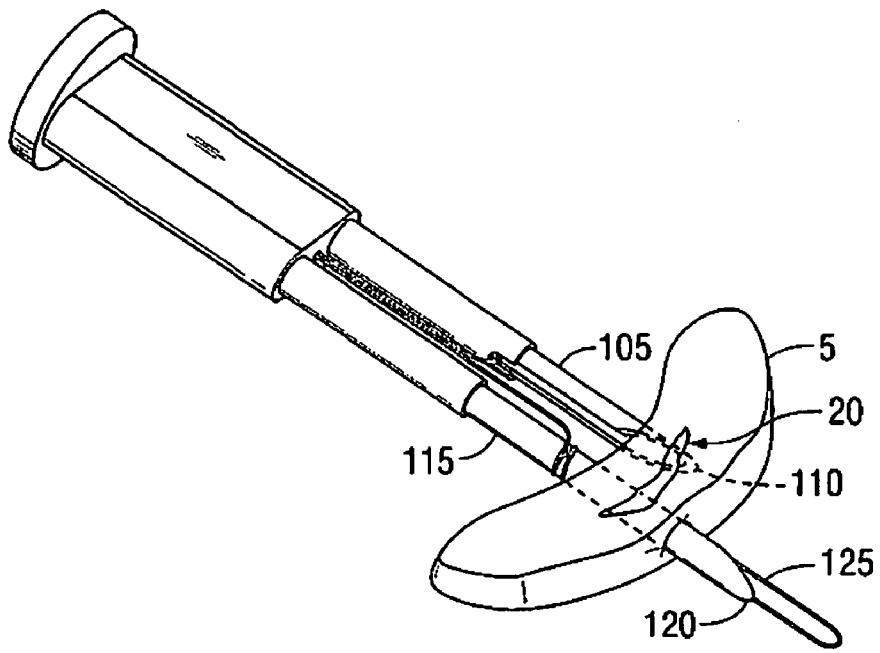
Figure 8:
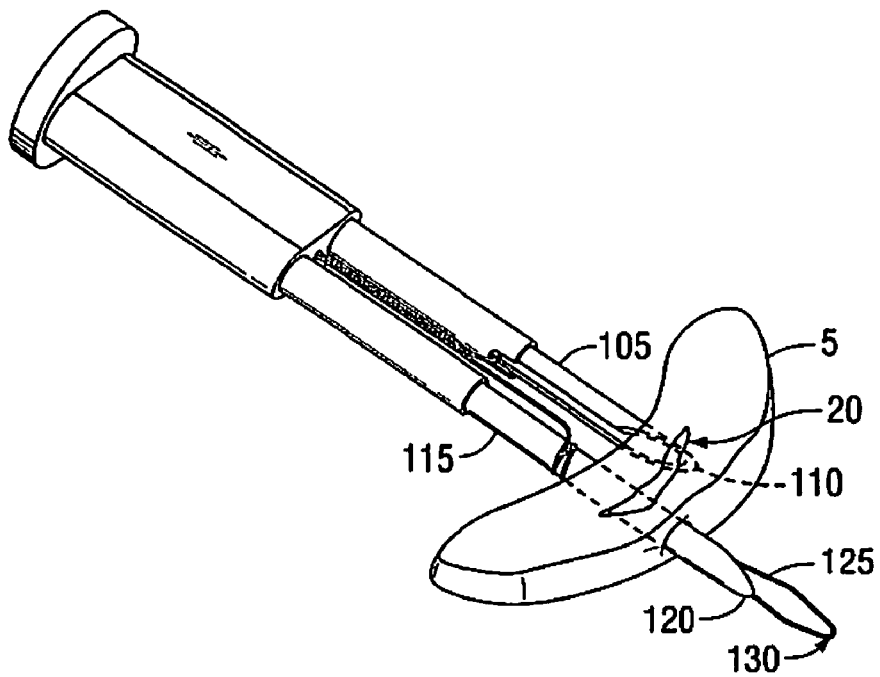
Figure 9:
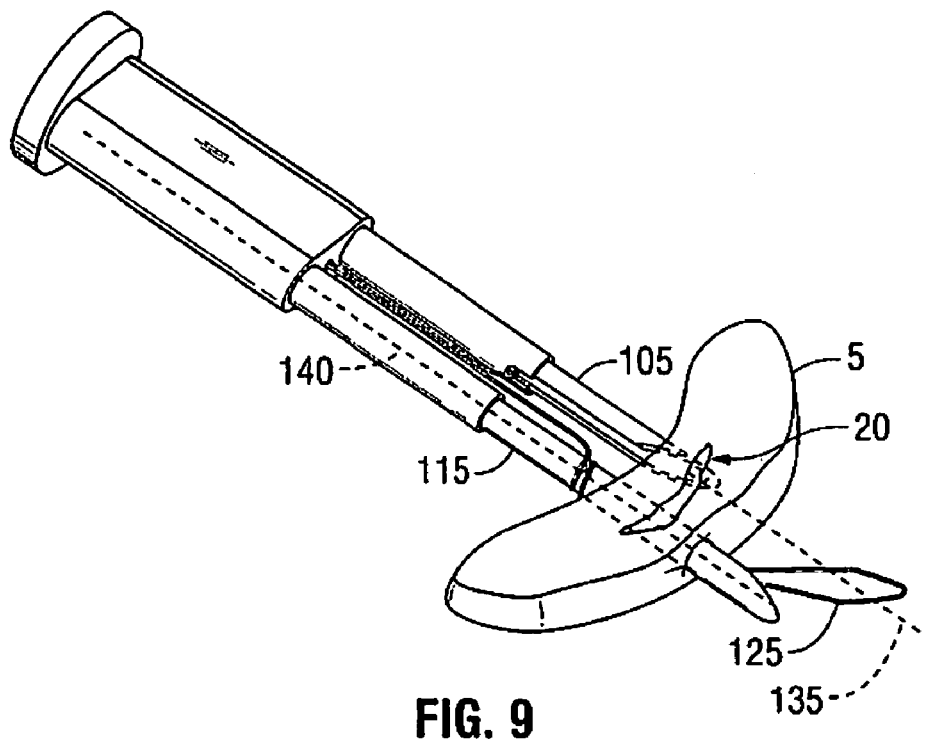

Then, and looking now at FIGS. 7-9, a snare 125 is advanced out the distal end 120 of second needle 115. Snare 125 is formed and arranged so that when the snare is in its fully-extended position (FIG. 9), the loop 130 of snare 125 is axially aligned with the longitudinal axis 135 of first needle 105. To this end, snare 125 may comprise an elongated body 140 having the loop 130 set at its distal end, with loop 130 being set at an angle to the longitudinal axis of elongated body 140. At least one of loop 130 and elongated body 140 comprises a resilient material, in order that loop 130 and elongated body 140 may be (i) received within second needle 115, and (ii) loop 130 may project across the longitudinal axis 135 of first needle 105 when snare 125 is in its fully-extended position (FIG. 9).

Figure 10:
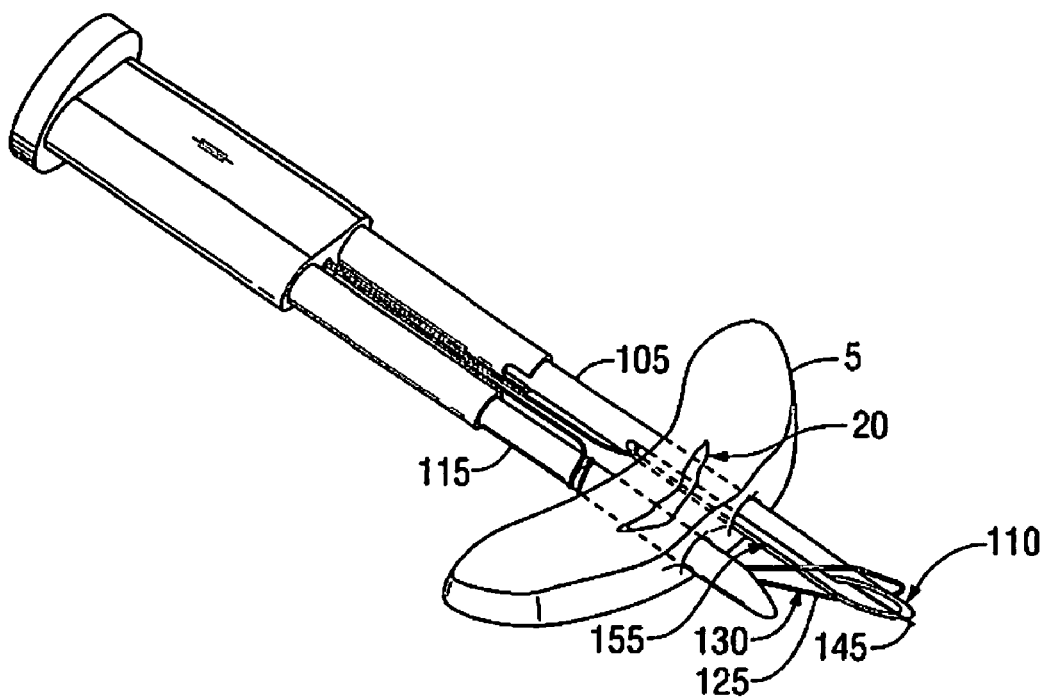

Next, and looking now at FIG. 10, first needle 105 is advanced completely through meniscus 5, so that the distal end 110 of first needle 105 extends through loop 130 of snare 125.

Then first needle 105 is used to advance a suture 145 through loop 130 of snare 125. This may be effected in a variety of ways.

Figure 11:
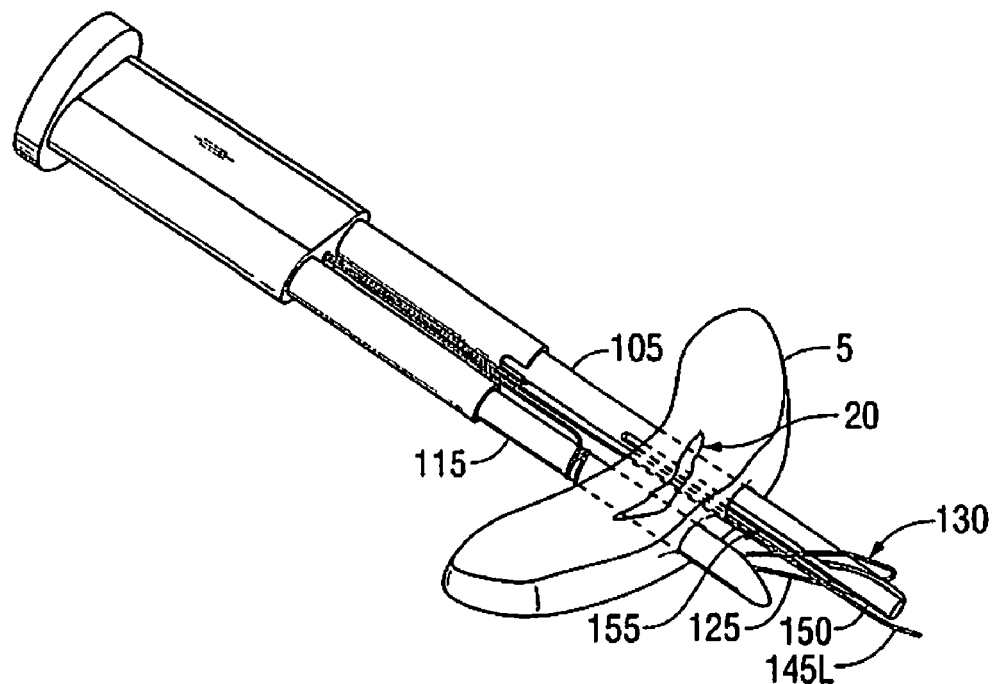
Figure 12:
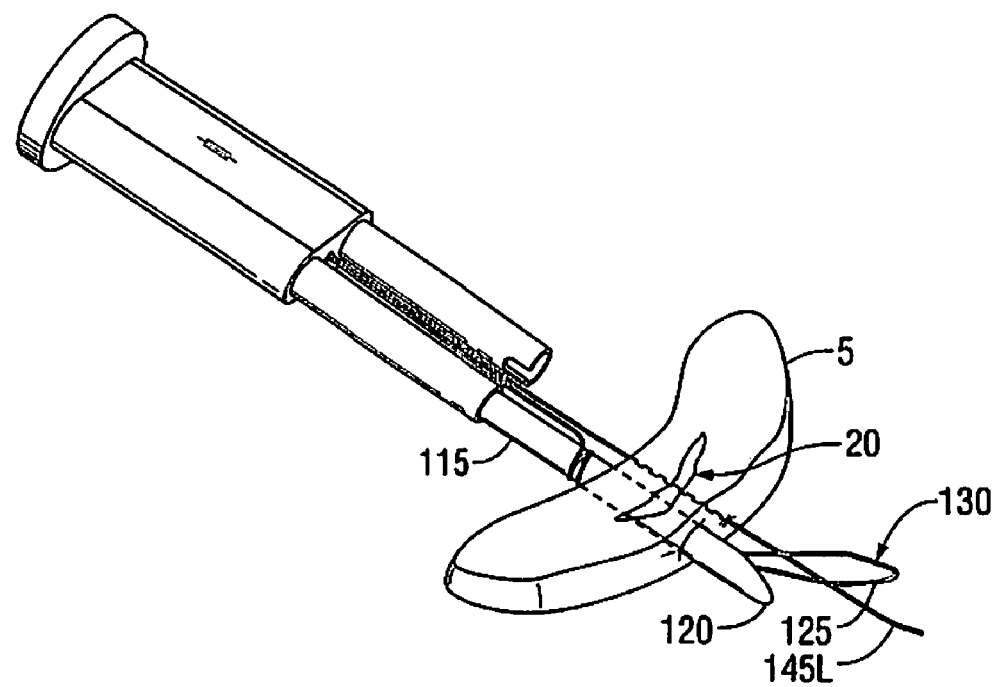

By way of example but not limitation, and looking now at FIGS. 10-12, suture 145 may be pre-disposed within first needle 105 so that suture 145 is carried through the meniscus and through loop 130 of snare 125 with the advancement of first needle 105. Then a driver 150 may be used to eject the leading portion 145L (FIG. 11) of suture 145 from the interior of first needle 105. To this end, a slot 155 may be provided in first needle 105 to assist in ejecting leading portion 145L of suture 145 from first needle 105. Finally first needle 105 is withdrawn, leaving leading portion 145L of suture 145 extending through (i) meniscus 5, and (ii) loop 130 of snare 125. The approach shown in FIGS. 10-12 can be advantageous in many circumstances, since it works well with both braided suture and monofilament suture. In this respect it will be appreciated that braided suture is generally preferable for meniscal repairs, since it tends to form a smaller knot which is less susceptible to slipping.

In an alternative approach, where suture 145 has sufficient column strength (e.g., where suture 145 comprises relatively thick monofilament suture), after first needle 105 is advanced through meniscus 5 (FIG. 10) and through loop 130 of snare 125, the suture can be pushed through first needle 105 so that leading portion 145L of suture 145 extends through both meniscus 5 and loop 130 of snare 125. Then, while suture 145 is maintained in place, first needle 105 can be withdrawn, with the column strength of the suture ensuring that leading portion 145L of suture 145 does not retreat from its position extending through meniscus 5 and loop 130 of snare 125. Of course, this latter approach does suffer from the disadvantage that it requires the use of suture with sufficient column strength (e.g., monofilament suture) and hence this approach can be difficult to practice with conventional braided suture.

Figure 13:
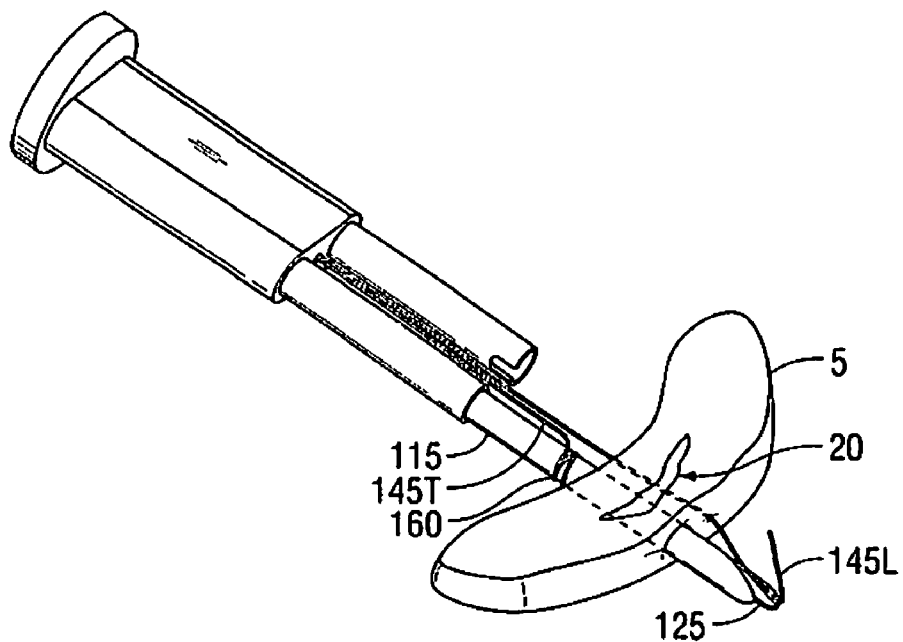
Figure 14:
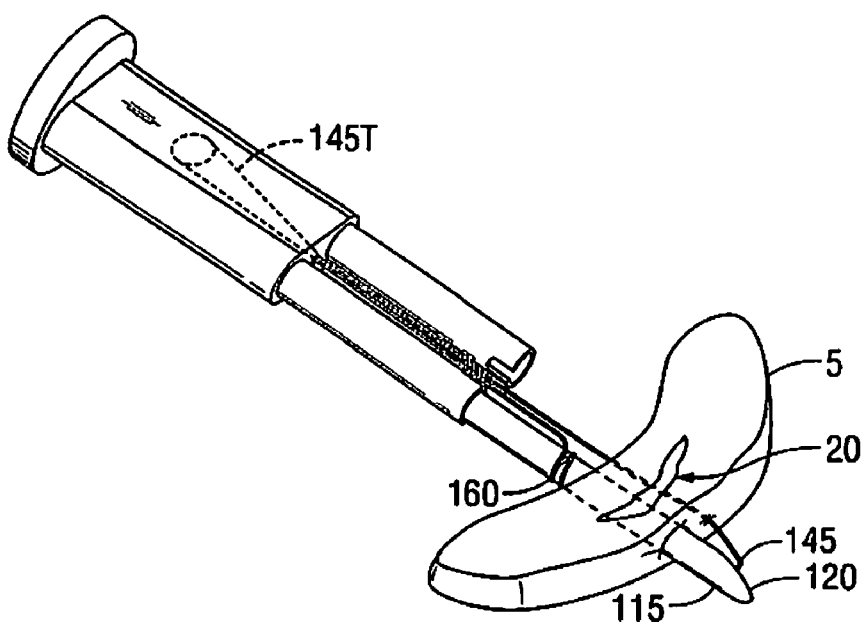
Figure 15:
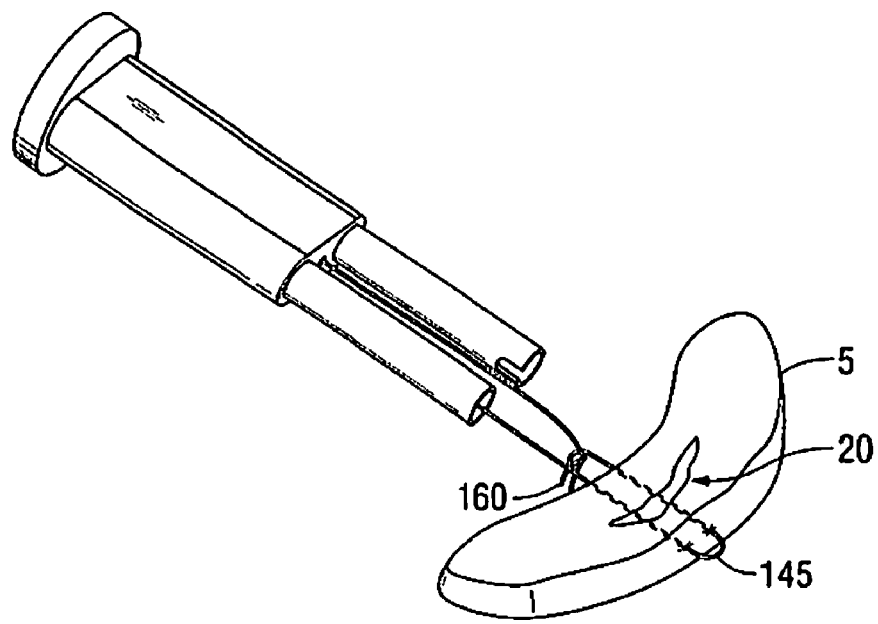

Regardless of the particular approach used to achieve the position shown in FIG. 12, once this position has been achieved, the next step is to carry leading portion 145L of suture 145 back to the near side of the meniscus. More particularly, and looking now at FIGS. 13-15, snare 125 is retracted back into second needle 115, and then second needle 115 is withdrawn back through the meniscus, carrying leading portion 145L of suture 145 with it.

Thus, at this point in the procedure, suture 145 will have been passed from the near side of the meniscus, across the meniscus and then back again. Significantly, by appropriately positioning the first needle 105 and second needle 115 during the suture passing operation, the suture will extend across the tear 20 formed in meniscus 5.

Next, the suture is tied down so as to close the tear in the meniscus. This may be done in a variety of ways which will be apparent to those skilled in the art in view of the present disclosure. However, in one preferred form of the invention, a trailing portion 145T of suture 145 may be arranged in the form of a pre-formed, uncinched knot 160 disposed about the exterior of second needle 115 (see, for example, FIGS. 13 and 14), with an intermediate portion 145I of suture 145 being disposed within apparatus 100. As a result of this construction, when snare 125 and second needle 115 carry leading portion 145L of suture 145 back through the meniscus, they will also carry leading portion 145L of suture 145 back through pre-formed, uncinched knot 160 (FIG. 15), which is itself formed from trailing portion 145T of that same suture 145. It will be appreciated that, as second needle 115 is withdrawn, pre-formed, uncinched knot 160 will slip off the end of second needle 115, into direct contact with leading portion 145L of suture 145, as the suture passes back through itself.

Figure 16:
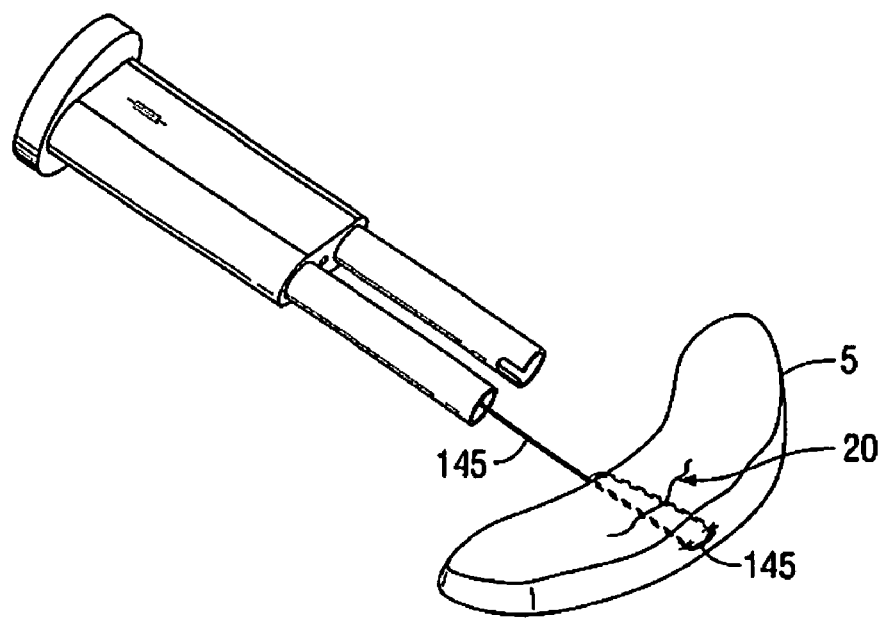

Then, and looking now at FIG. 16, suture 145 is pulled taut so as to simultaneously (i) pull tear 20 closed, and (ii) tighten pre-formed knot 160 onto the suture, whereby to fix the suture in position and thereby close tear 20 in meniscus 5. The trailing end 145T of suture 145 can then be trimmed away in ways well known in the art, thereby leaving a low-profile suture fixation within the meniscus.

Second Preferred Method and Apparatus

Figure 17:
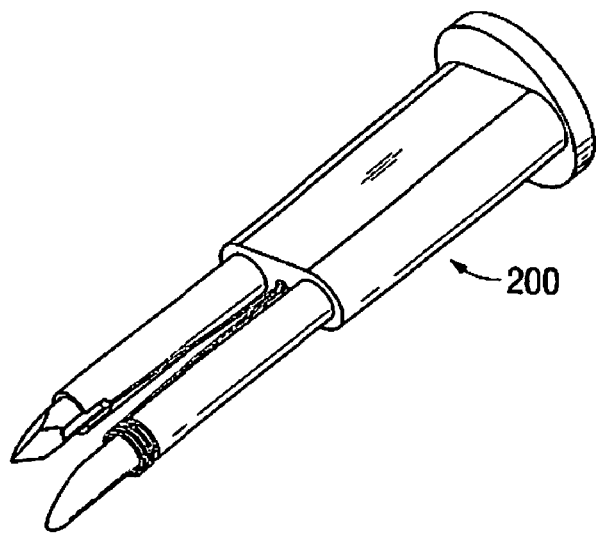
FIGS. 17-30 are a series of views showing a second method and apparatus for repairing a meniscal tear.
Figure 18:
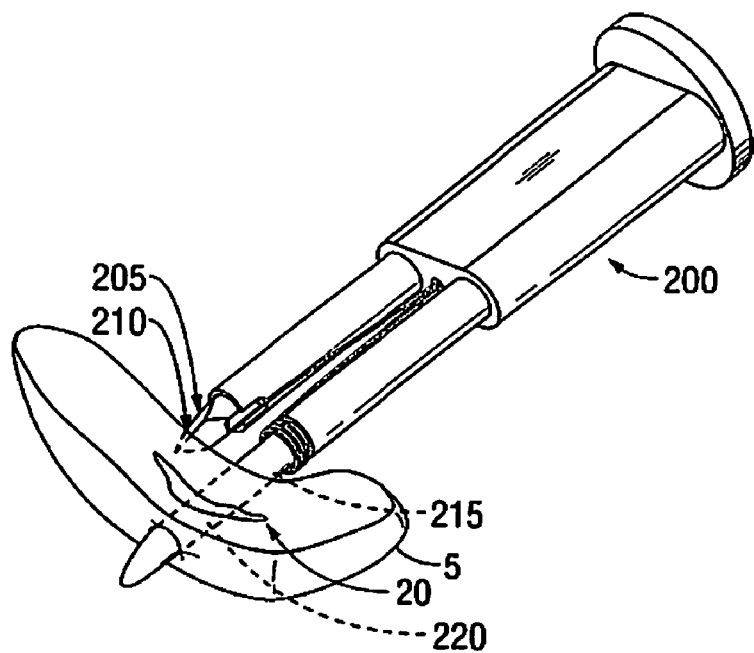

Looking now at FIGS. 17 and 18, there is shown an apparatus 200 for use in closing tear 20 in meniscus 5.

More particularly, in one preferred form of the invention, and still looking now at FIGS. 17 and 18, a first needle 205 is first advanced so that its distal tip 210 is positioned within, but not completely through, meniscus 5.

Figure 19:
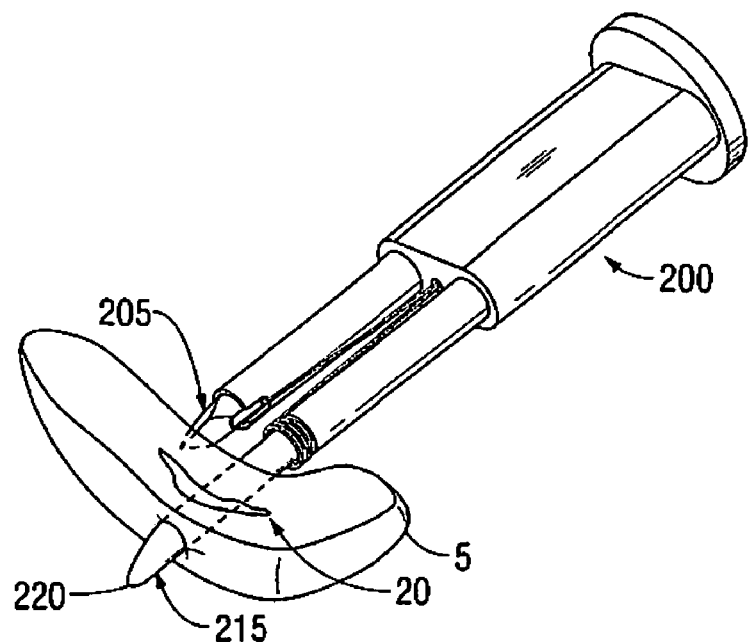

Next, as seen as FIG. 19, a second needle 215 is advanced completely through the meniscus, so that the distal tip 220 of second needle 215 lies on the far side of the meniscus.

Figure 20:
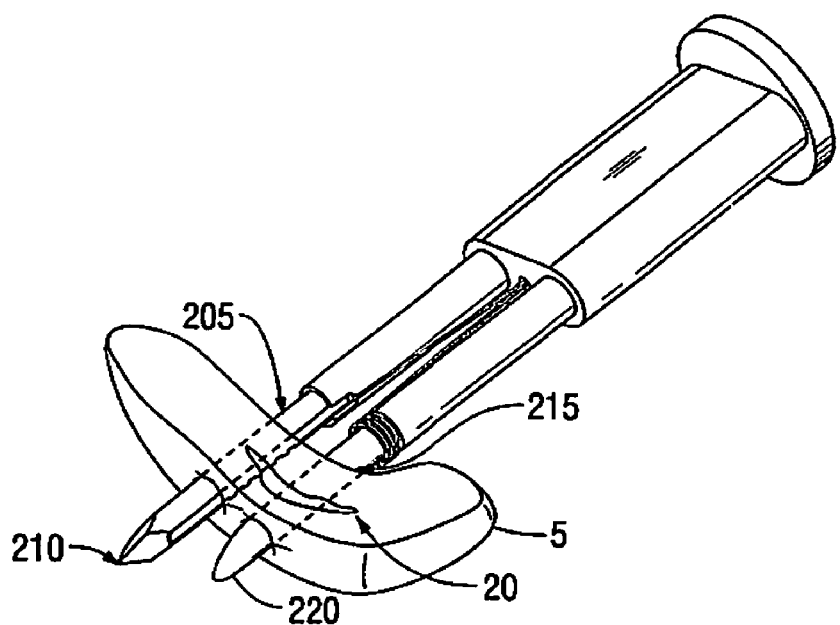

Then, and looking now at FIG. 20, first needle 205 is advanced all the way across meniscus 5.

Figure 21:
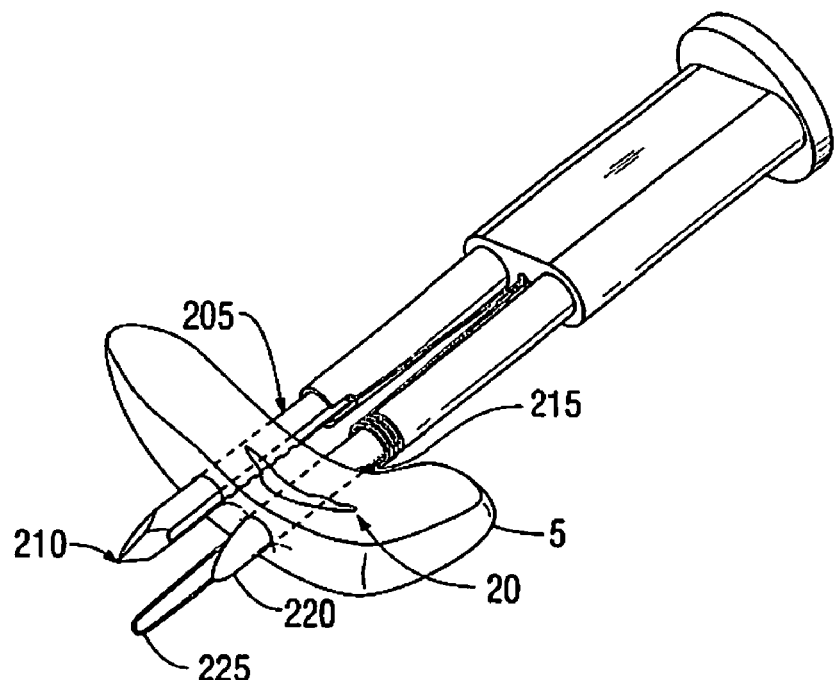
Figure 22:
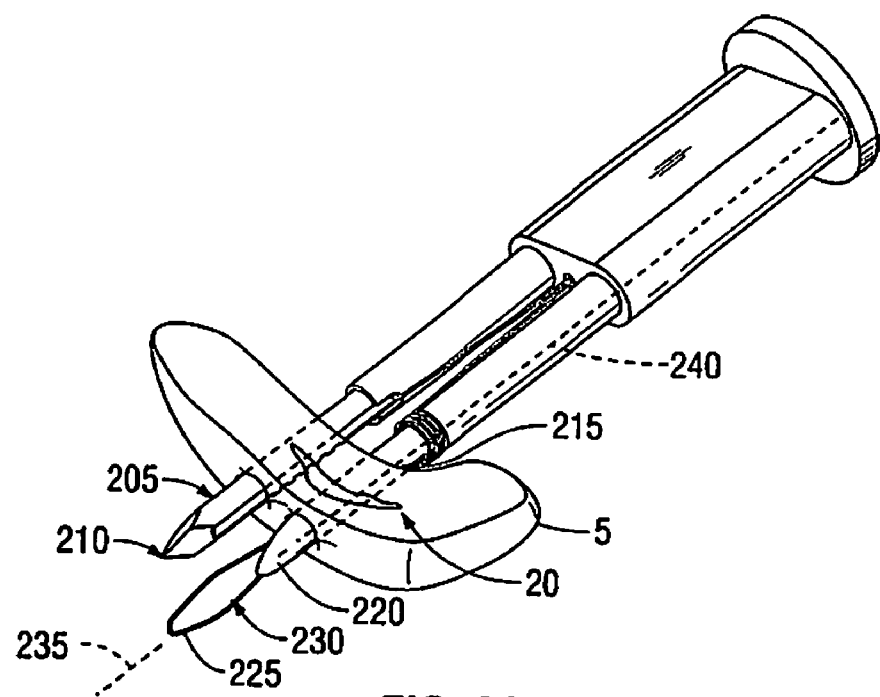

Then, and looking now at FIGS. 21 and 22, a snare 225 is advanced out the distal end 220 of second needle 215. Snare 225 is formed and arranged so that when the snare is in its fully-extended position (FIG. 22), the loop 230 of snare 225 is axially aligned with the longitudinal axis 235 of second needle 215. To this end, snare 225 may comprise an elongated body 240 having loop 230 set at its distal end, with loop 230 being aligned with the longitudinal axis of elongated body 240.

Figure 23:
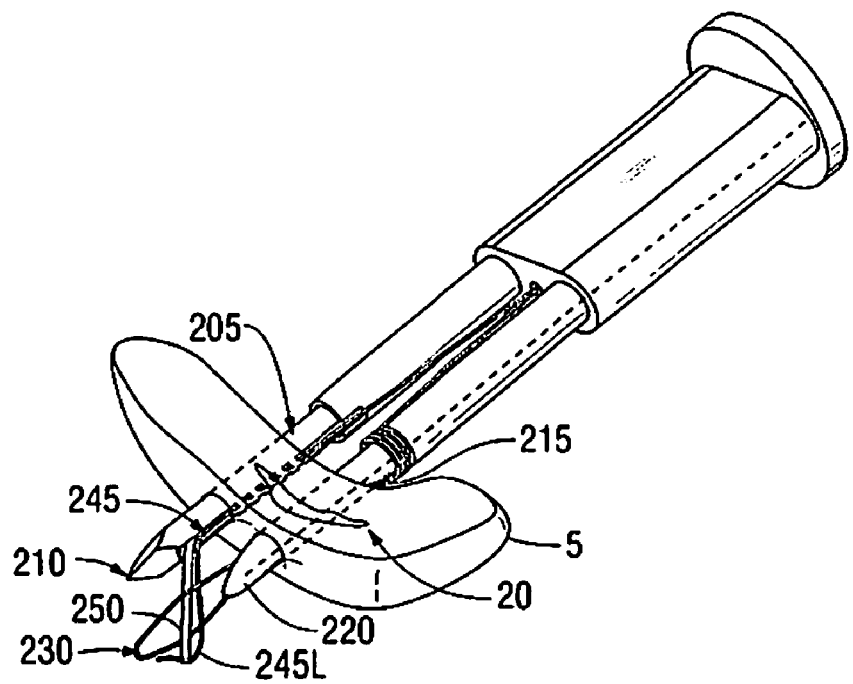

Next, and looking now at FIG. 23, a suture holder 250 carrying a suture 245 is advanced out the distal end 210 of first needle 205. Suture holder 250 is configured so that the suture holder will carry the leading portion 245L of suture 245 through loop 230 of snare 225 when the suture holder is extended out of first needle 205.

Figure 24:
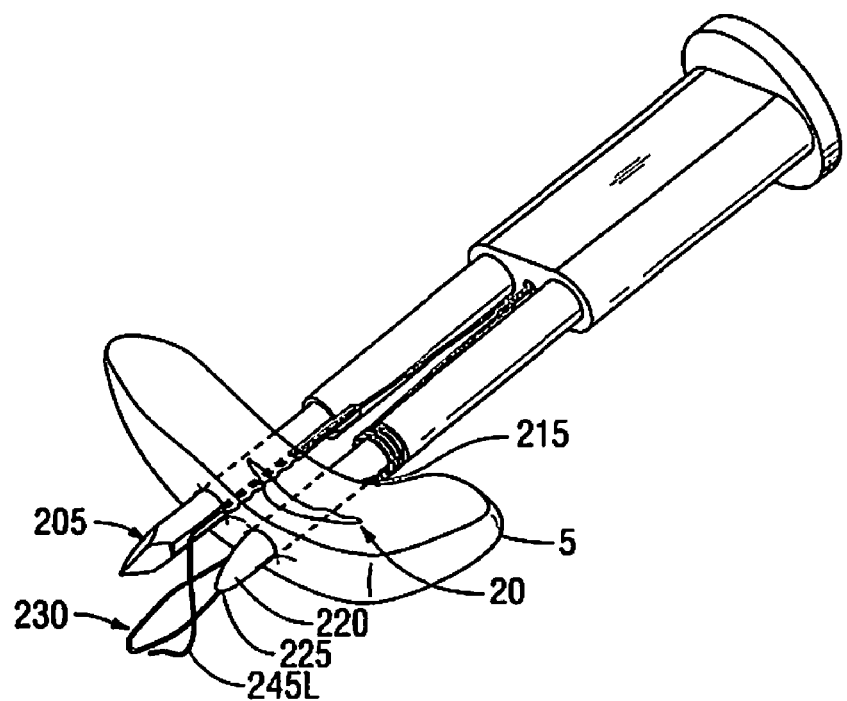
Figure 25:
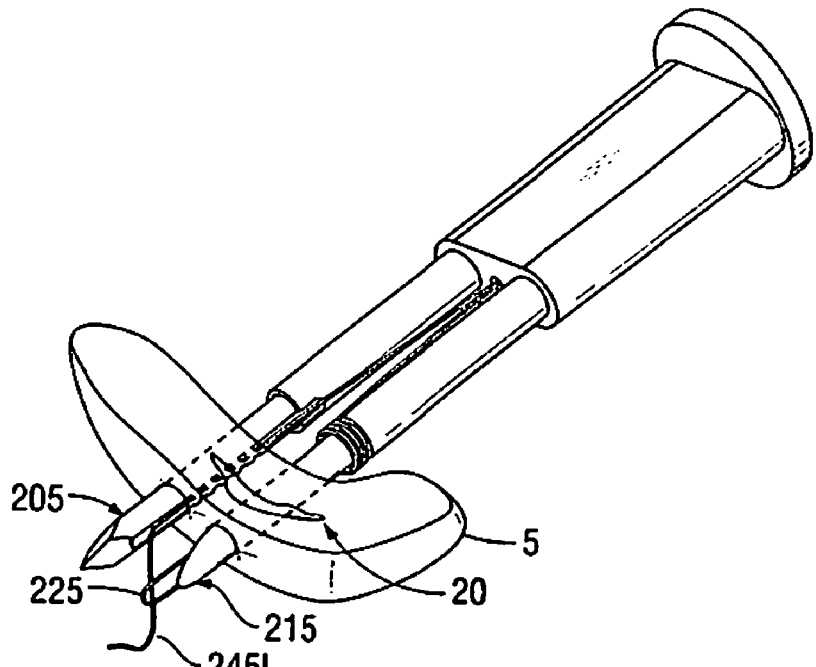
Figure 26:
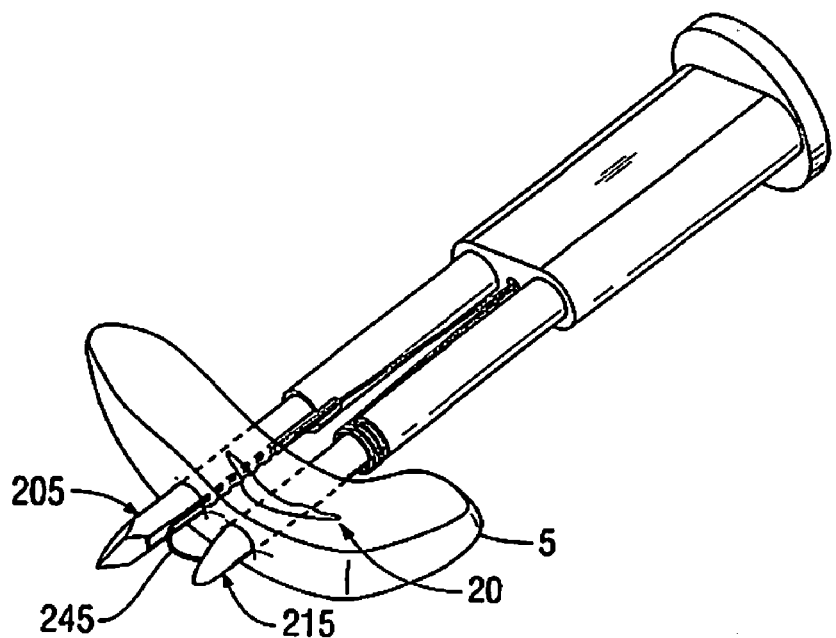
Figure 27:
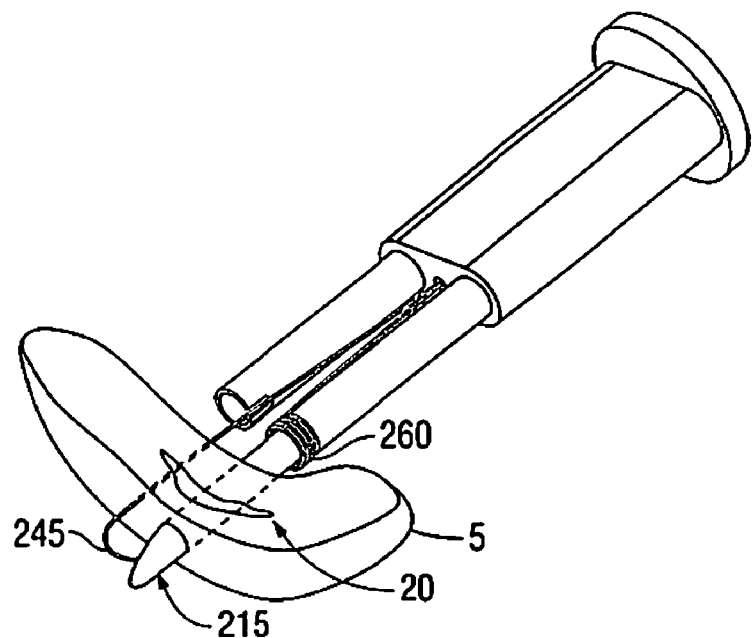
Figure 28:
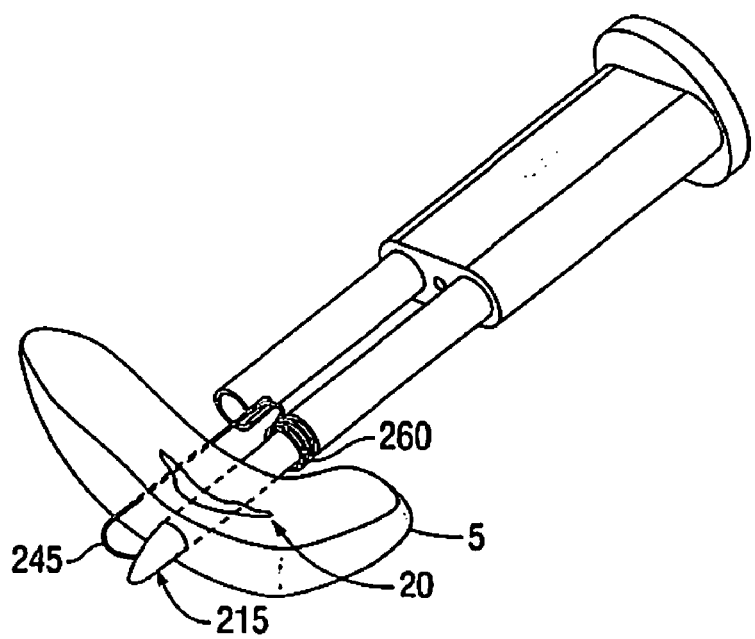
Figure 29:
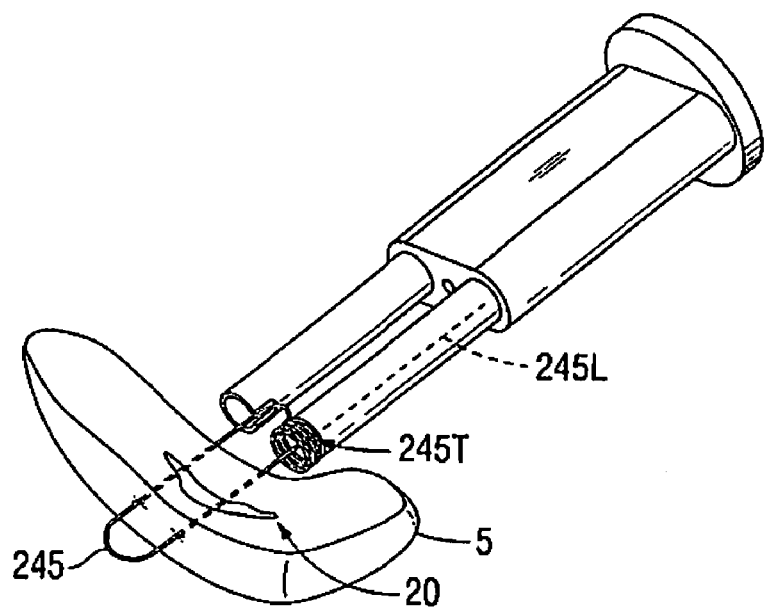

Then suture holder 250 is withdrawn, leaving the leading portion 245L of suture 245 extending though loop 230 of snare 225 (FIG. 24).

Next, leading portion 245L of suture 245 is carried back to the near side of the meniscus. More particularly, and looking now at FIGS. 25-29, snare 225 is retracted back into second needle 215, second needle 215 is withdrawn back through the meniscus, and then first needle 205 is withdrawn back through the meniscus.

Thus, at this point in the procedure, suture 245 will have been passed from the near side of the meniscus, through the meniscus and then back again. Significantly, by appropriately positioning first needle 205 and second needle 215 during the suture passing operation, suture 245 will extend across tear 20 formed in meniscus 5.

Next, the suture is tied down so as to close the tear in the meniscus. This may be done in a variety of ways which will be apparent to those skilled in the art in view of the present disclosure. However, in one preferred form of the invention, the trailing portion 245T of suture 245 may be arranged in the form of a pre-formed, uncinched knot 260 disposed about the exterior of second needle 215 (see, for example, FIG. 28) so that when snare 225 and second needle 215 carry leading portion 245L of suture 245 back through the meniscus, they will also carry leading portion 245L of suture 245 back through pre-formed, uncinched knot 260 (FIG. 29), which is formed by trailing portion 245T of suture 245. It will be appreciated that, as second needle 215 is withdrawn, pre-formed, uncinched knot 260 will slip off the end of second needle 215, into direct contact with leading portion 245L of suture 245, as the suture passes back through itself.

Figure 30:
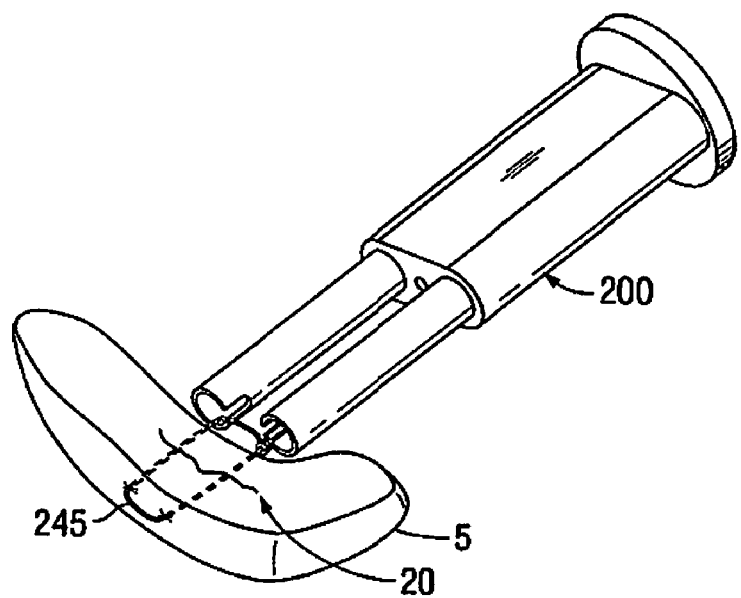
Figure 31:
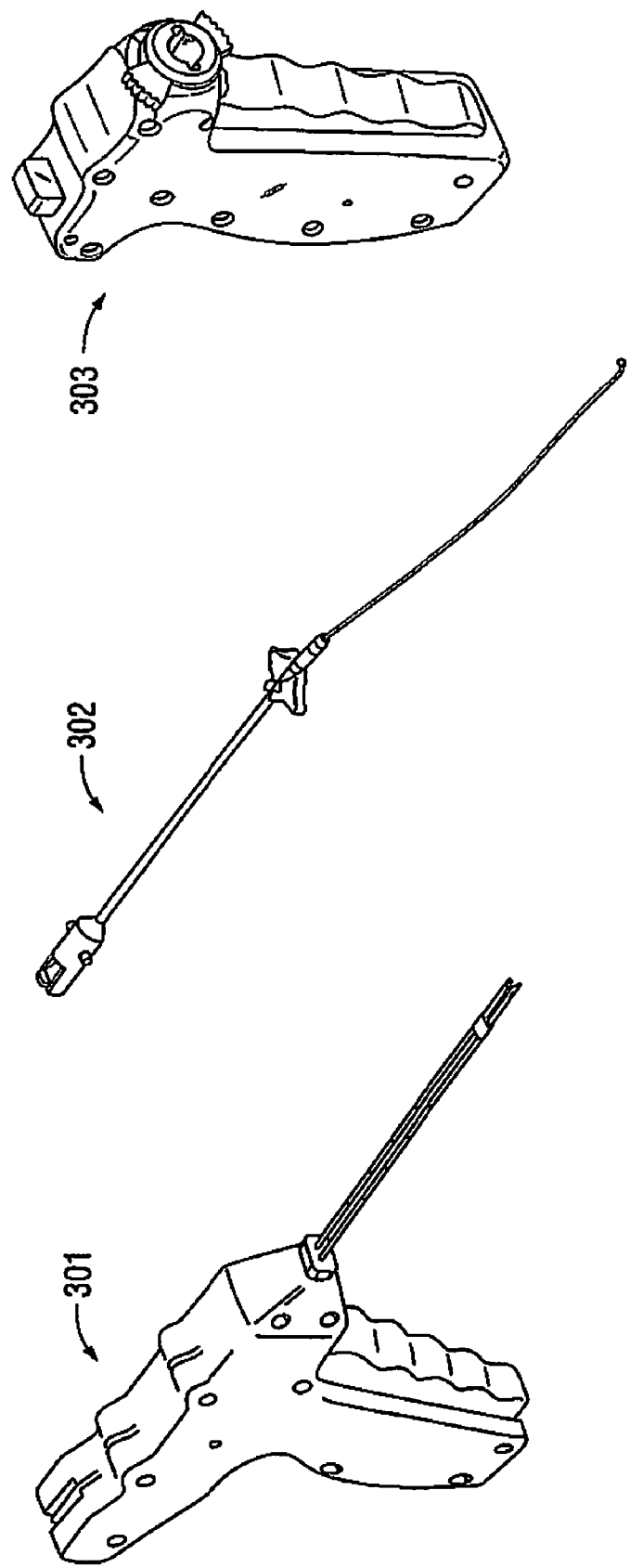
FIGS. 31-65 are a series of views showing a third method and apparatus for repairing a meniscal tear, with the meniscus being omitted from selected views in order to simplify the drawing and enhance comprehension.
Figure 32:
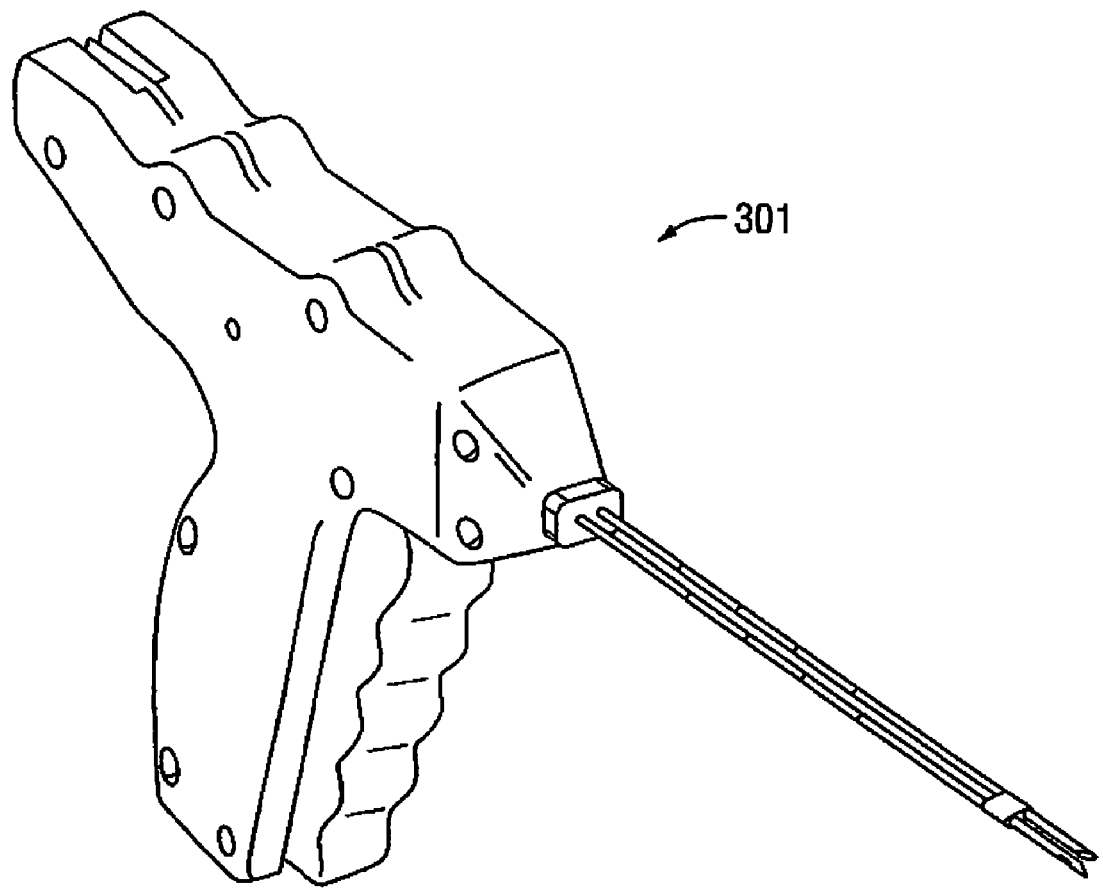
Figure 33:
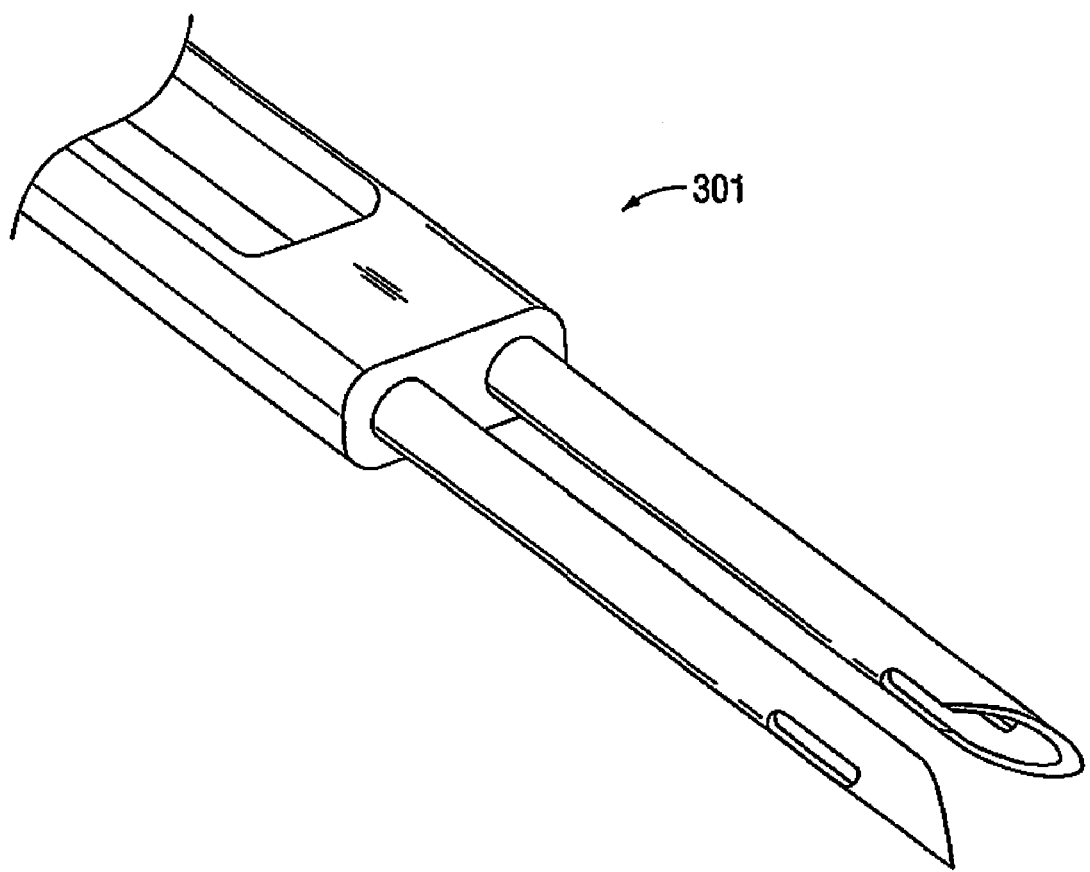
Figure 34:
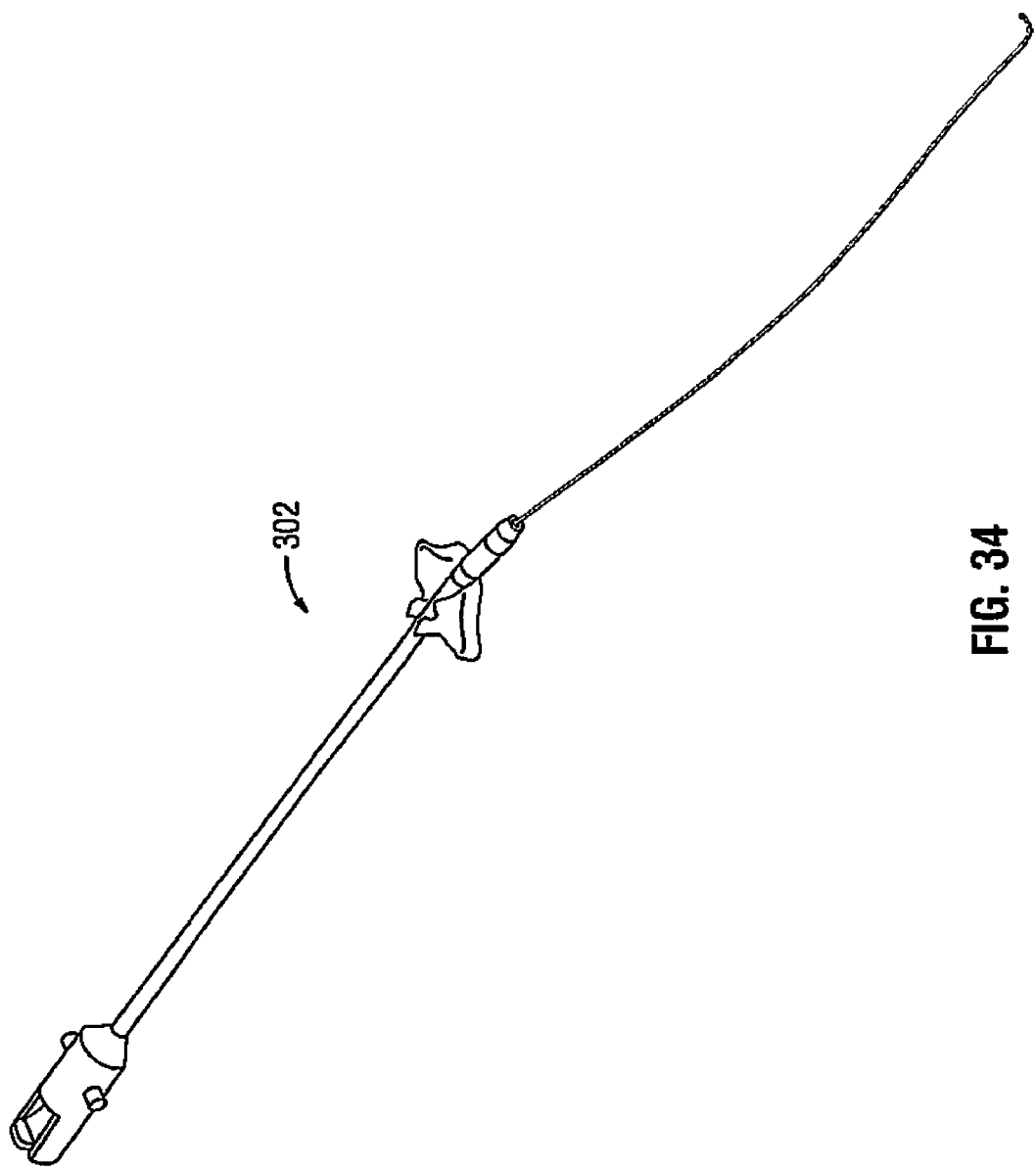

Then, and looking now at FIG. 30, trailing portion 245T of suture 245 is pulled taut so as to simultaneously (i) pull tear 20 closed, and (ii) tighten pre-formed knot 260 onto the suture, whereby to fix the suture in position and thereby close tear 20 in meniscus 5. The trailing end 245T of suture 245 can then be trimmed away in ways well known in the art, thereby leaving a low-profile suture fixation within the meniscus.

Third Preferred Method and Apparatus

Figure 35:
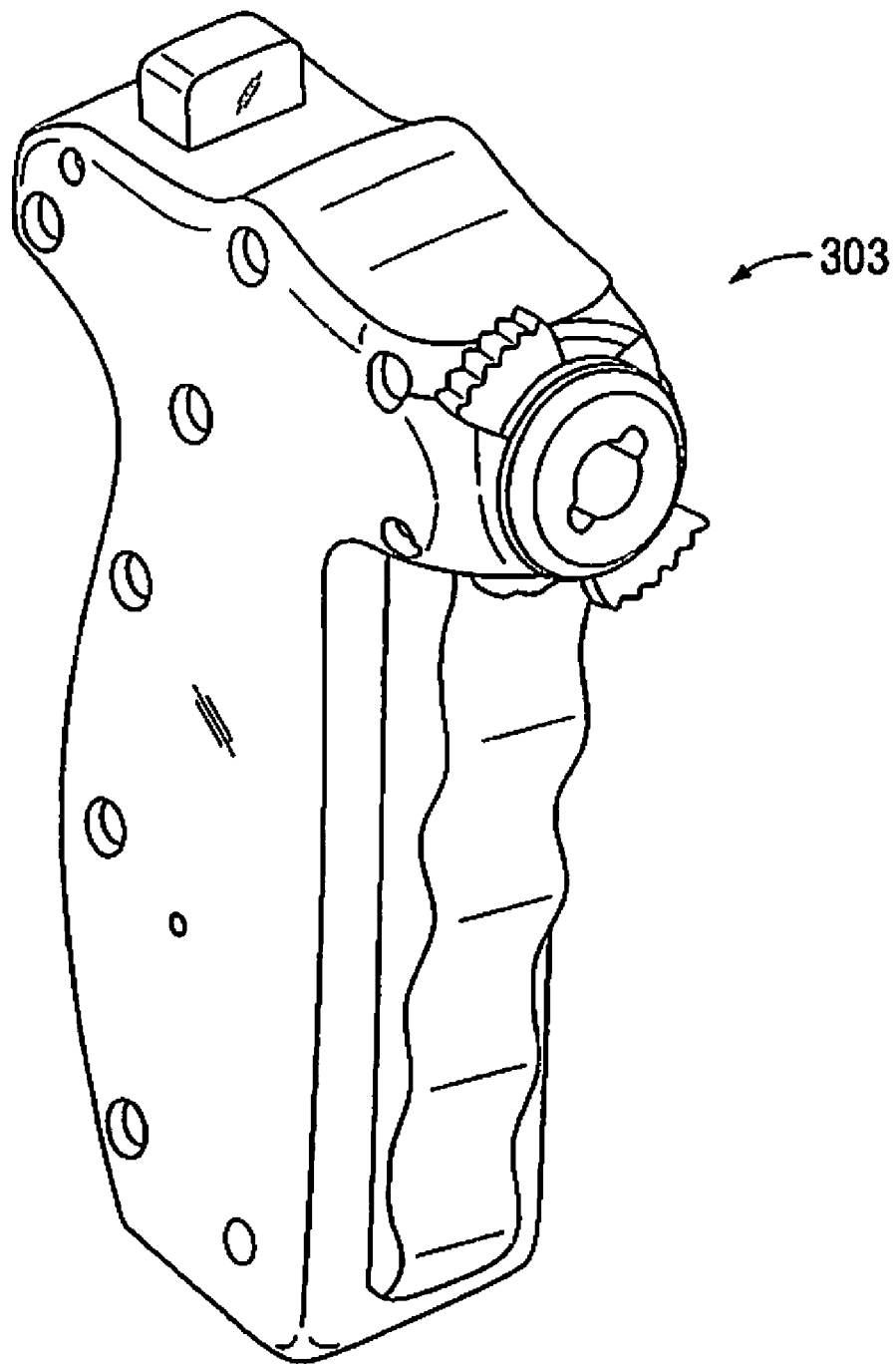
Figure 36:
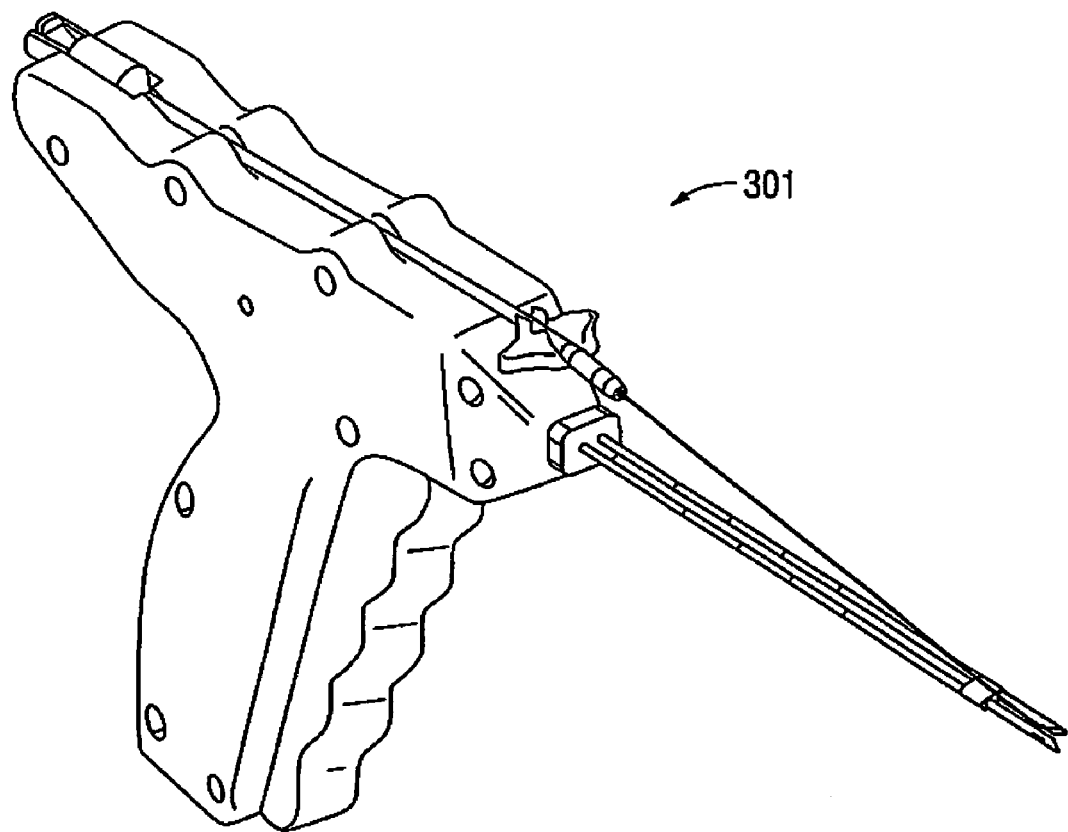
Figure 37:
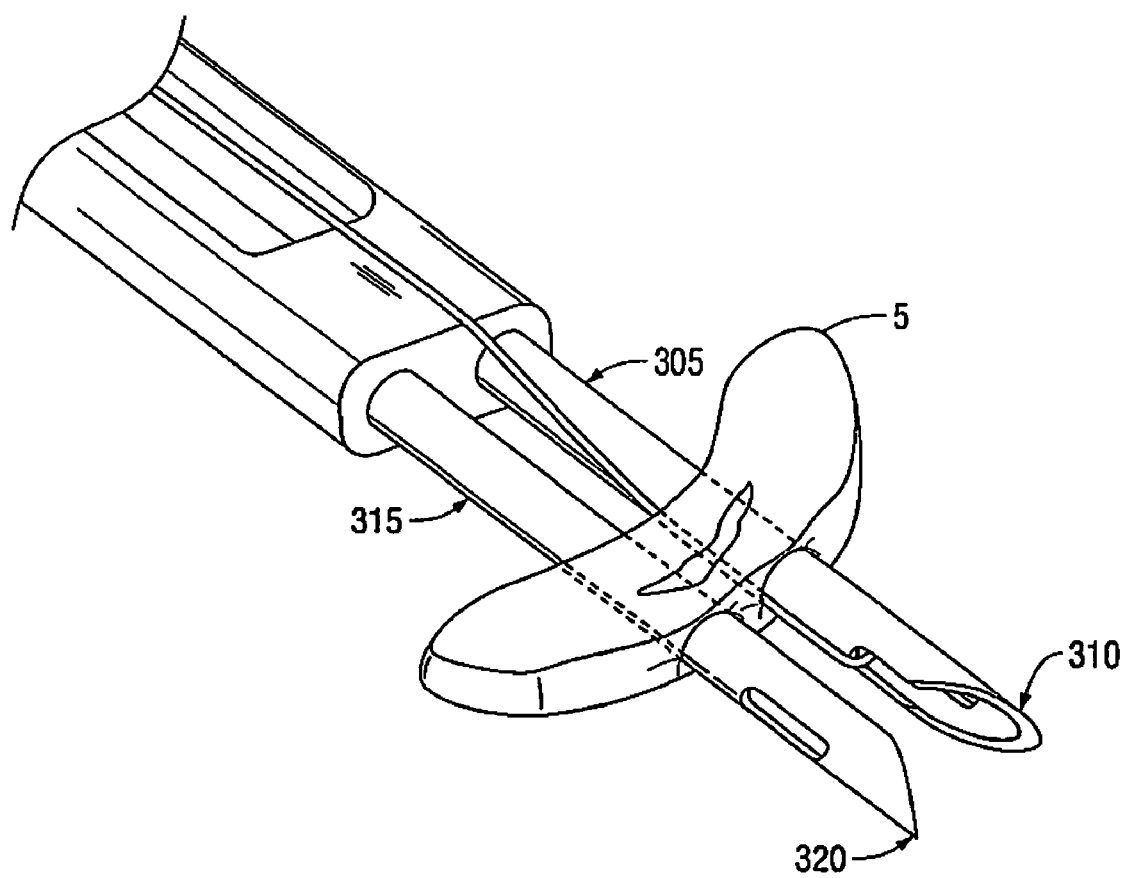

Looking now at FIGS. 31-35, there is shown an apparatus 300 for use in closing tear 20 in meniscus 5. Apparatus 300 generally comprises a suture passer 301 (FIGS. 31-33), a suture cartridge 302 (FIG. 34) and a knot pusher/cutter 303 (FIG. 35). Specific details of the construction and function of suture passer 301, suture cartridge 302 and knot pusher/cutter 303 will be disclosed in the course of the following discussion of using apparatus 300 to close tear 20 in meniscus 5.

Looking now at FIGS. 31-33, 36 and 37, suture passer 301, with suture cartridge 302 mounted thereon, is first manipulated so that its first needle 305 and its second needle 315 are advanced so that their distal tips 310, 320 are passed completely through meniscus 5.

Figure 38:
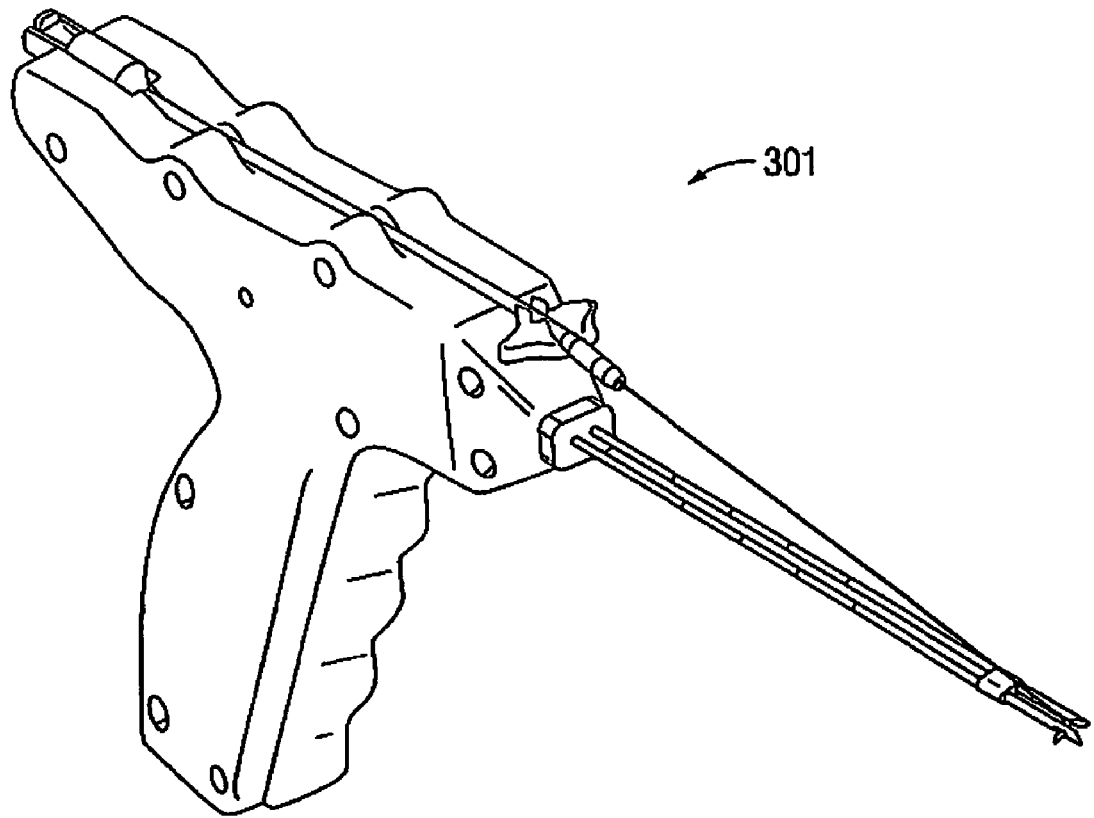
Figure 39:
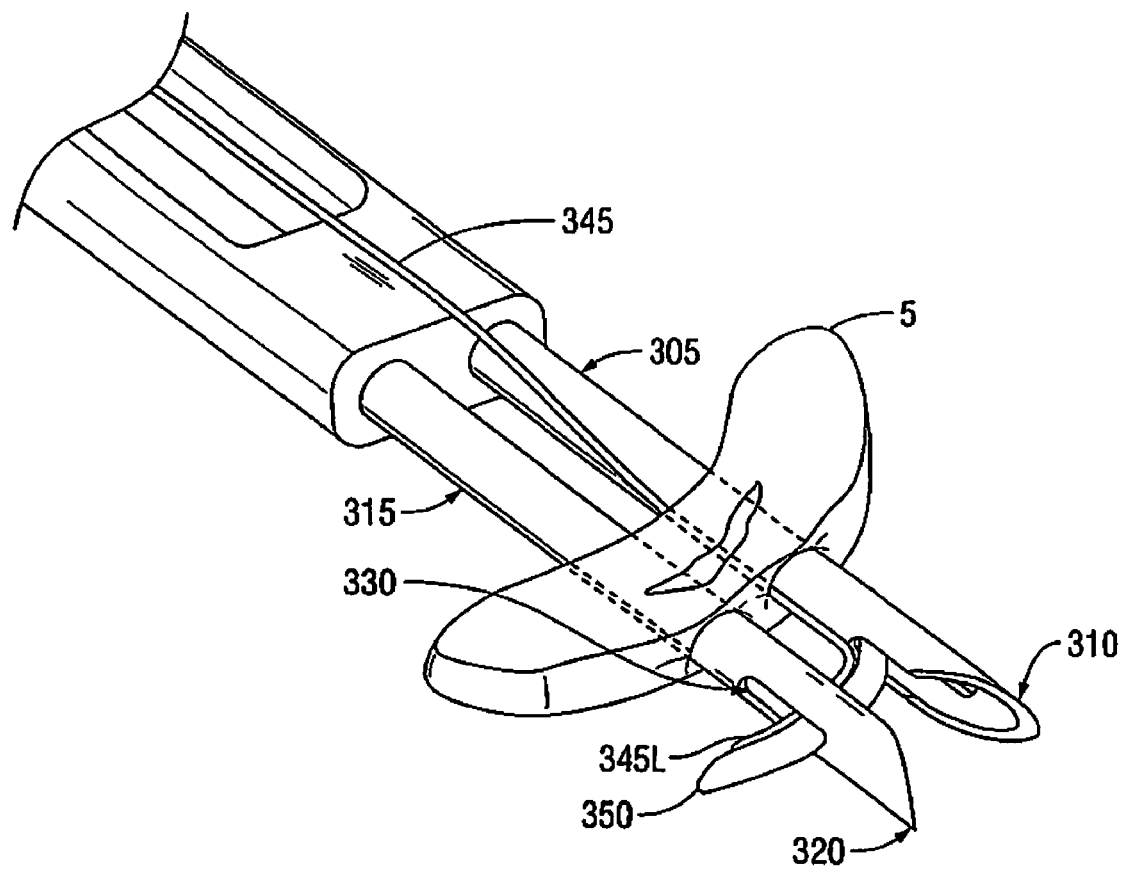

Next, as seen as FIGS. 38-39, a suture holder 350 carrying a suture 345 is advanced out distal end 310 of first needle 305. Suture holder 350 is configured so that the suture holder will carry the leading portion 345L of suture 345 through a slot 330 of second needle 315 when the suture holder is extended out of first needle 305.

Figure 40:
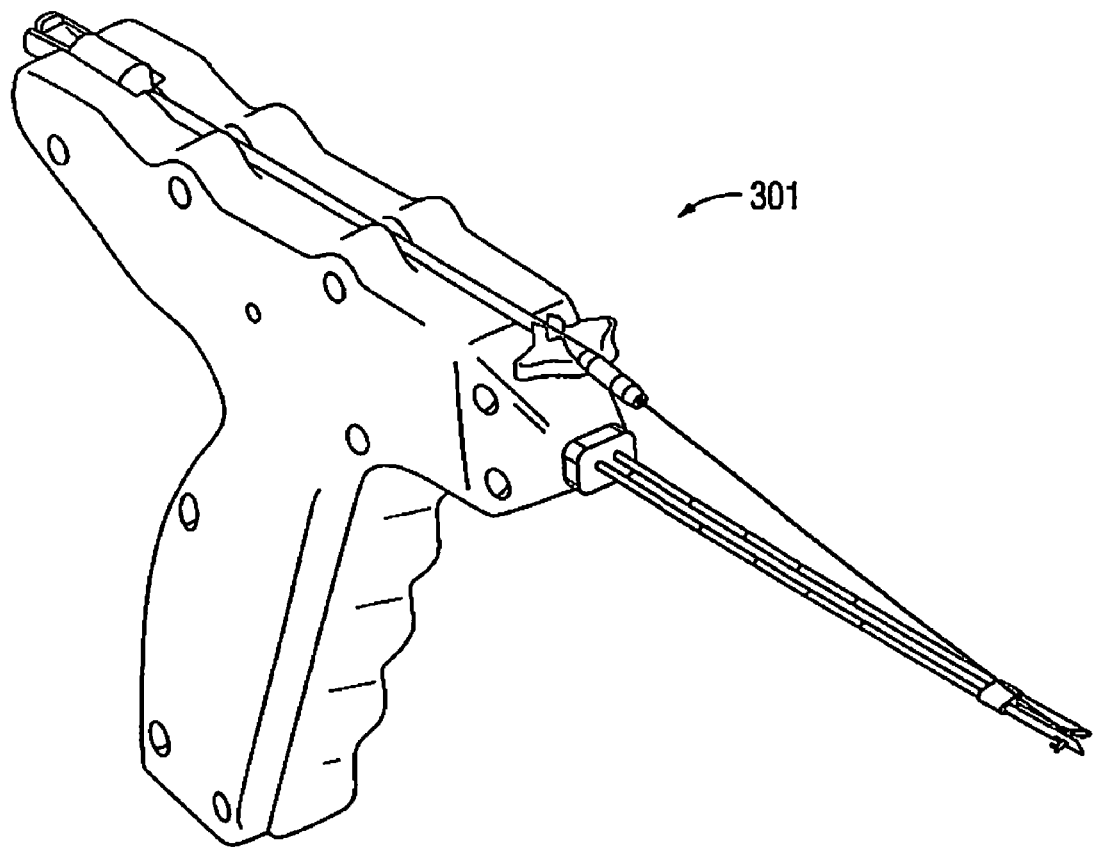
Figure 41:
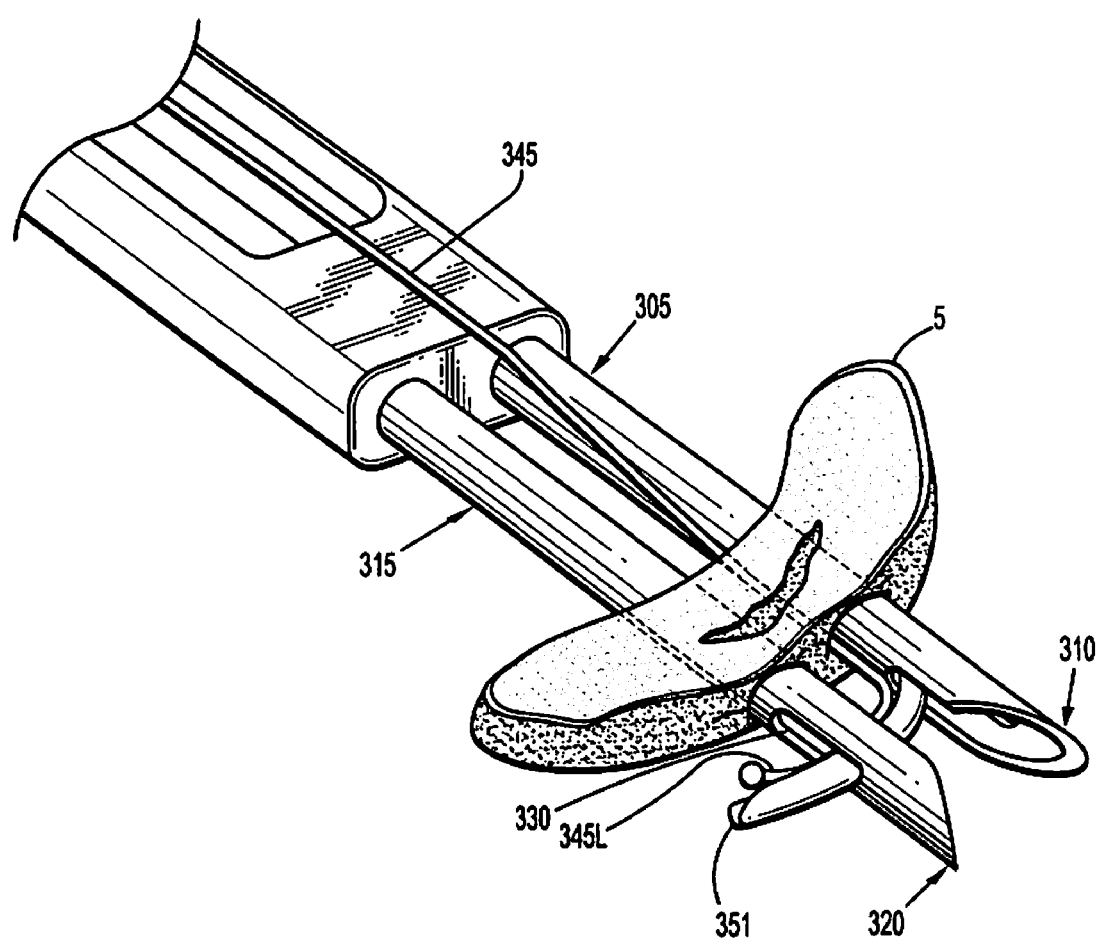

Then, as shown in FIGS. 40 and 41, an ejector wire 351 is used to eject leading portion 345L of suture 345 from suture holder 350.

Figure 42:
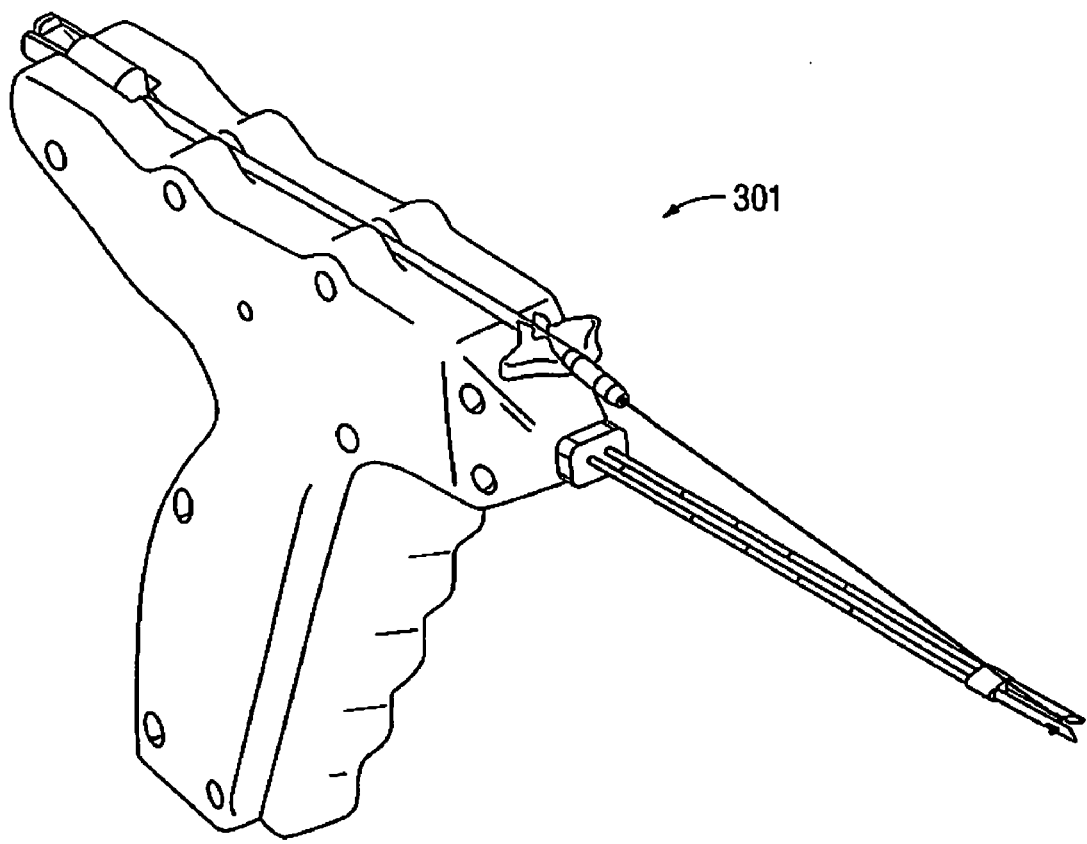
Figure 43:
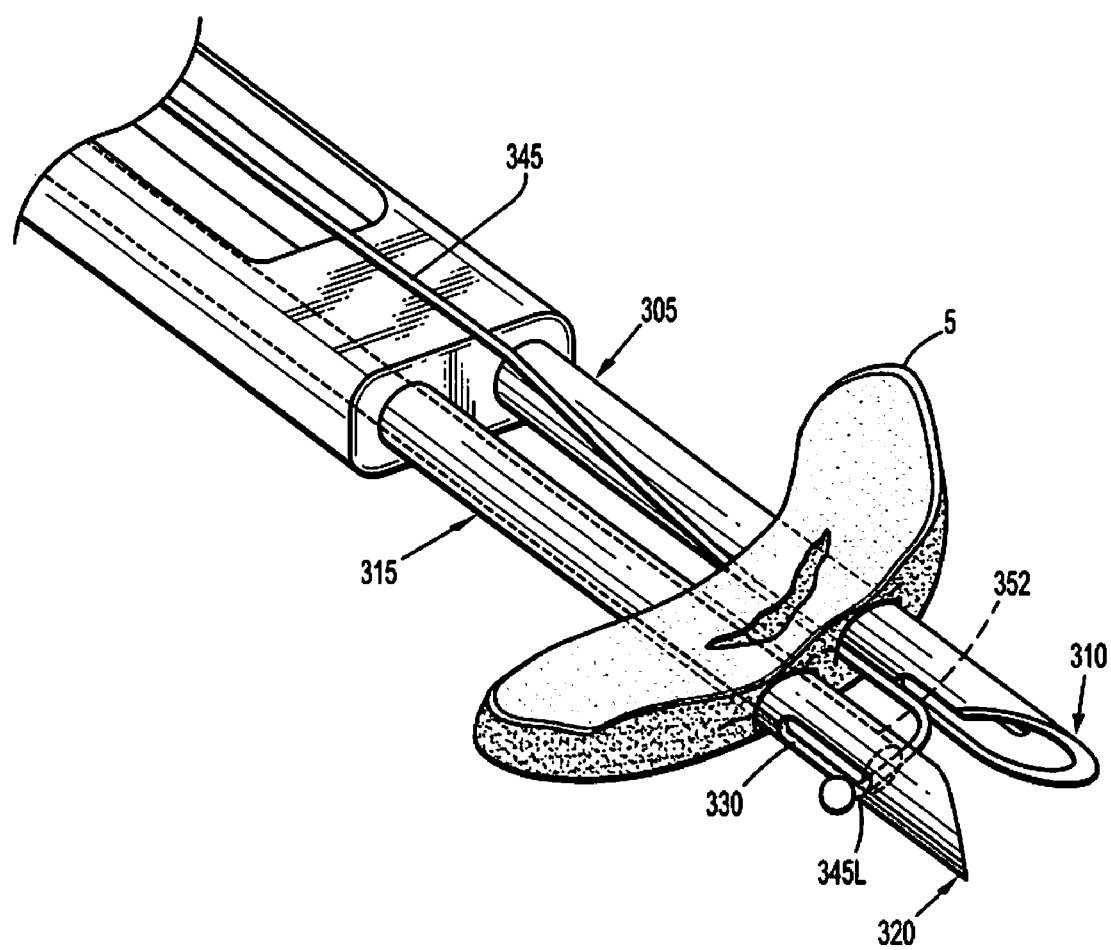

At this point, suture holder 350 is withdrawn, leaving leading portion 345L of suture 345 extending though slot 330 of second needle 315. See FIGS. 42 and 43. Then an obturator 352 is advanced within second needle 315 so as to pin leading portion 345L of suture 345 to second needle 315.

Figure 44:
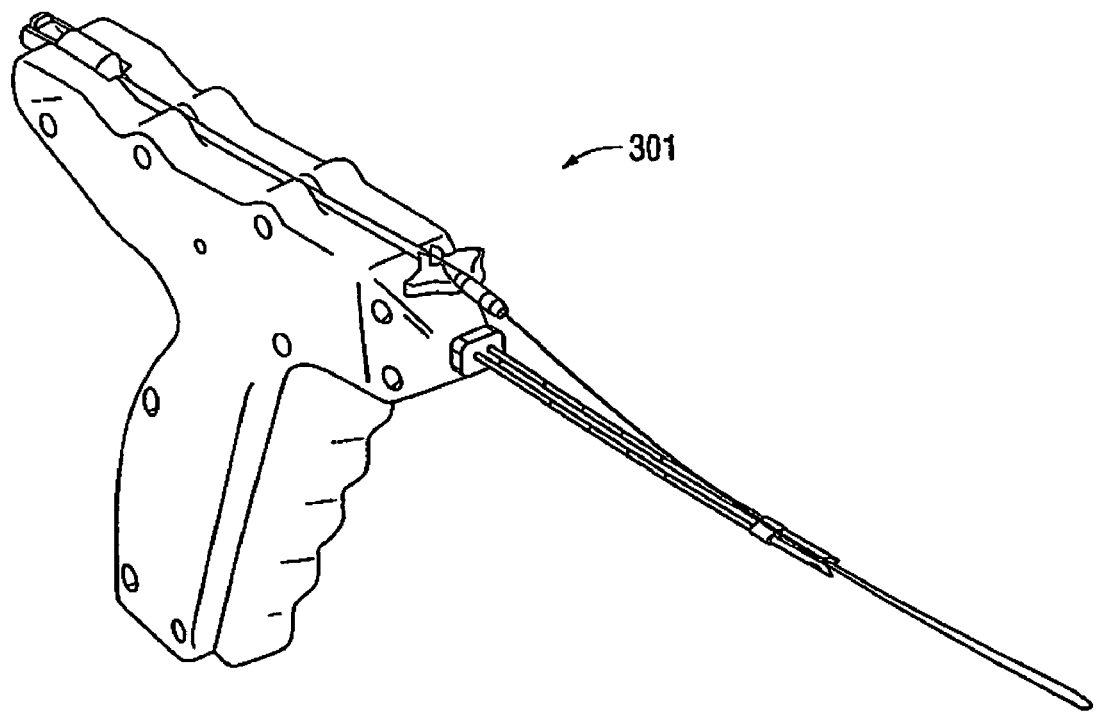
Figure 45:
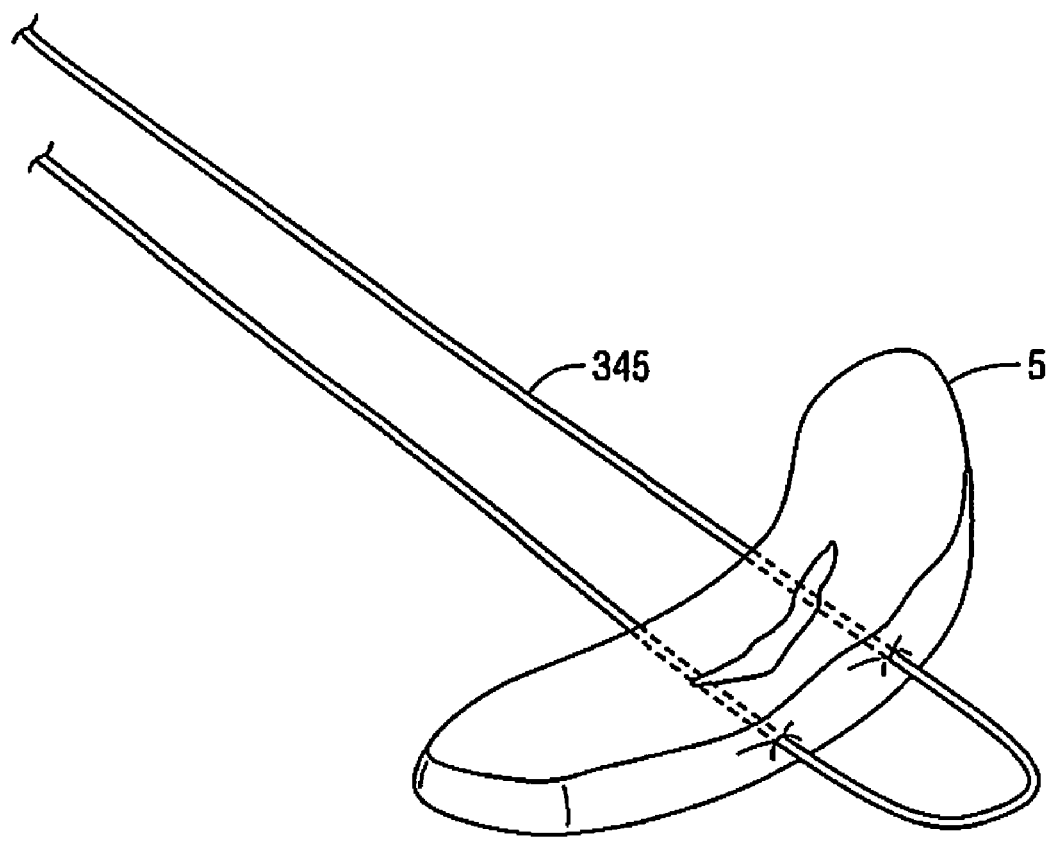

Next, suture passer 301 is retracted so that its first needle 305 and second needle 315 are withdrawn from the meniscus. See FIGS. 44 and 45. Thus, at this point in the procedure, suture 345 will have been passed from the near side of the meniscus, through the meniscus and then back again. Significantly, by appropriately positioning first needle 305 and second needle 315 during the suture passing operation, suture 345 will extend across tear 20 formed in meniscus 5.

Figure 46:
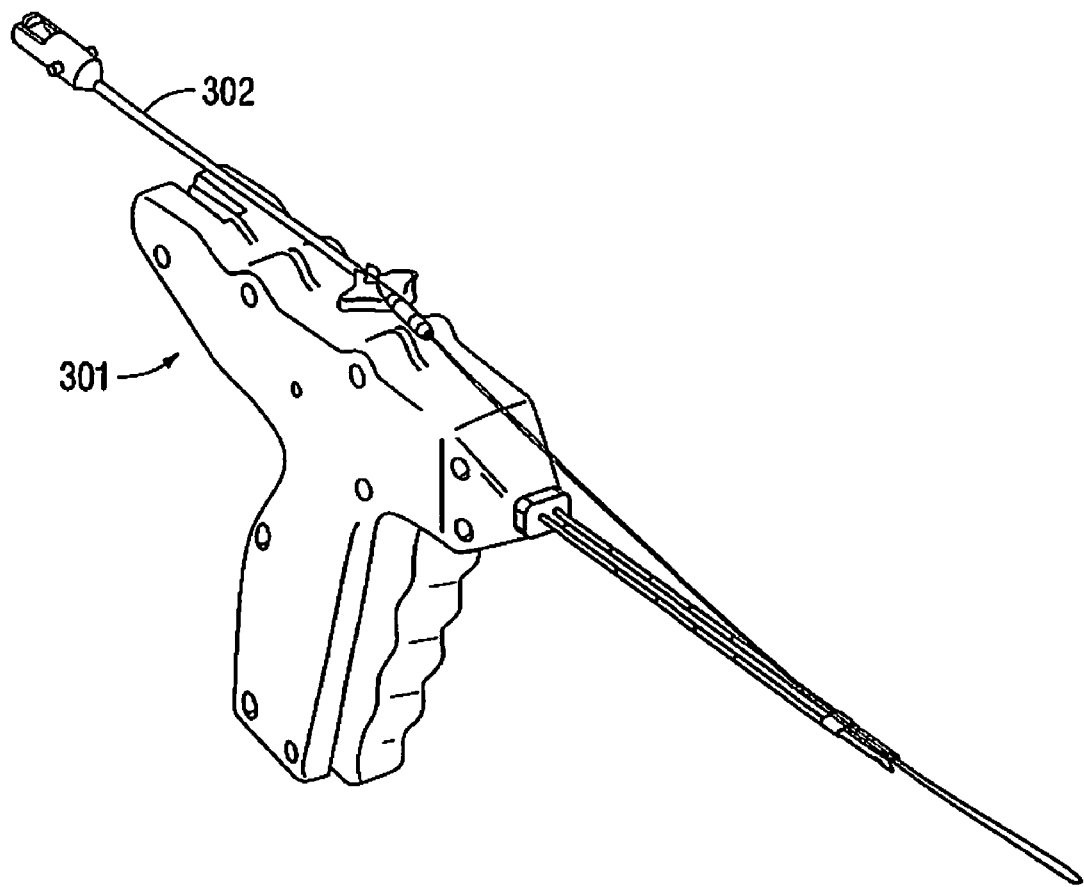
Figure 47:
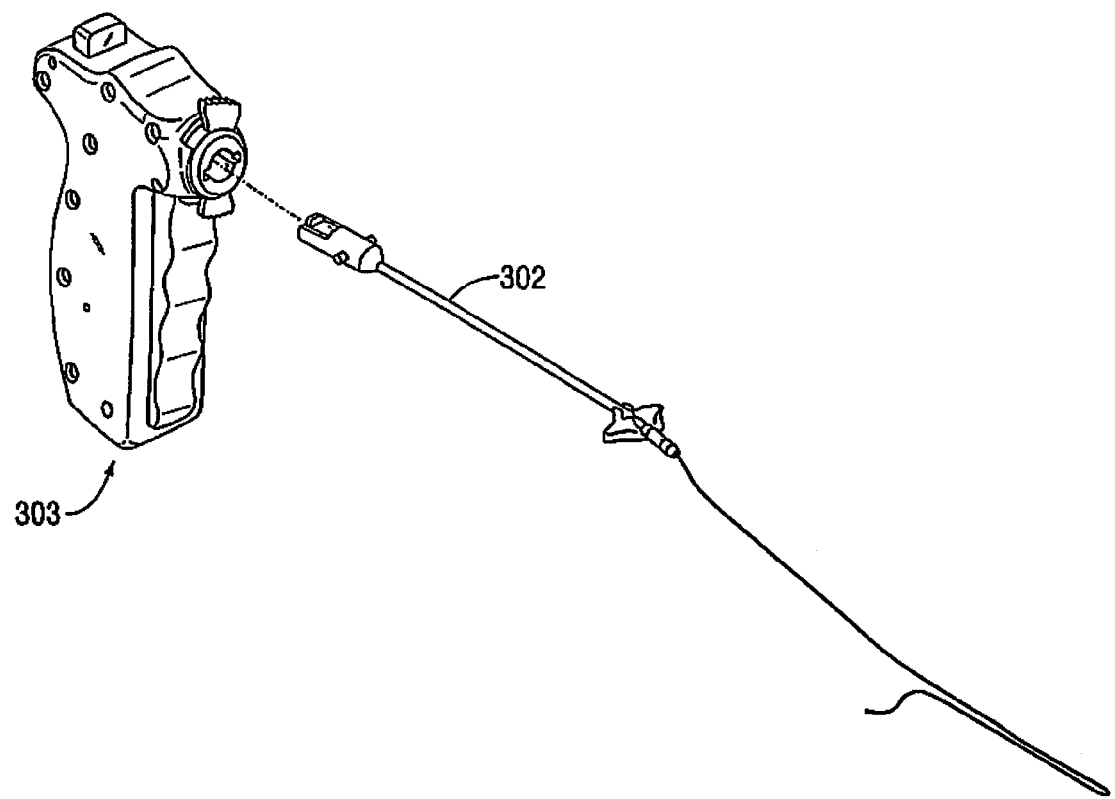
Figure 48:
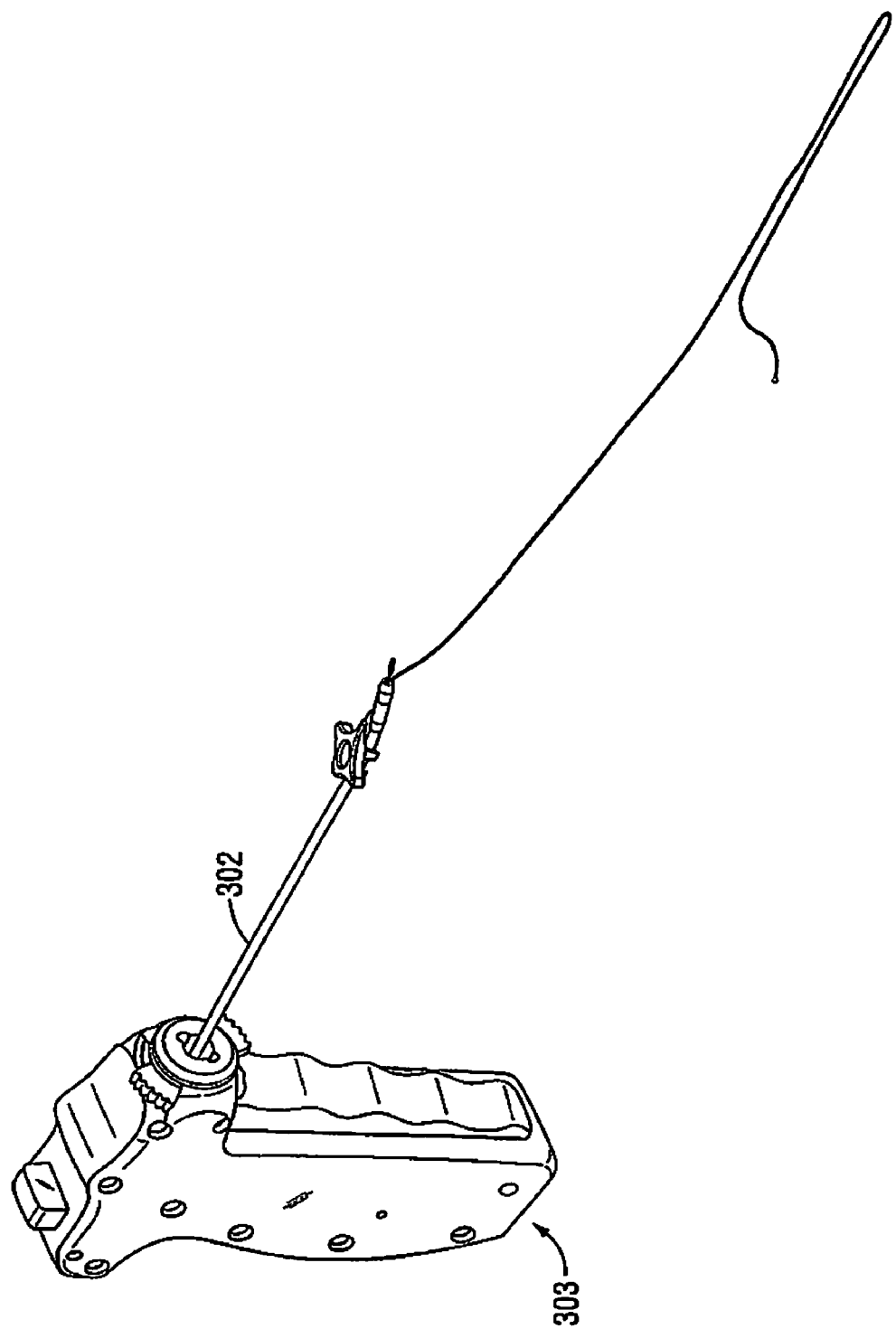
Figure 49:
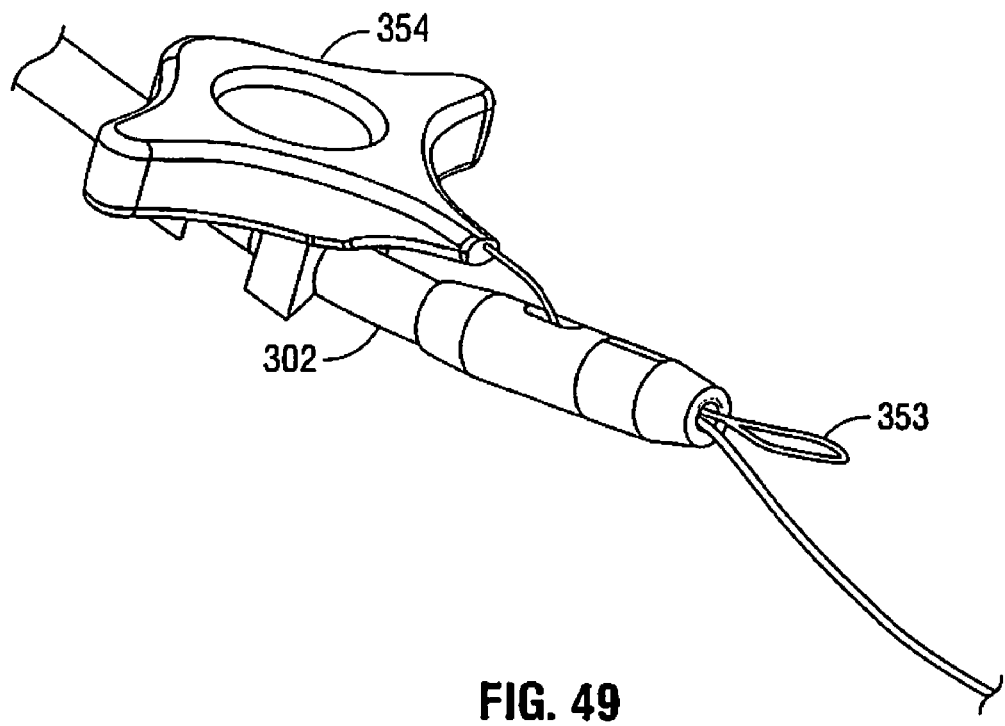
Figure 50:
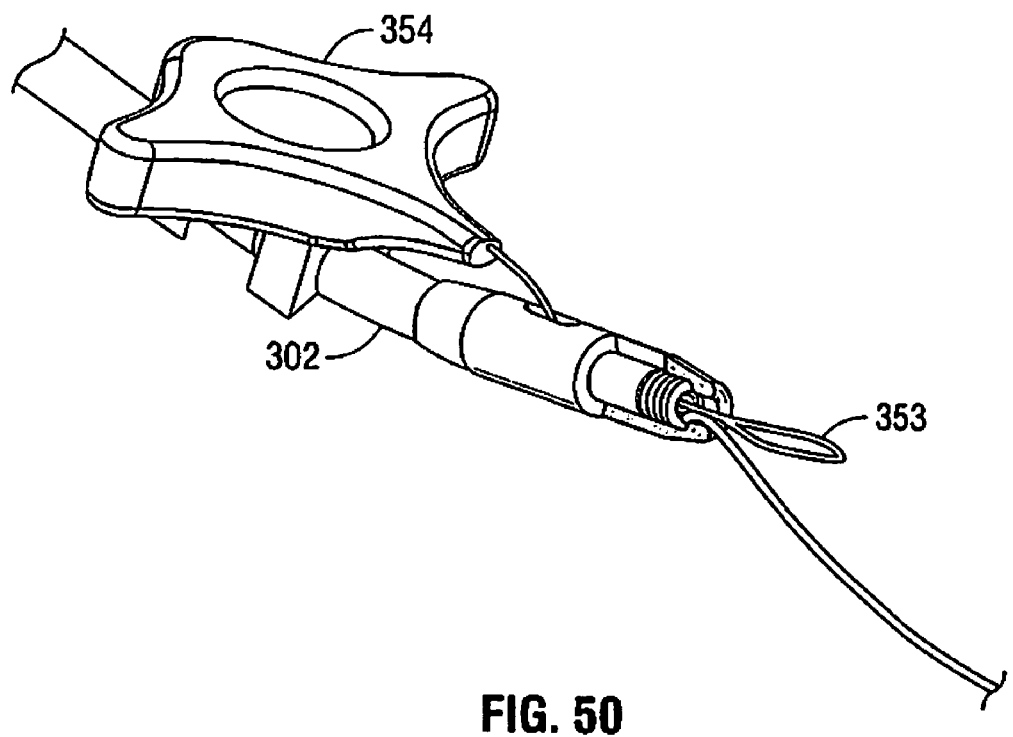
Figure 51:
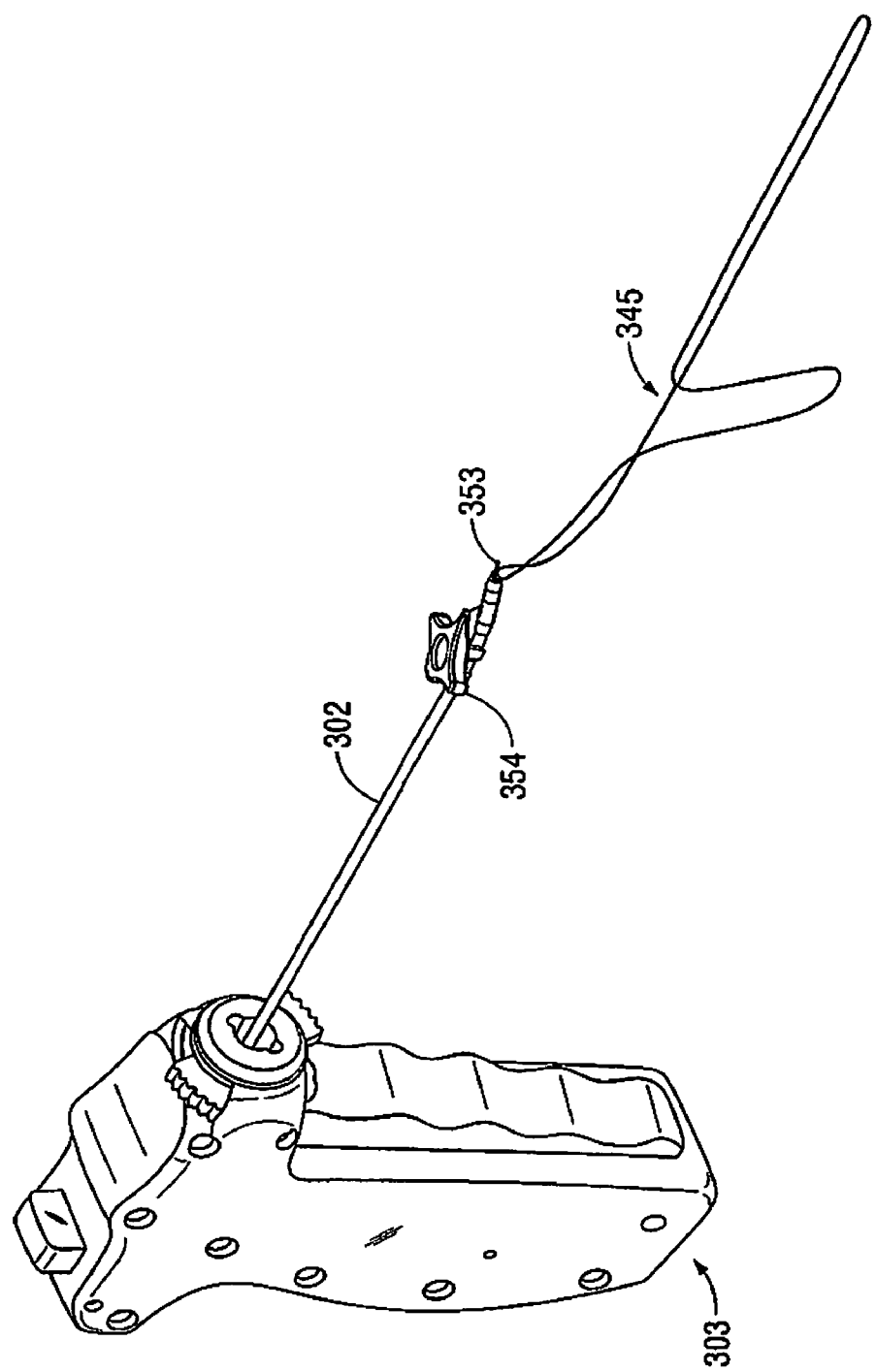
Figure 52:
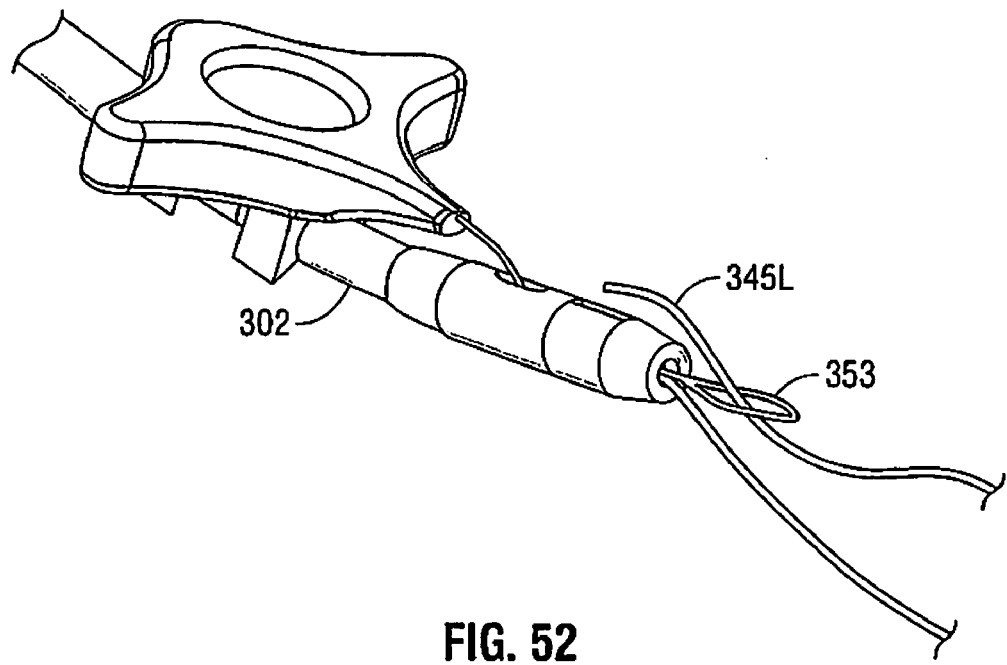
Figure 53:
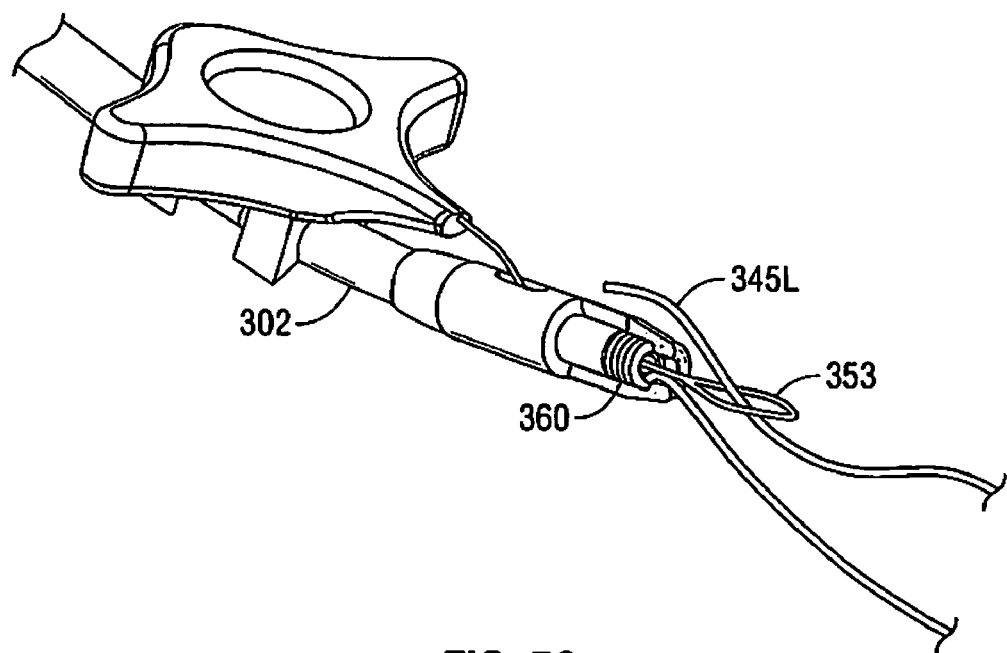
Figure 54:
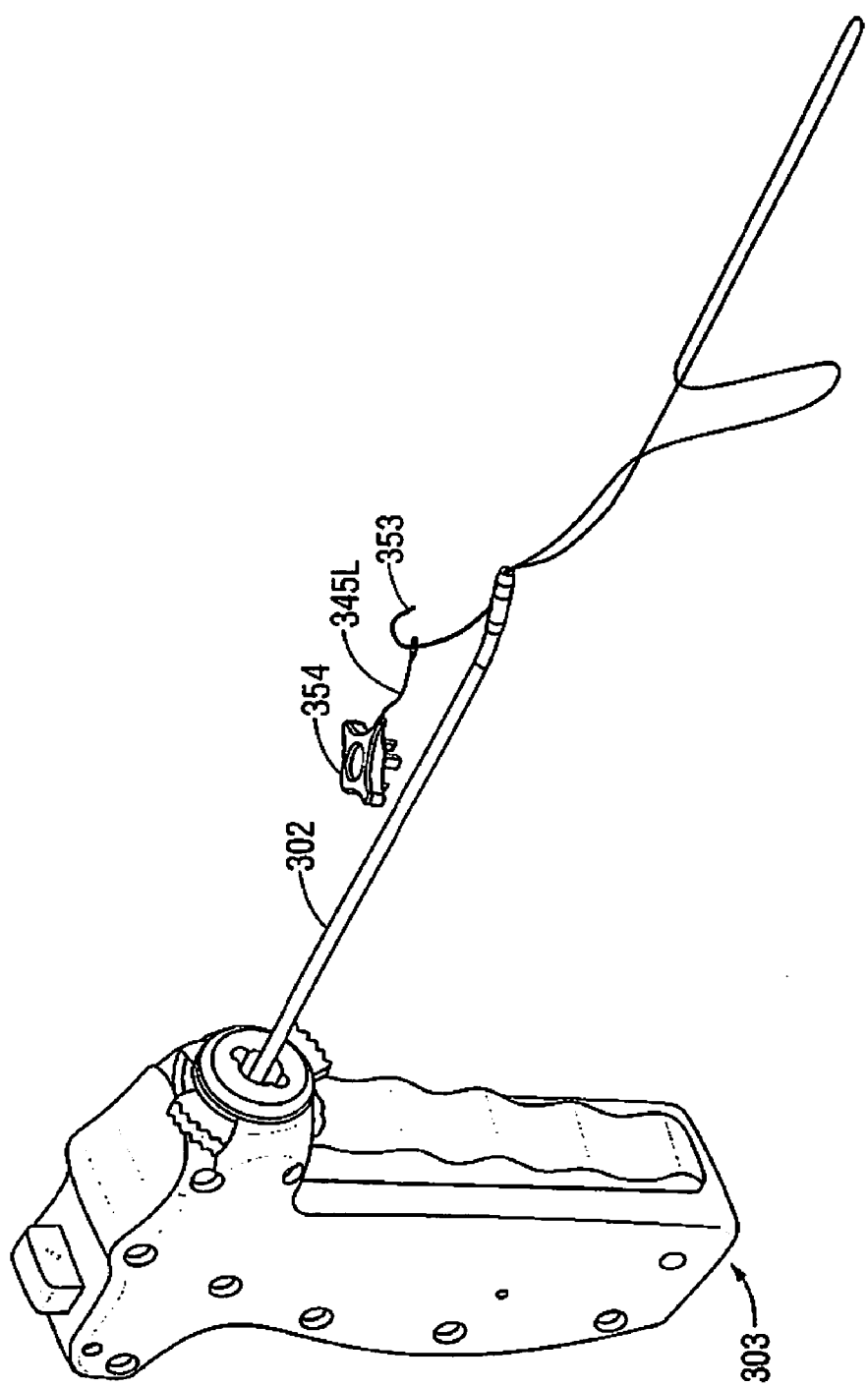
Figure 55:
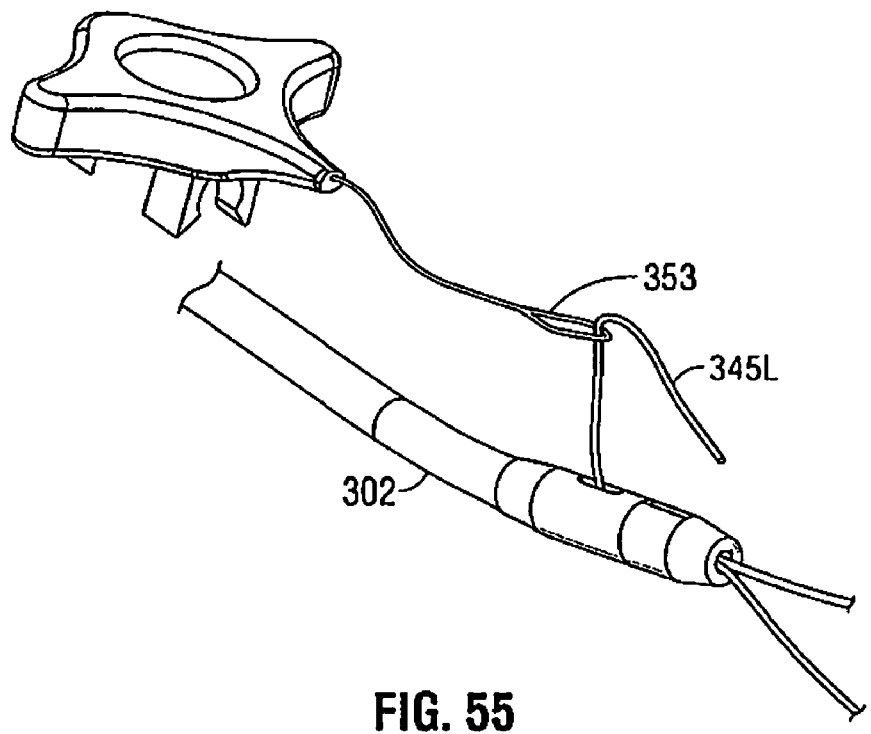
Figure 56:
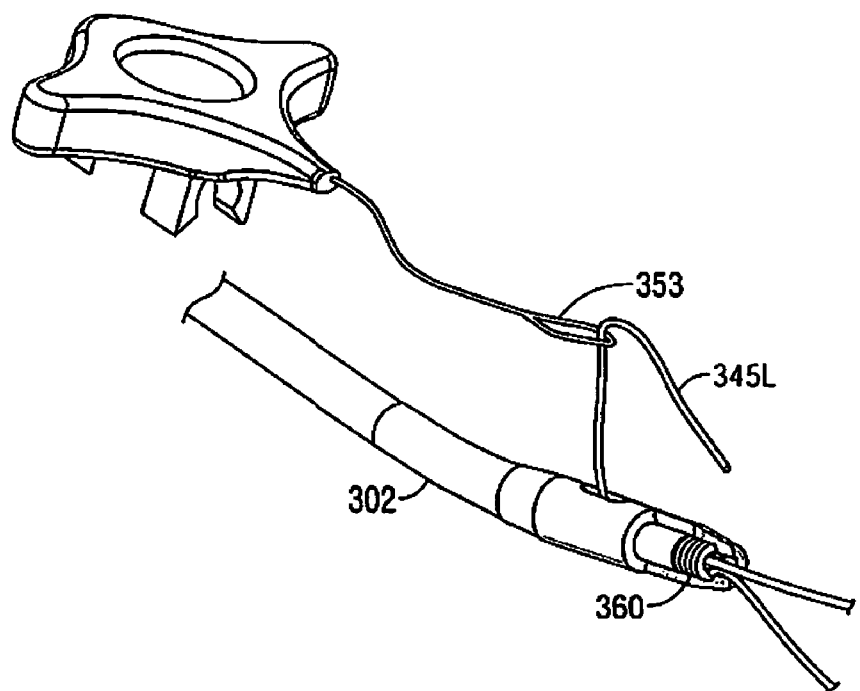

Next, the suture is tied down so as to close the tear in the meniscus. This may be done in a variety of ways which will be apparent to those skilled in the art in view of the present disclosure. In one preferred form of the invention, this is accomplished in the following way. First, as shown in FIG. 46, suture cartridge 302 is dismounted from suture passer 301. Then suture cartridge 302 is mounted to knot pusher/cutter 303 (FIG. 47) and locked in place (FIG. 48). At this point, and looking now at FIGS. 49 and 50, suture cartridge 302 is ready to receive leading portion 345L of suture 345. Next, leading portion 345L of suture 345 is inserted into a loop 353 of a snare basket 354, as shown in FIGS. 51-53. Snare basket 354 essentially comprises a conventional suture threader component, or needle threader component, in the sense that a collapsible loop is formed at the end of a pullable tab. Then snare basket 354 is retracted, carrying leading portion 345L of suture 345 through a pre-formed, uncinched knot 360 formed in the trailing portion 345T of suture 345 and disposed at the tip of knot pusher/cutter 303. See FIGS. 54-56. It will be appreciated that as snare basket 354 carries leading portion 345L of suture 345 through pre-formed, uncinched knot 360, the suture passes back through itself.

Figure 57:
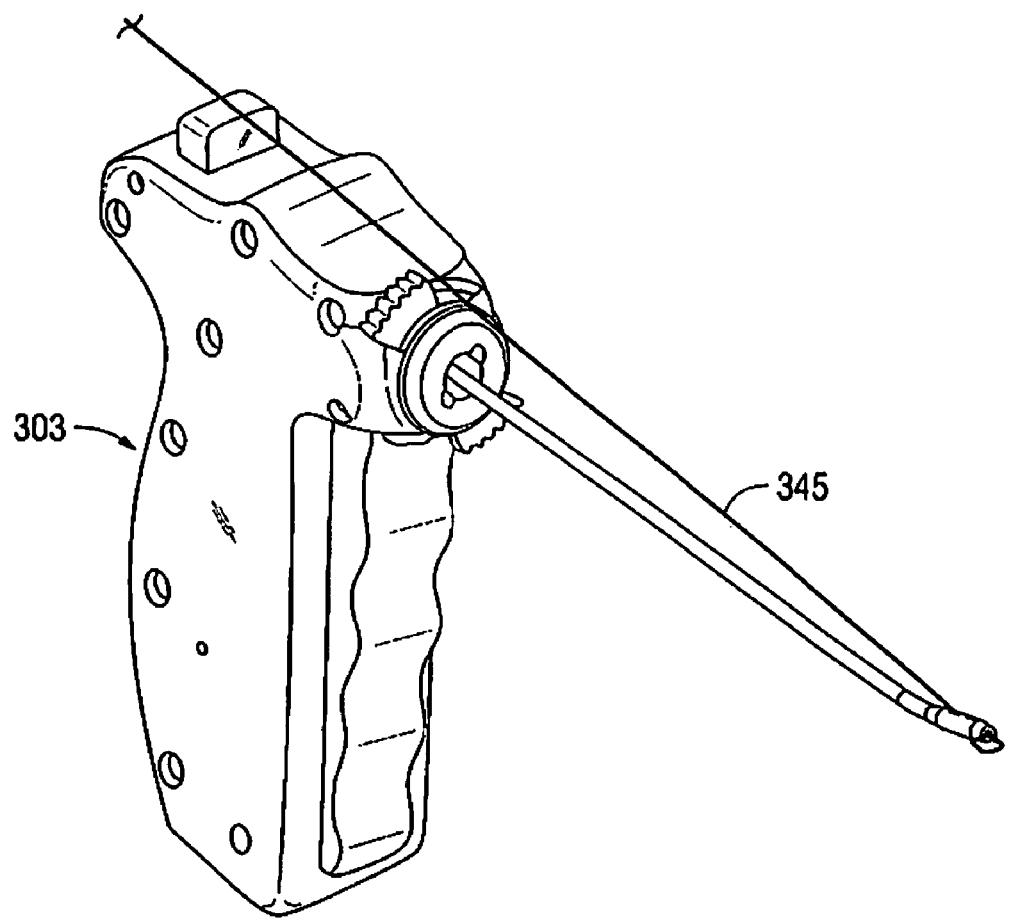
Figure 58:
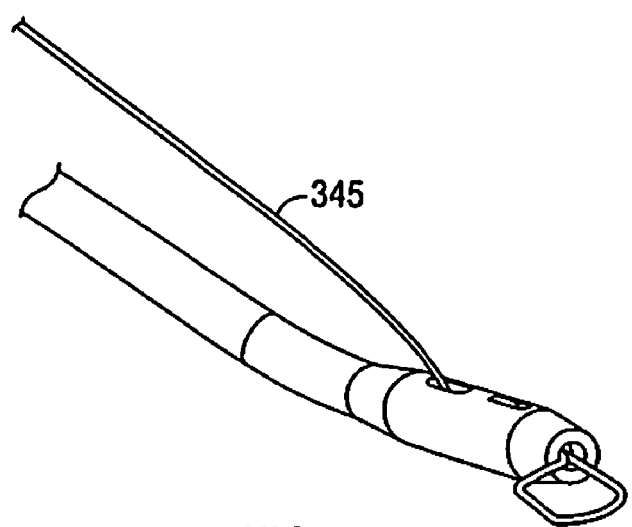
Figure 59:
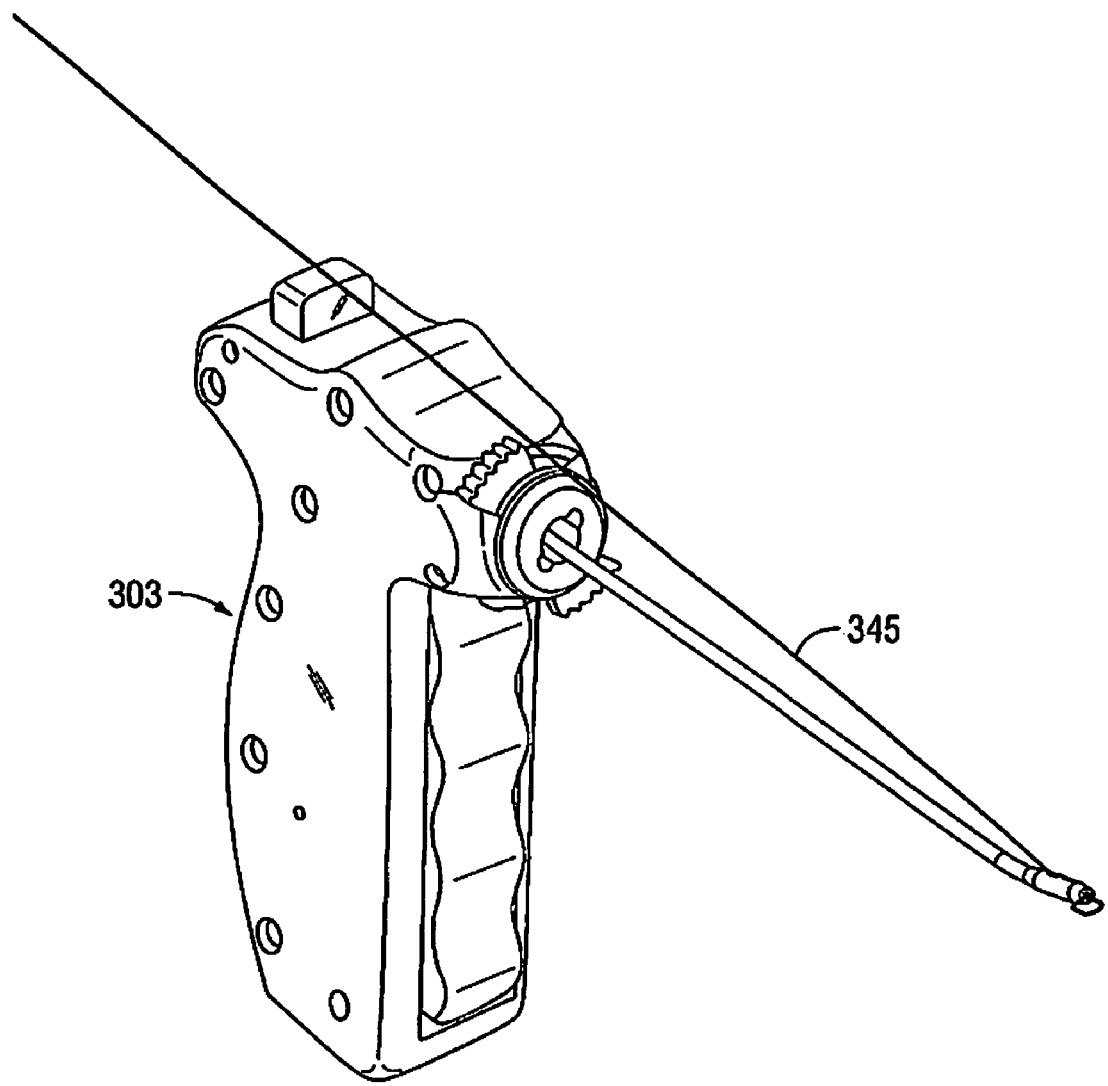
Figure 60:
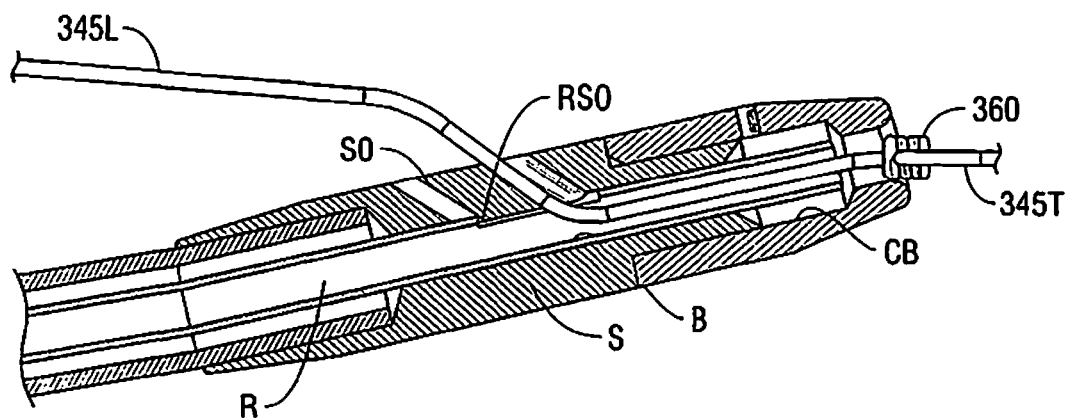
Figure 61:
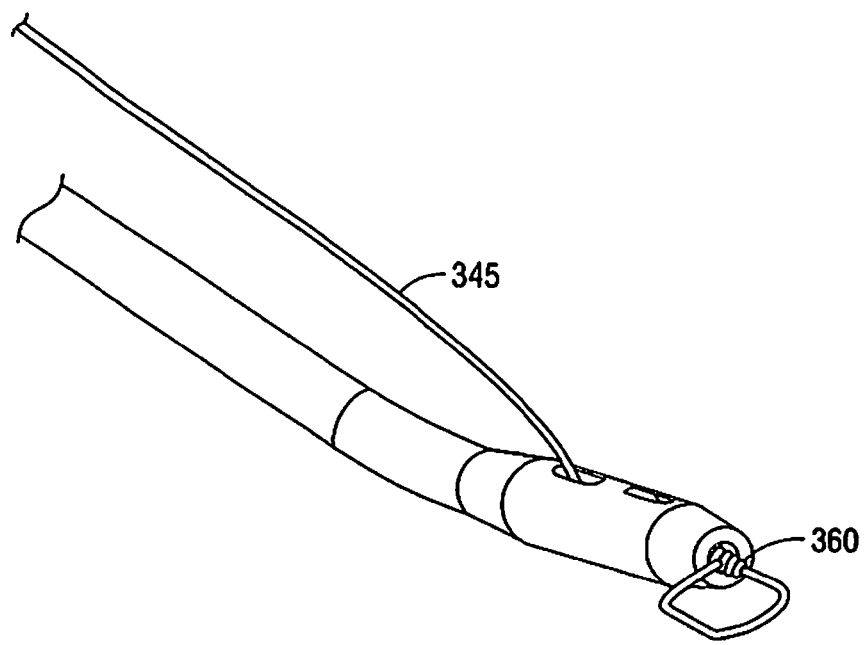
Figure 62:
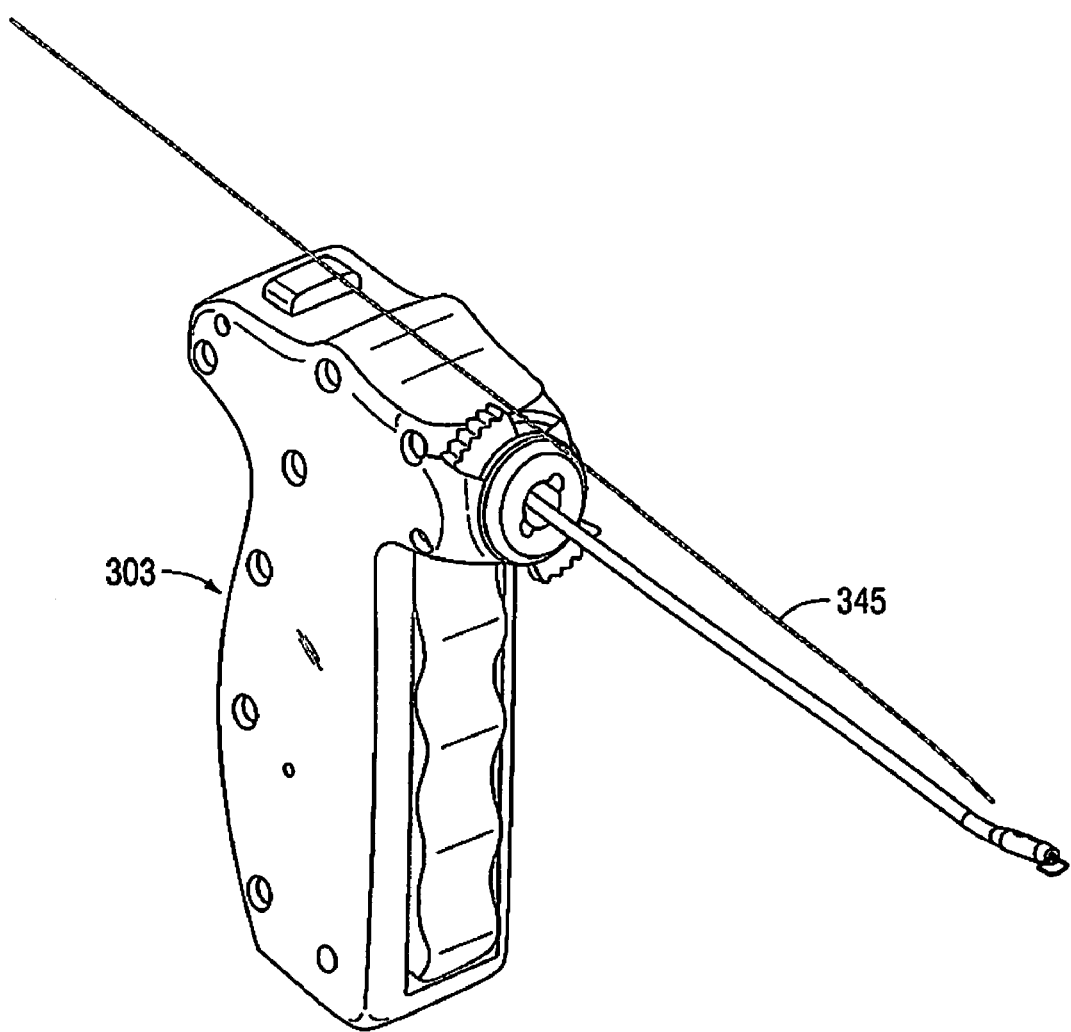
Figure 63:
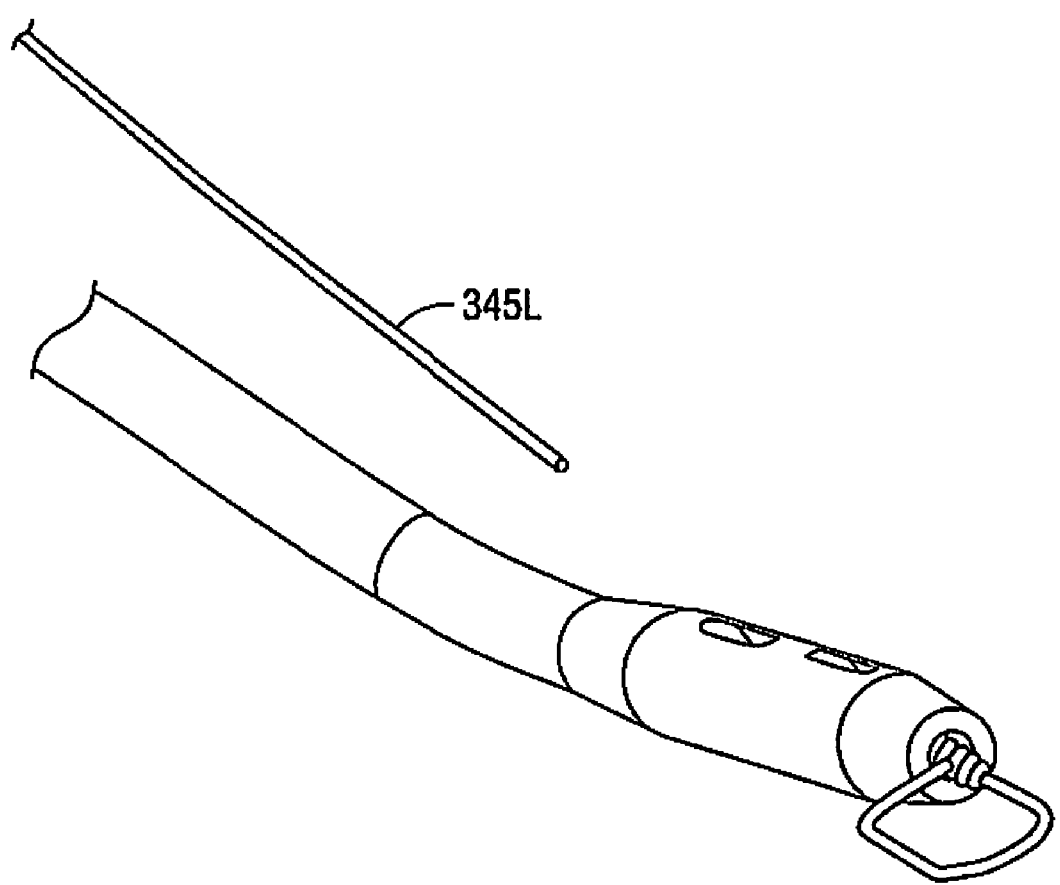
Figure 64:
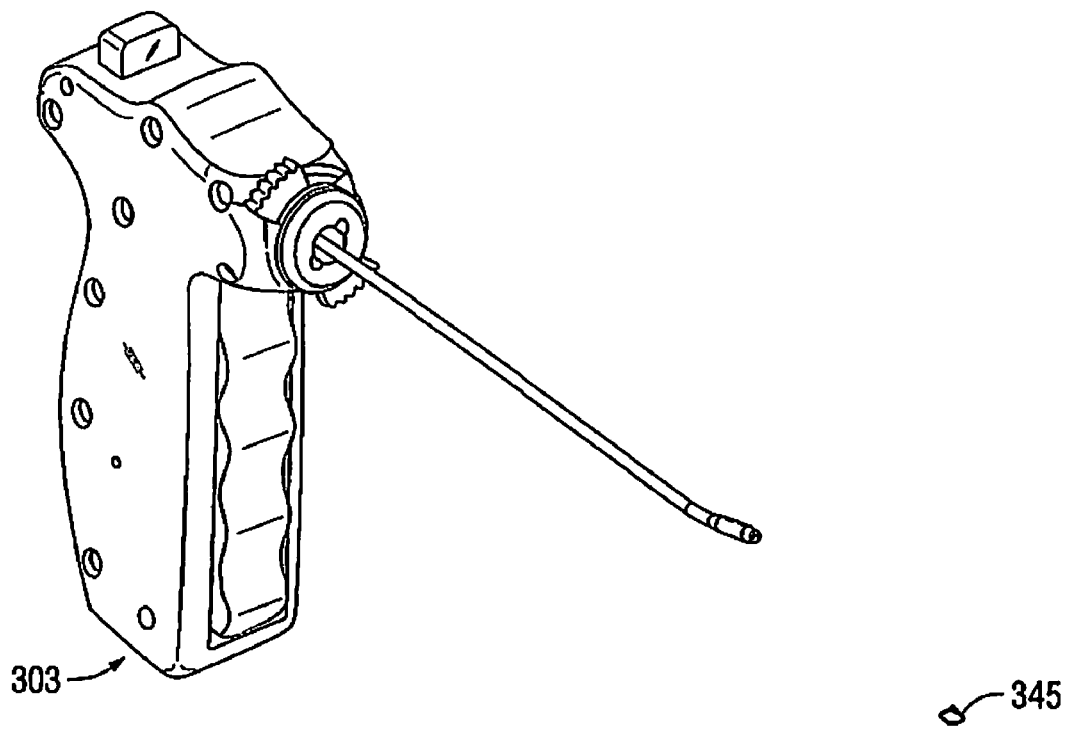
Figure 65:
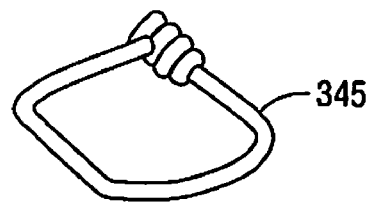

Then, and looking now at FIGS. 57-59, knot pusher/cutter 303 is advanced distally so as to bring pre-formed, un-cinched knot 360 to the near side surface of the meniscus. Next, as shown in FIGS. 60 and 61, pre-formed, un-cinched knot 360 is tightened. Then leading portion 345L of suture 345 is trimmed away by knot pusher/cutter 303 (FIGS. 62 and 63). Finally, knot pusher/cutter 303 is removed, leaving suture 345 closing the tear in the meniscus (FIGS. 64 and 65) with a low-profile suture fixation.

In one preferred form of the invention, and looking now at FIG. 60, knot pusher/cutter 303 comprises a shaft S having a central bore B, a counterbore CB and a side opening SO. A hollow ram R, having a ram side opening RSO, is slidably disposed within bore B of shaft S. Prior to knot deployment, the pre-formed, uncinched knot 360 is seated within counterbore CB; and after leading portion 345L of suture 345 is passed through pre-formed, uncinched knot 360, leading portion 345L is drawn through ram side opening RSO and shaft side opening SO; and when the knot is to be separated from shaft S, ram R is moved distally, first pushing the knot out of the shaft and, after cinching, thereafter cutting leading portion 345L of suture 345 by virtue of moving side opening SO out of alignment with ram side opening RSO.

In one preferred form of the invention, the cinched knot is separated from shaft S in a first discrete step, and then the suture is cut in a second discrete step.

Fourth Preferred Method and Apparatus

Figure 66:
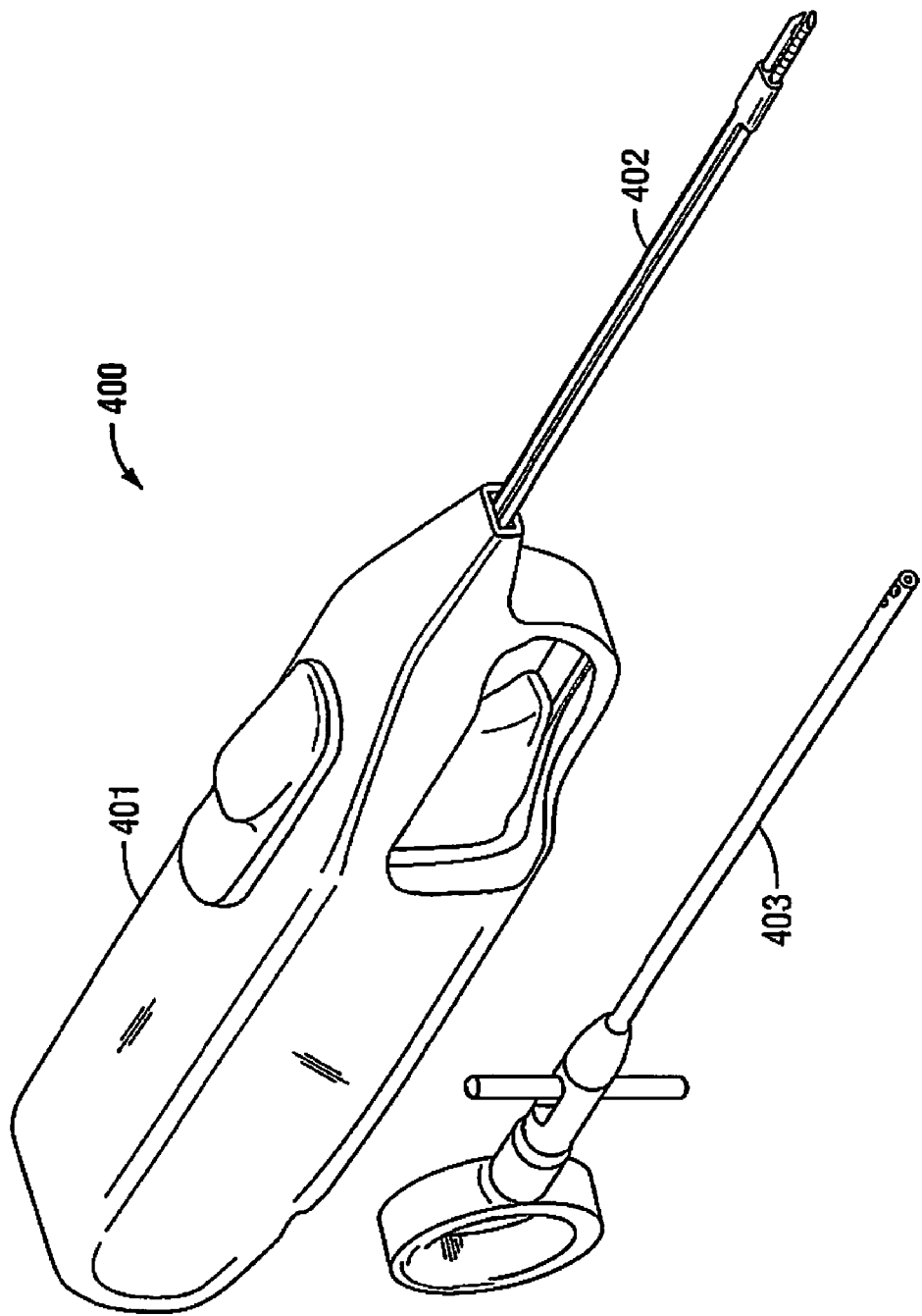
FIGS. 66-91 are a series of views showing a fourth method and apparatus for repairing a meniscal tear, with the meniscus being omitted from selected views in order to simplify the drawing and enhance comprehension.

Looking now at FIG. 66, there is shown an apparatus 400 for use in closing tear 20 in meniscus 5. Apparatus 400 generally comprises a handle 401, a needle cartridge 402 and a pusher/cutter 403. Pusher/cutter 403 is similar to suture cartridge 302 discussed above, in the sense that it carries a pre-formed, uncinched knot, etc., as will hereinafter be discussed. Specific details of the construction and function of handle 401, needle cartridge 402 and pusher/cutter 403 will be disclosed in the course of the following discussion of using apparatus 400 to close tear 20 in meniscus 5.

Figure 67:
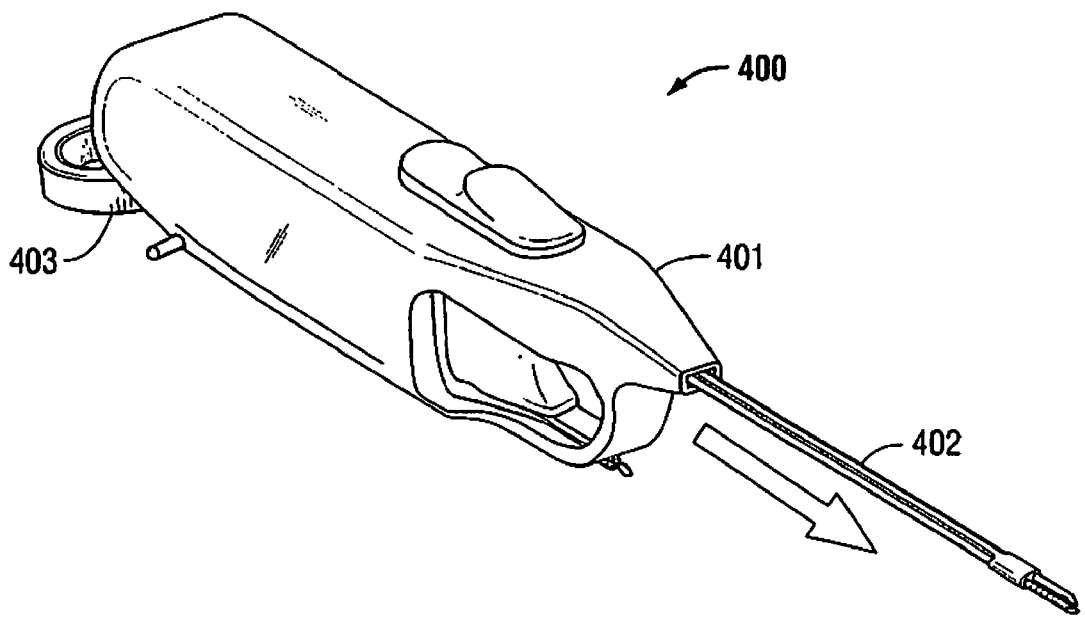
Figure 68:
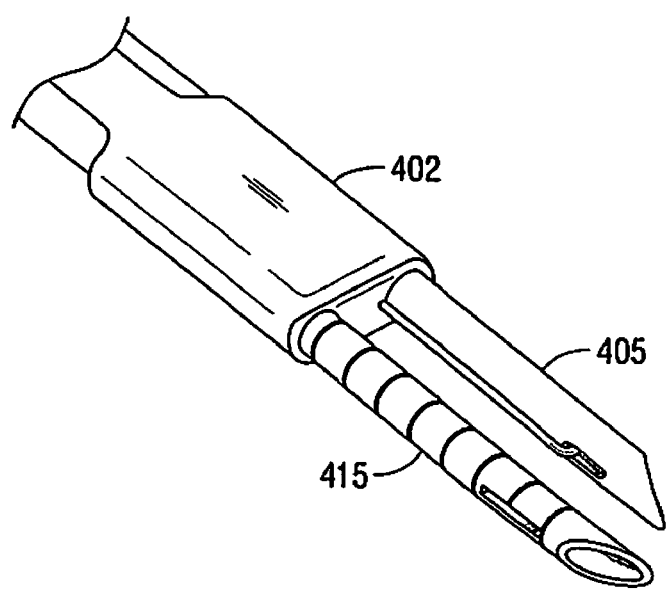

Looking now at FIGS. 67 and 68, apparatus 400 is manipulated so that its first needle 405 and its second needle 415 are advanced so that their distal tips 410, 420 are passed completely through meniscus 5.

Figure 69:
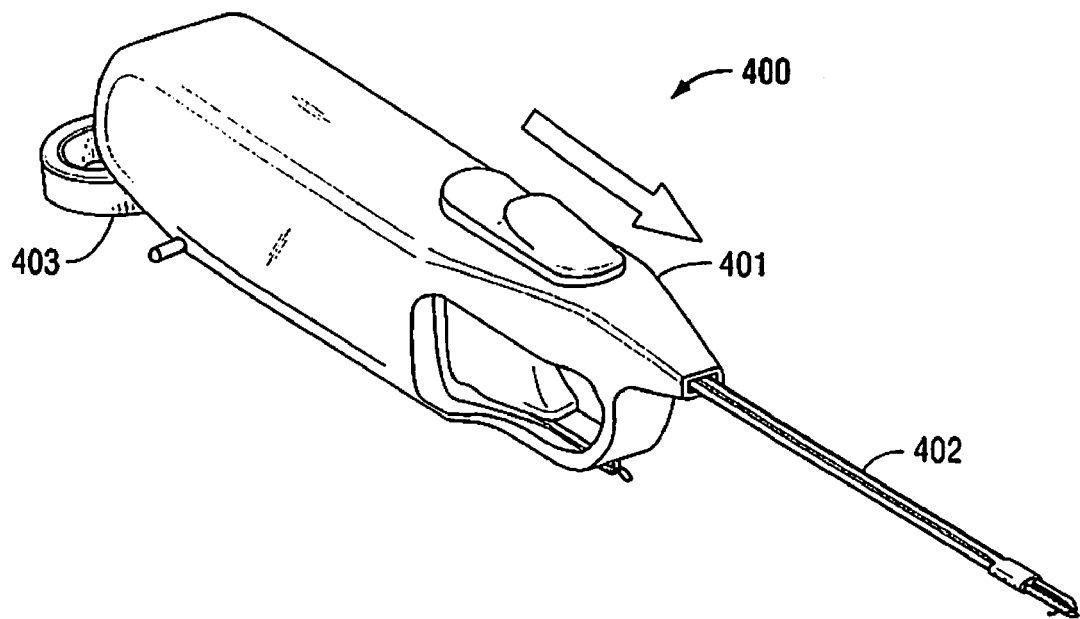
Figure 70:
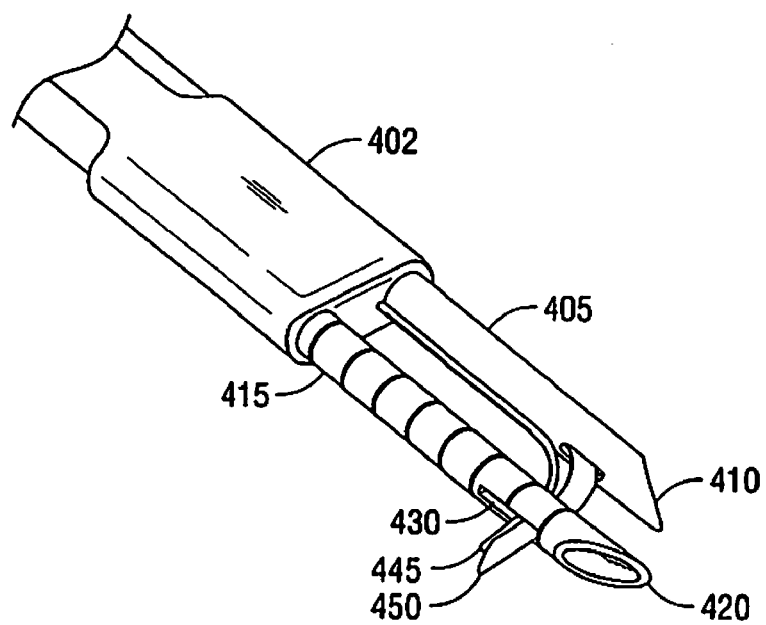

Next, as seen as FIGS. 69 and 70, a suture holder 450 carrying a suture 445 is advanced out distal end 410 of first needle 405. Suture holder 450 is configured so that the suture holder will carry the leading portion 445L of suture 445 through a slot 430 of second needle 415 when the suture holder is extended out of first needle 405.

Figure 71:
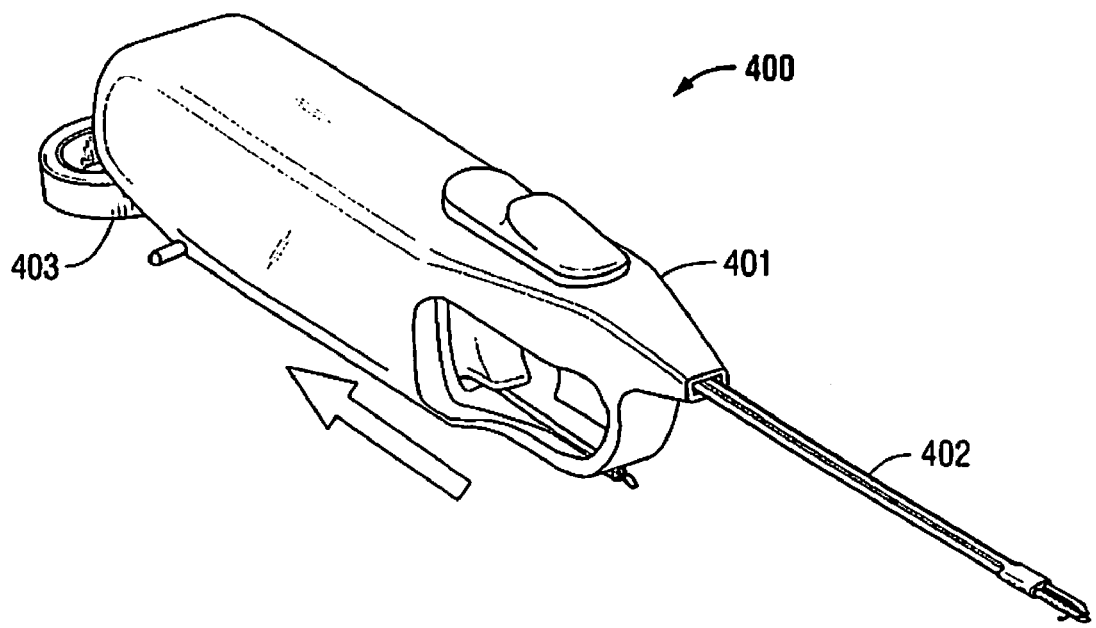
Figure 72:
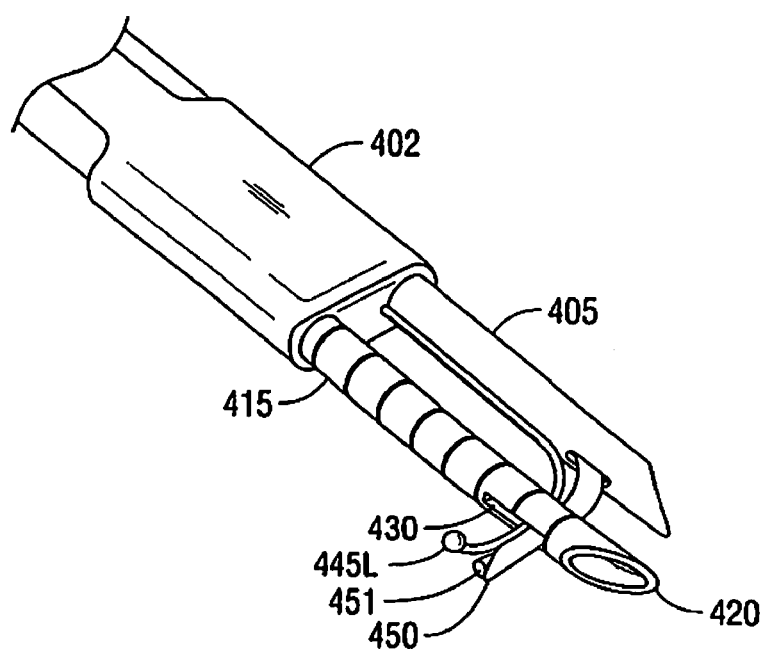

Then, as shown in FIGS. 71 and 72, an ejector wire 451 is used to eject leading portion 445L of suture 445 from suture holder 450.

Figure 73:
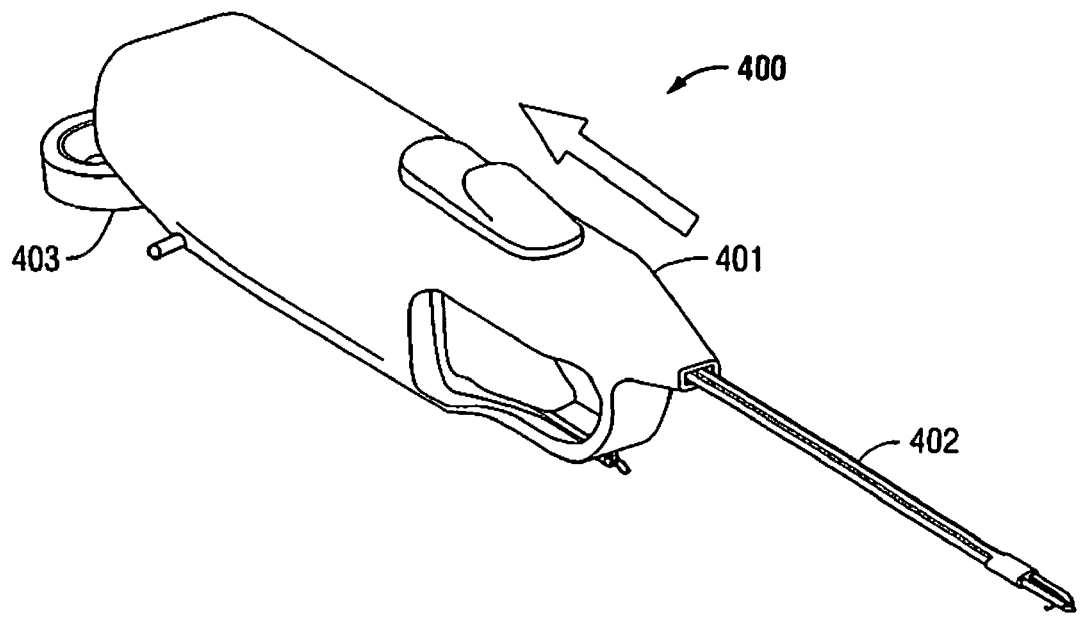
Figure 74:
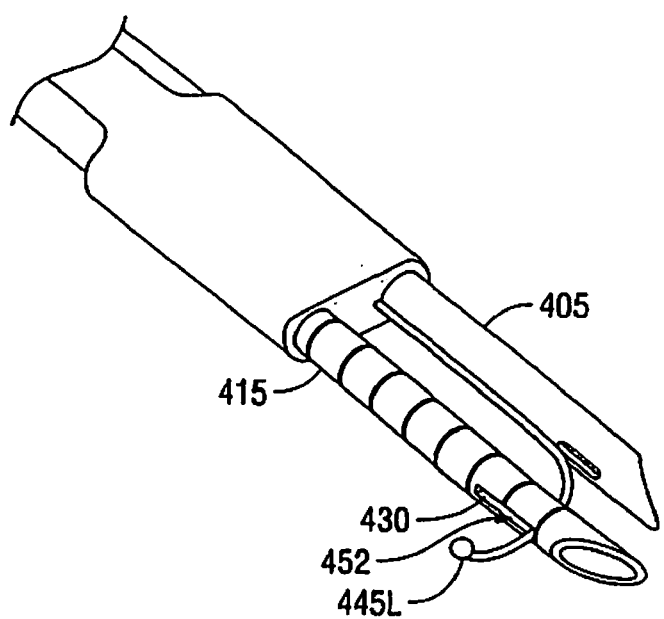

At this point, suture holder 450 is withdrawn, leaving leading portion 445L of suture 445 extending though slot 430 of second needle 415. See FIGS. 73 and 74. Then an obturator 452 is advanced within second needle 415 so as to pin leading portion 445L of suture 445 to second needle 415.

Figure 75:
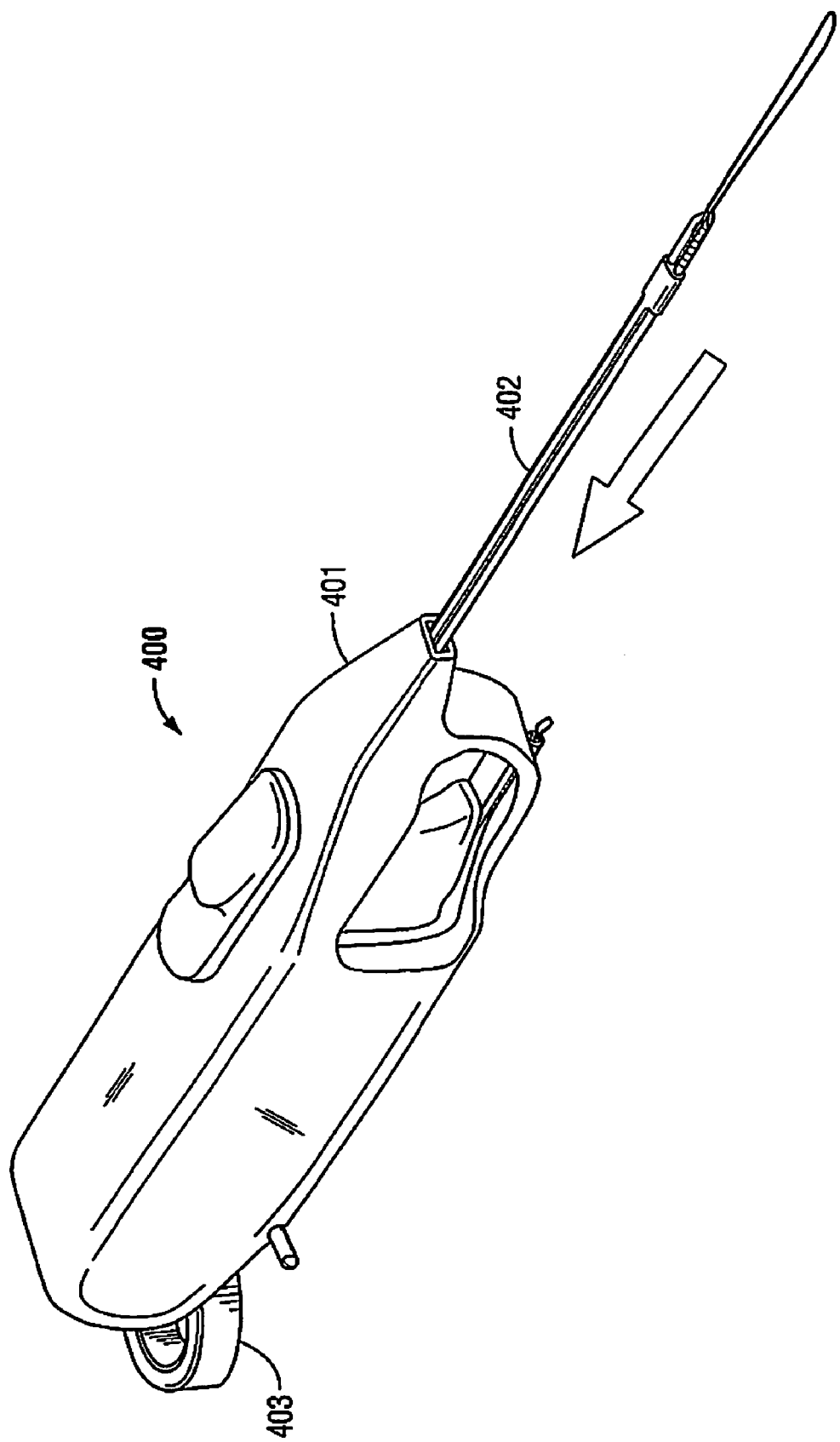

Next, handle 401 is retracted so that its first needle 405 and second needle 415 are withdrawn from the meniscus. See FIG. 75. Thus, at this point in the procedure, suture 445 will have been passed from the near side of the meniscus, through the meniscus and then back again. Significantly, by appropriately positioning first needle 405 and second needle 415 during the suture passing operation, suture 445 will extend across tear 20 formed in meniscus 5.

Figure 76:
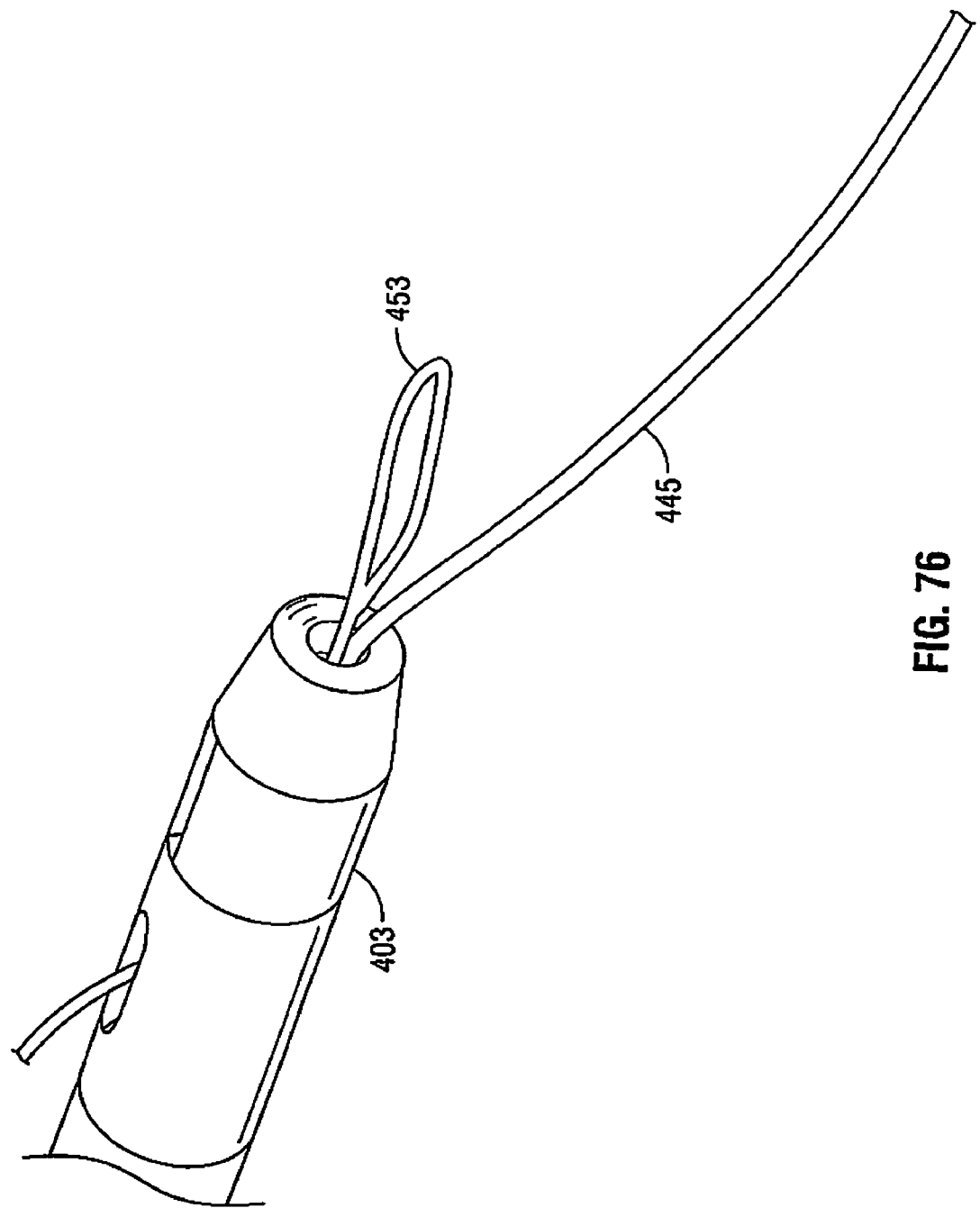
Figure 77:
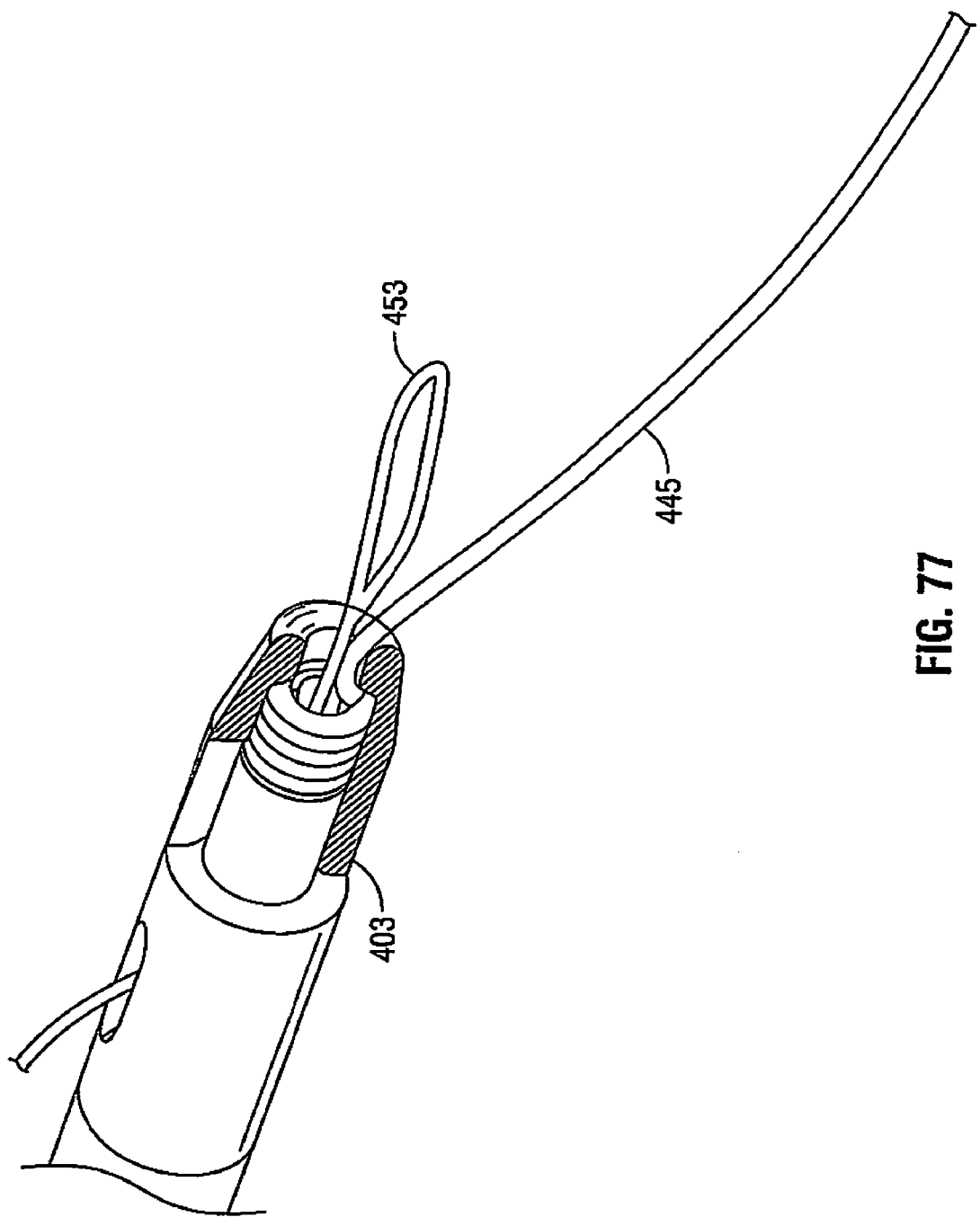
Figure 78:
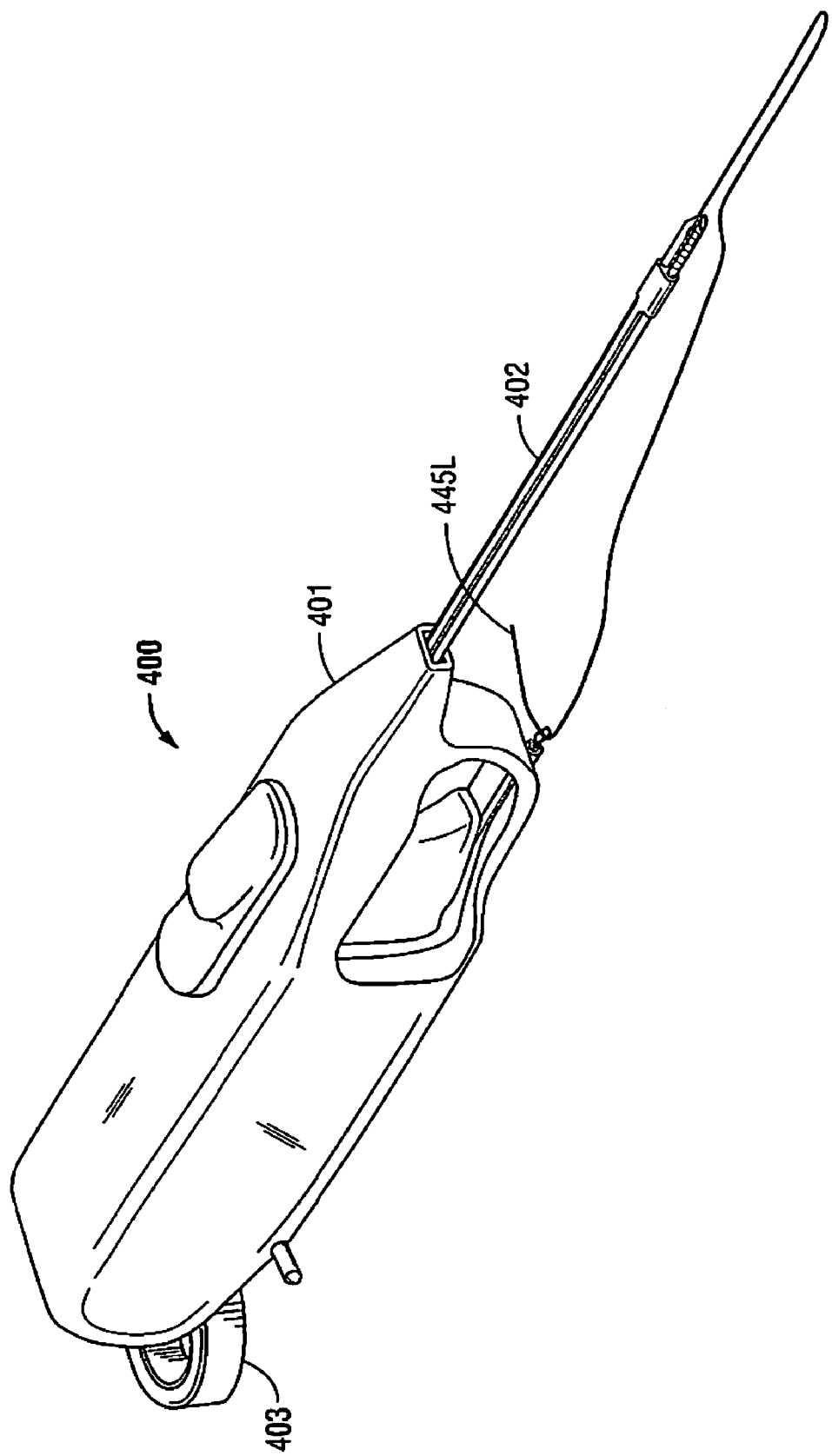
Figure 79:
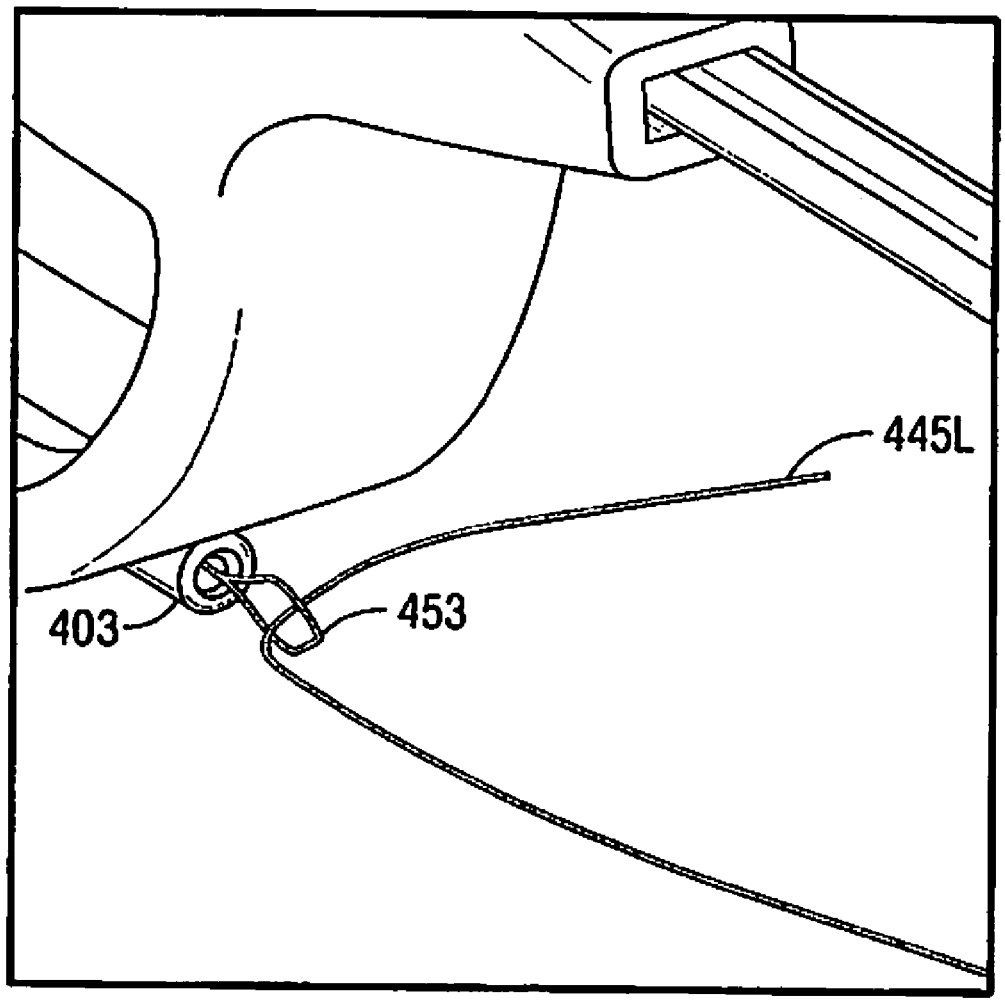
Figure 80:
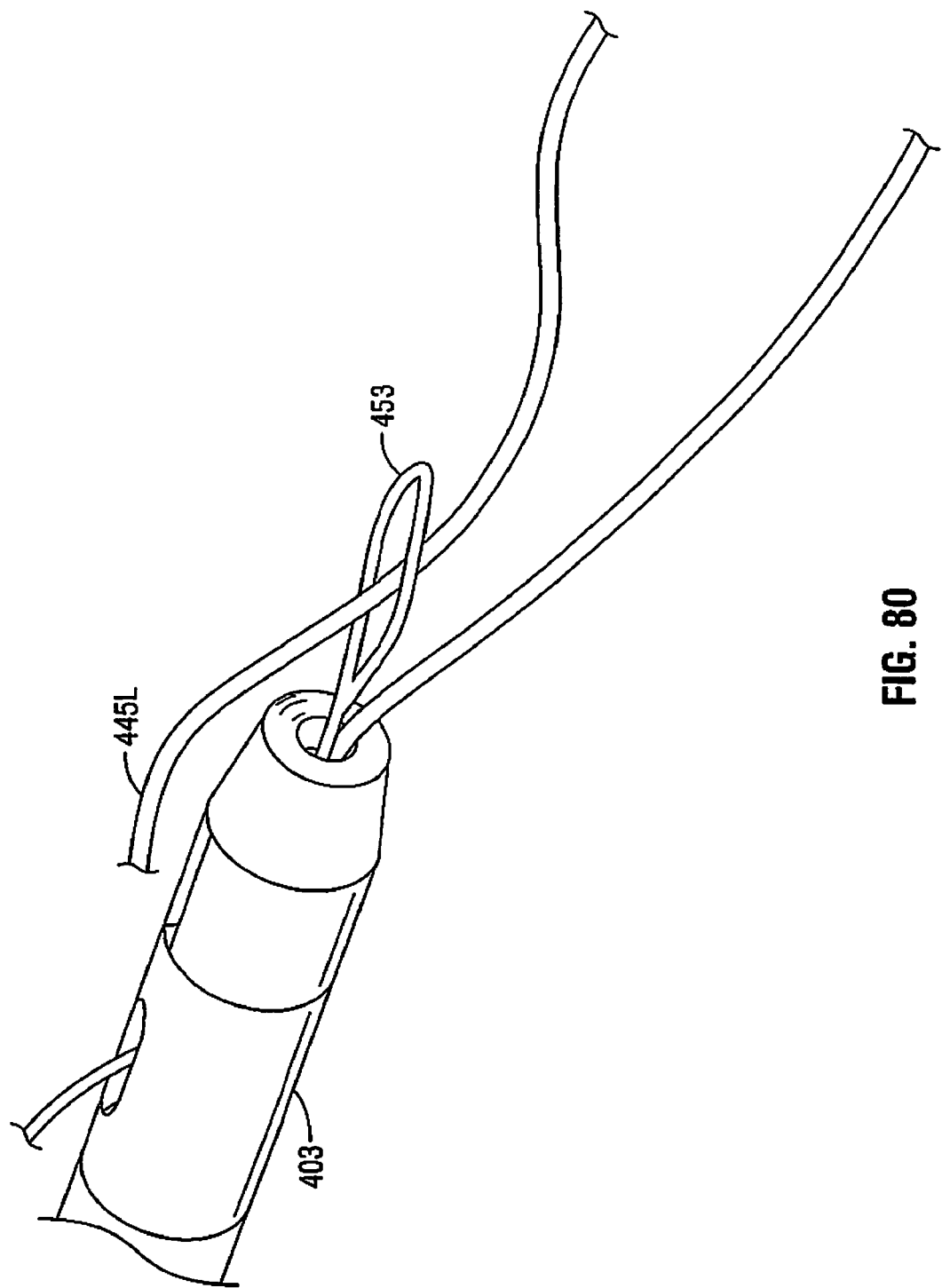
Figure 81:
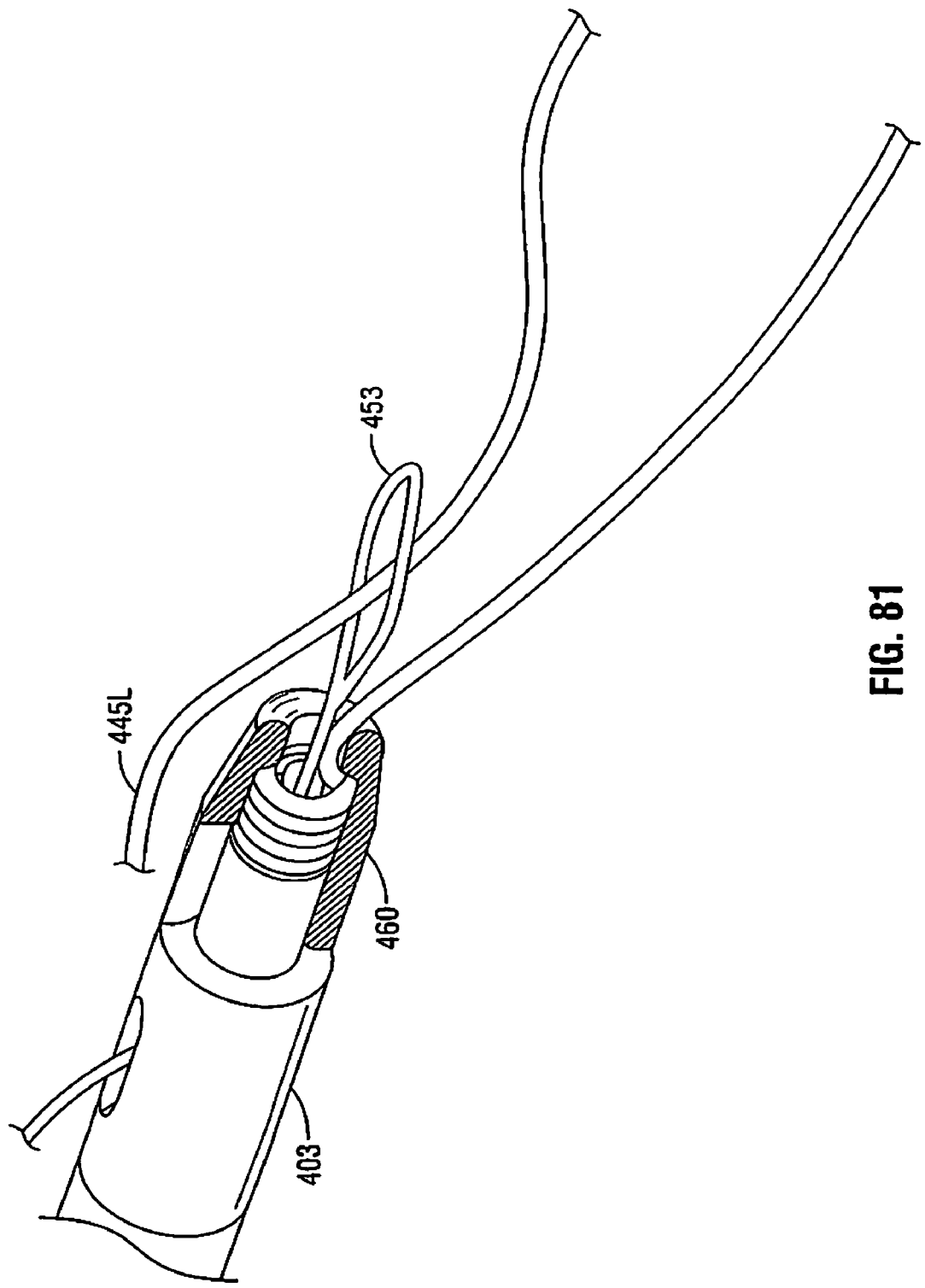
Figure 82:
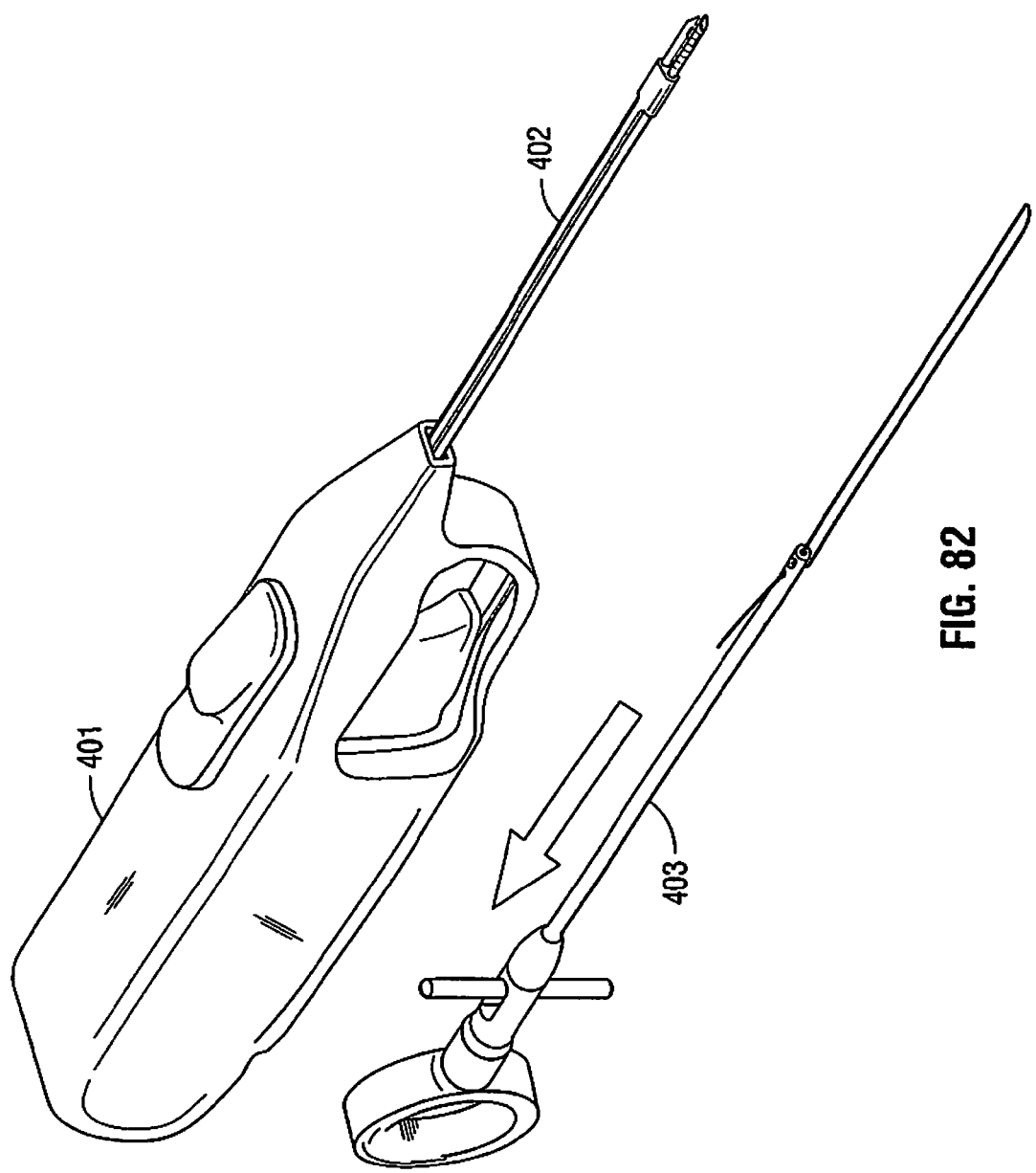
Figure 83:
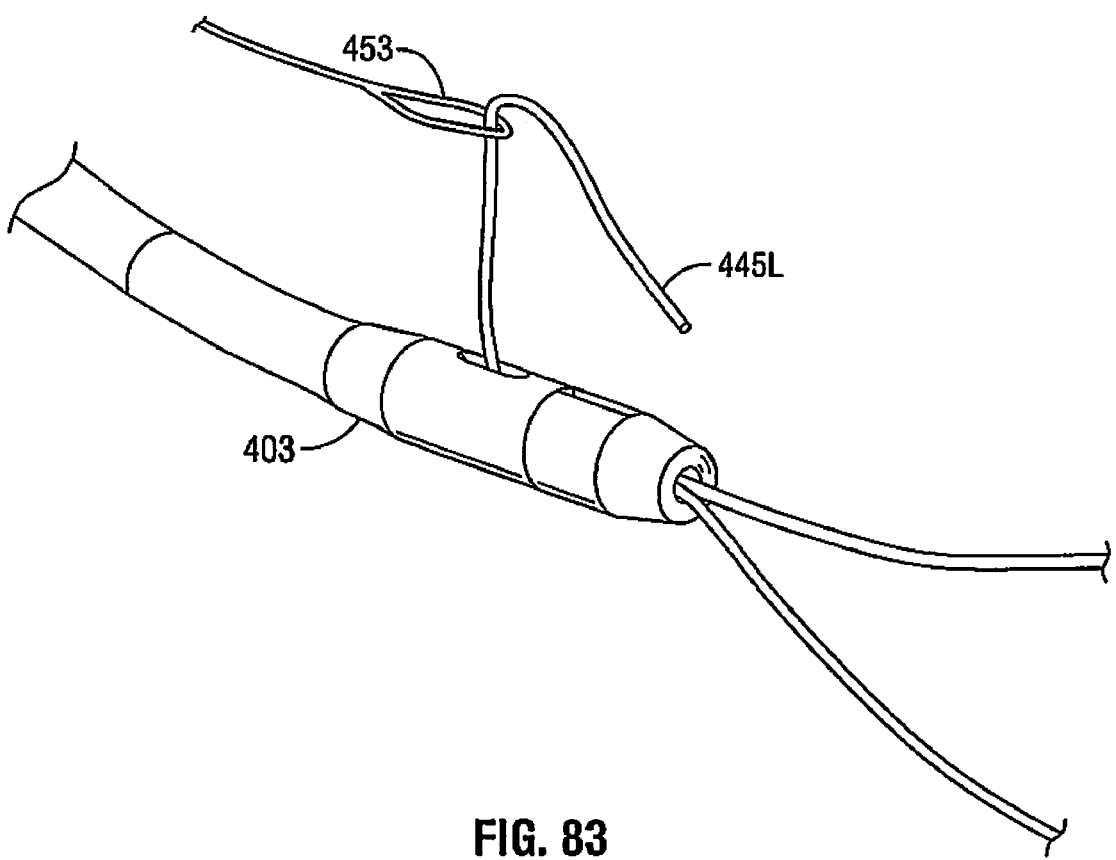
Figure 84:
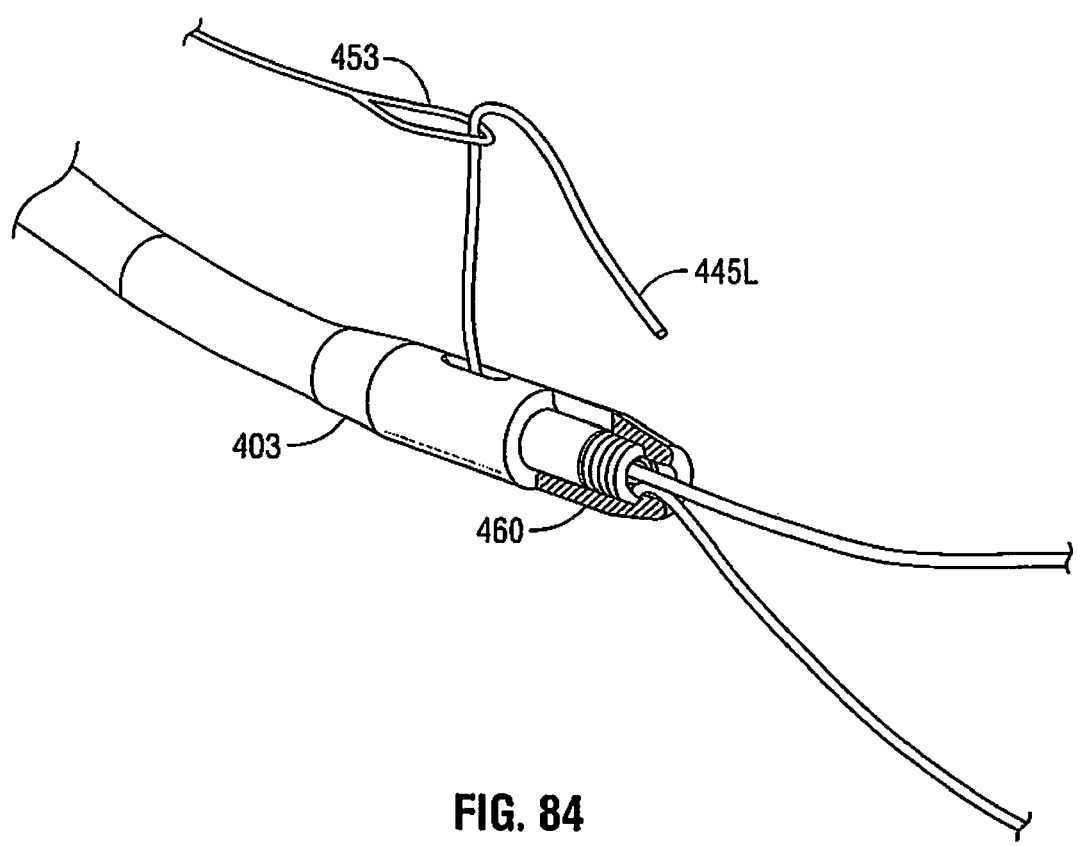

Next, the suture is tied down so as to close the tear in the meniscus. This may be done in a variety of ways which will be apparent to those skilled in the art in view of the present disclosure. In one preferred form of the invention, this is accomplished in the following way. Looking now at FIGS. 76 and 77, pusher/cutter 403 is ready to receive leading portion 445L of suture 445. Then, as shown in FIGS. 78-81, leading portion 445L of suture 445 is inserted into a loop 453 of pusher/cutter 403. Again, loop 453 of pusher/cutter 403 essentially comprises a conventional suture threader component, or needle threader component, in the sense that a collapsible loop is formed at the end of a pullable shaft. Then pusher/cutter 403 is detached from handle 401, carrying leading portion 445L of suture 445. Next, leading portion 445L of suture 445 is passed through a pre-formed, uncinched knot 460 disposed at the tip of pusher/cutter 403 (FIGS. 82-84). It will be appreciated that as leading portion 445L of suture 445 is passed through pre-formed, uncinched knot 460, the suture passes back through itself.

Figure 85:
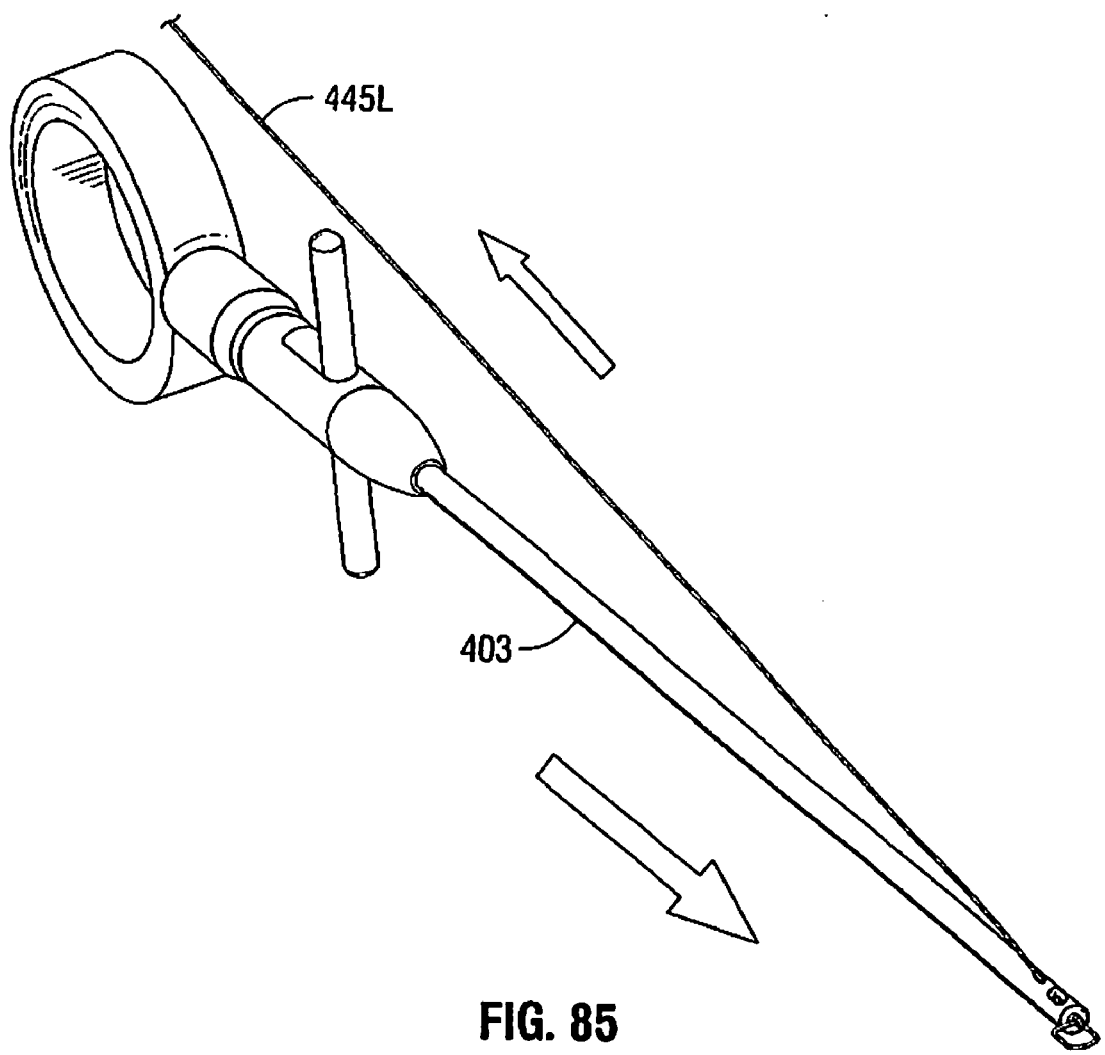
Figure 86:
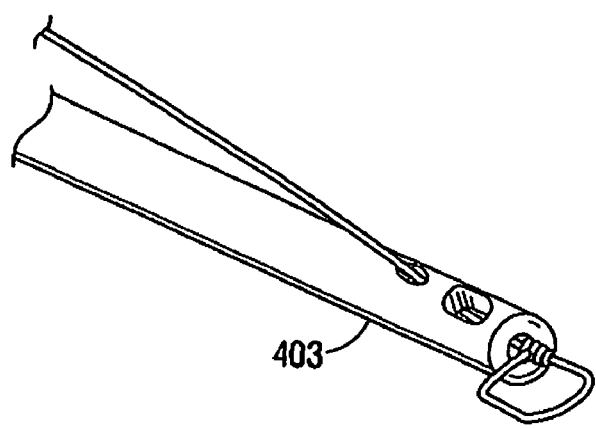
Figure 87:
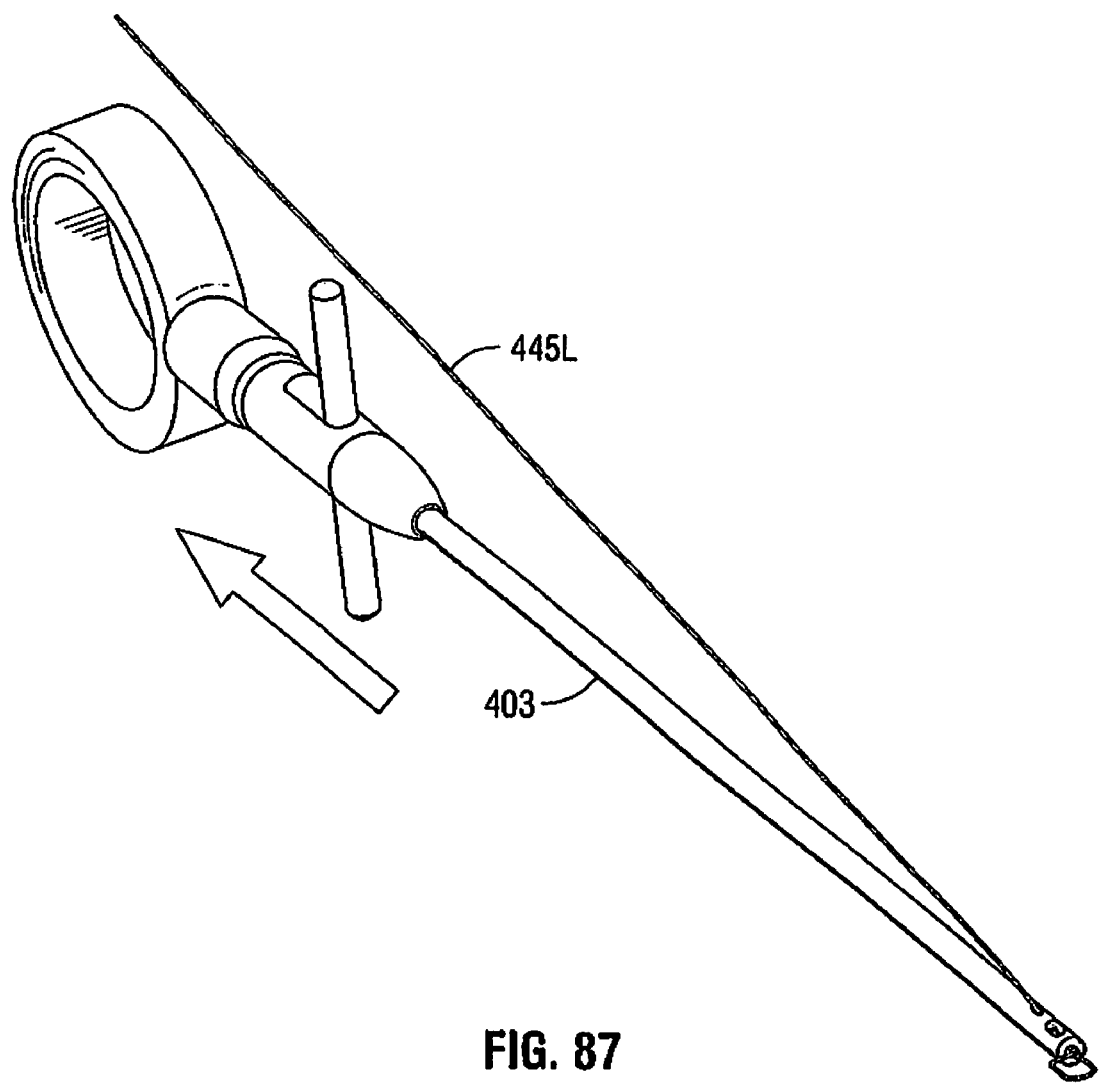
Figure 88:
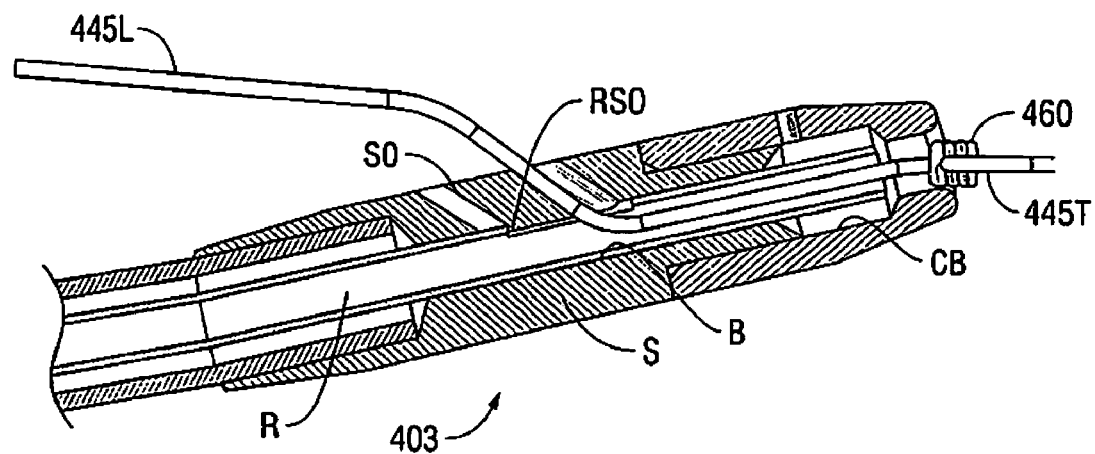
Figure 89:
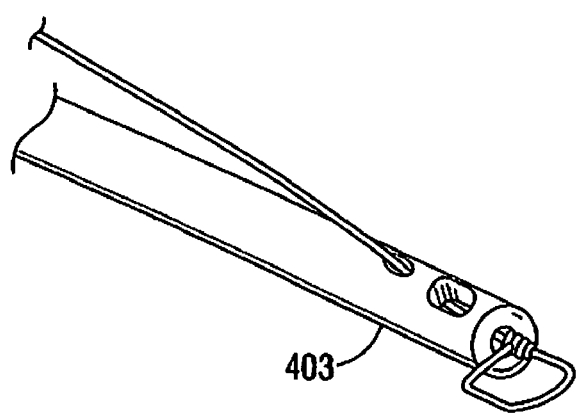
Figure 90:
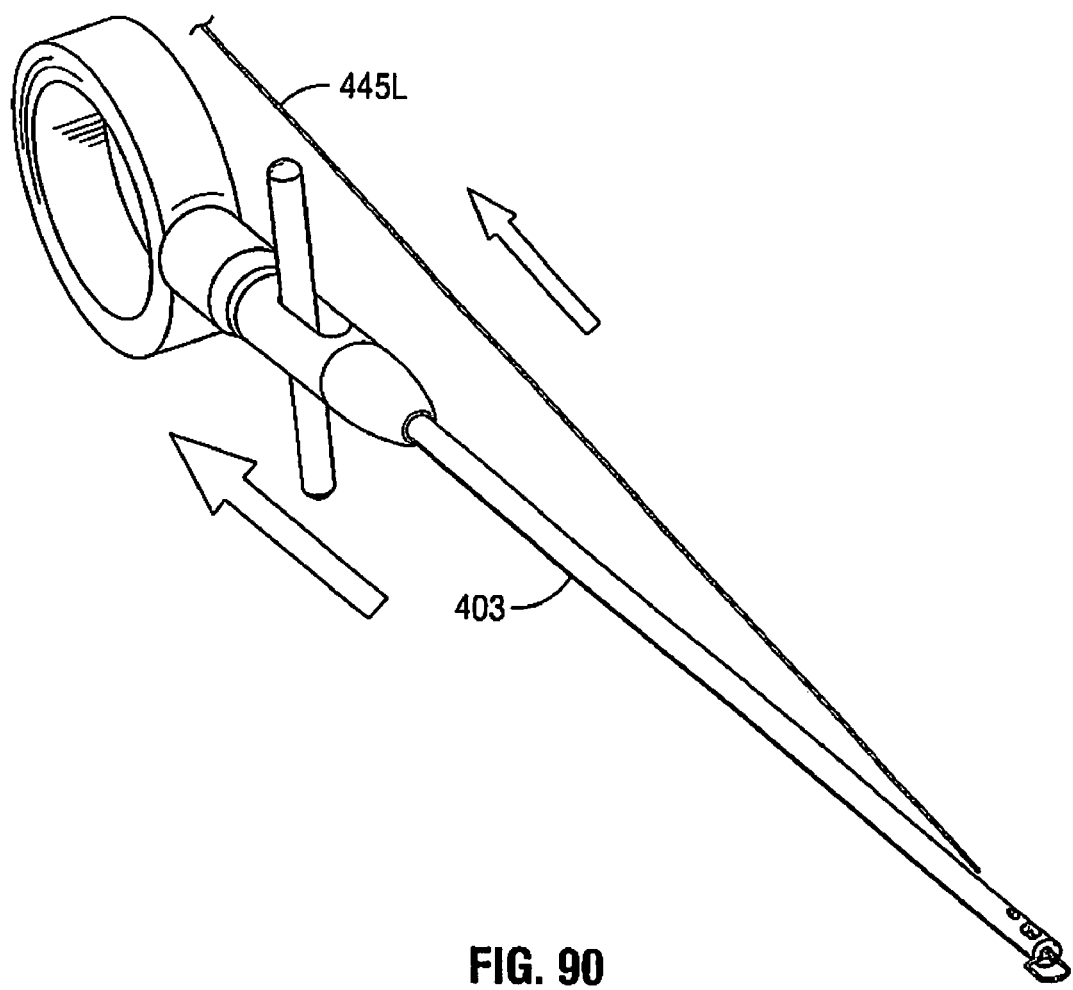
Figure 91:
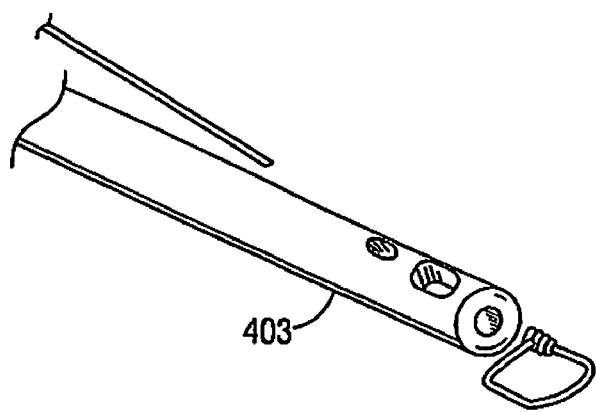
Figure 92:
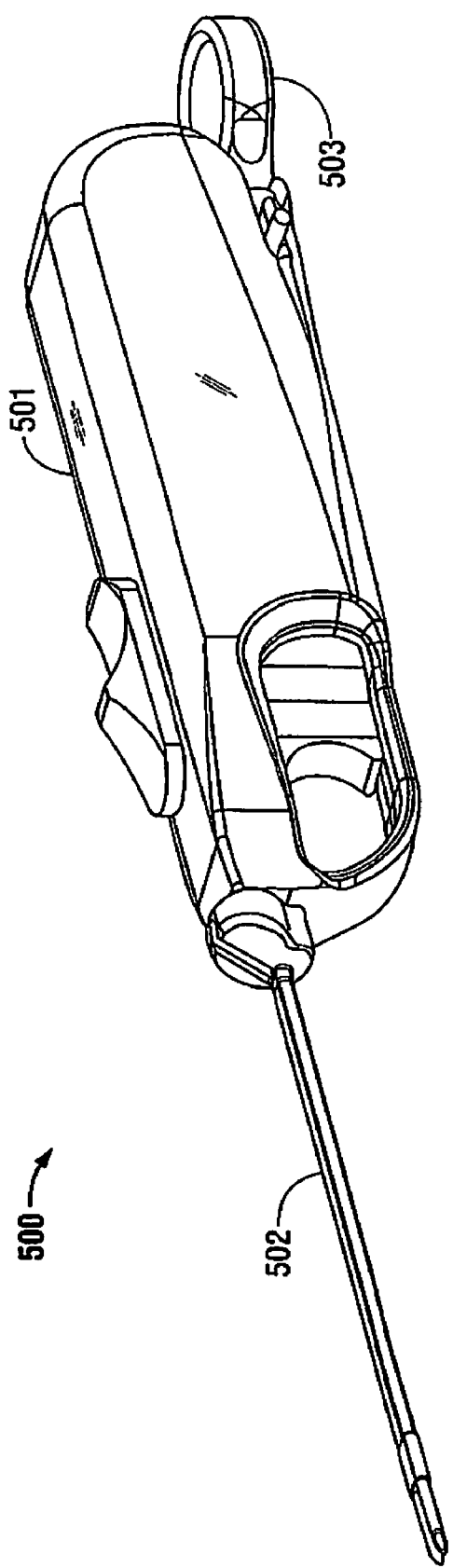
Figure 93:
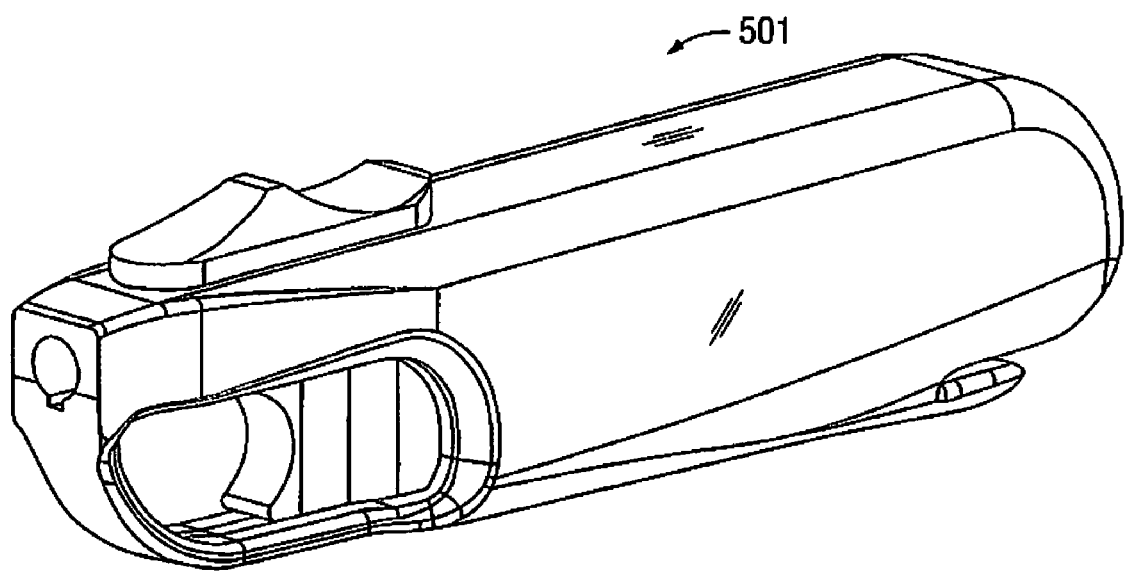
Figure 94:
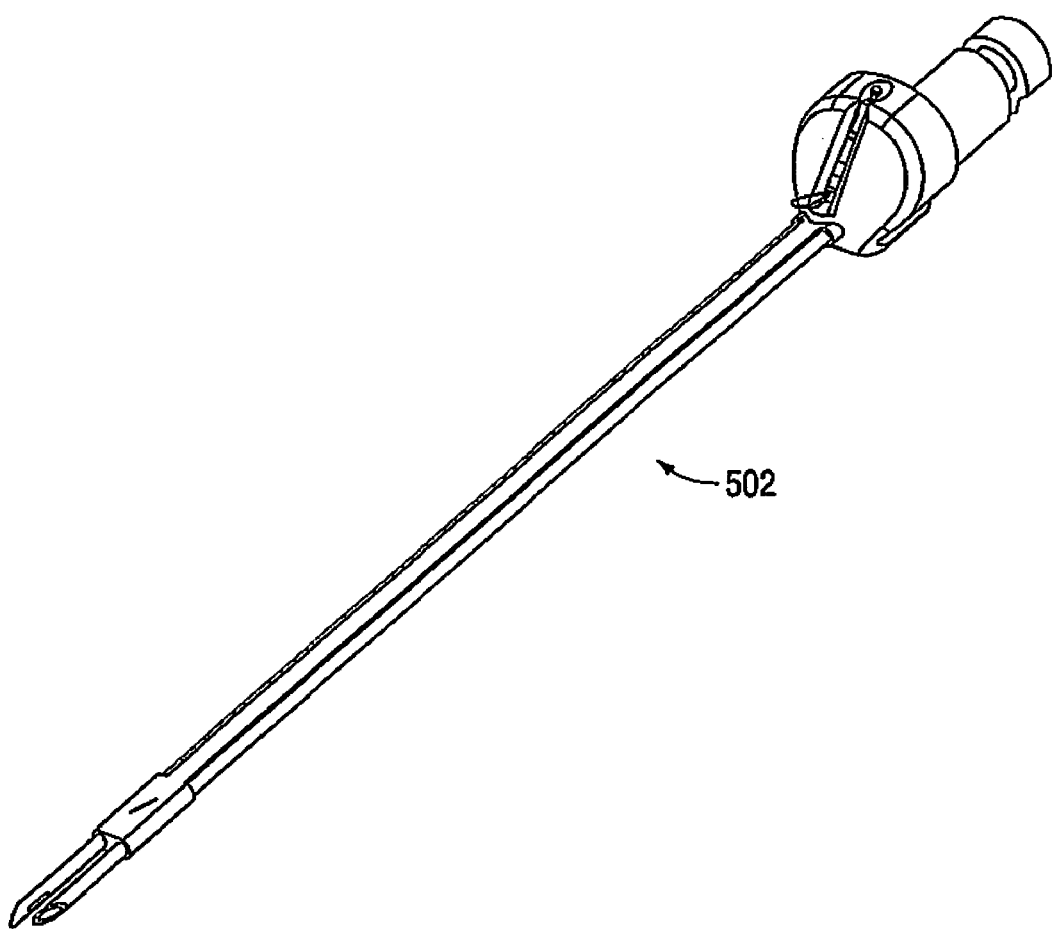
Figure 95:
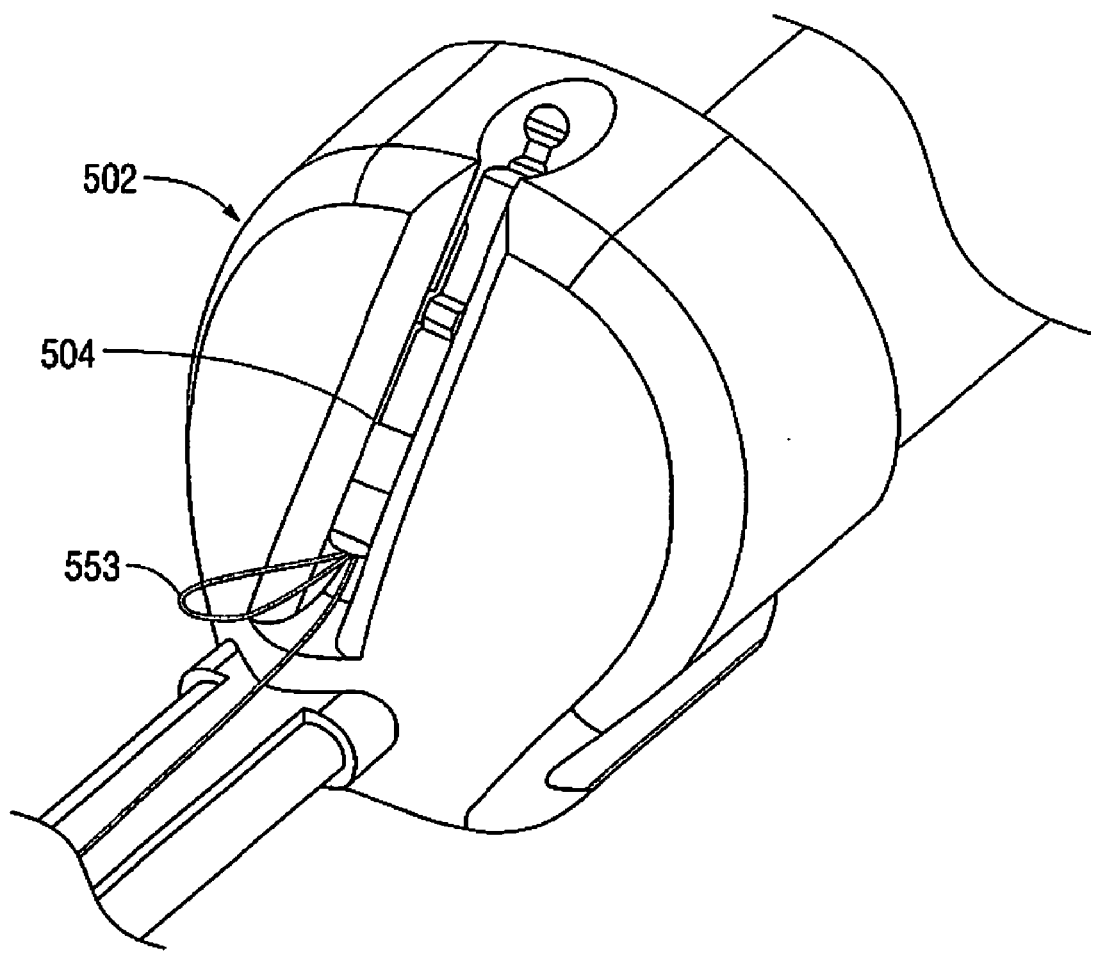
Figure 96:
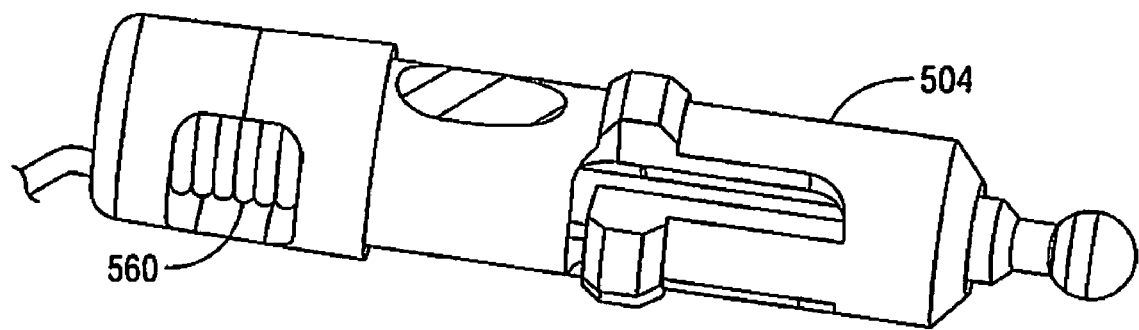
Figure 97:
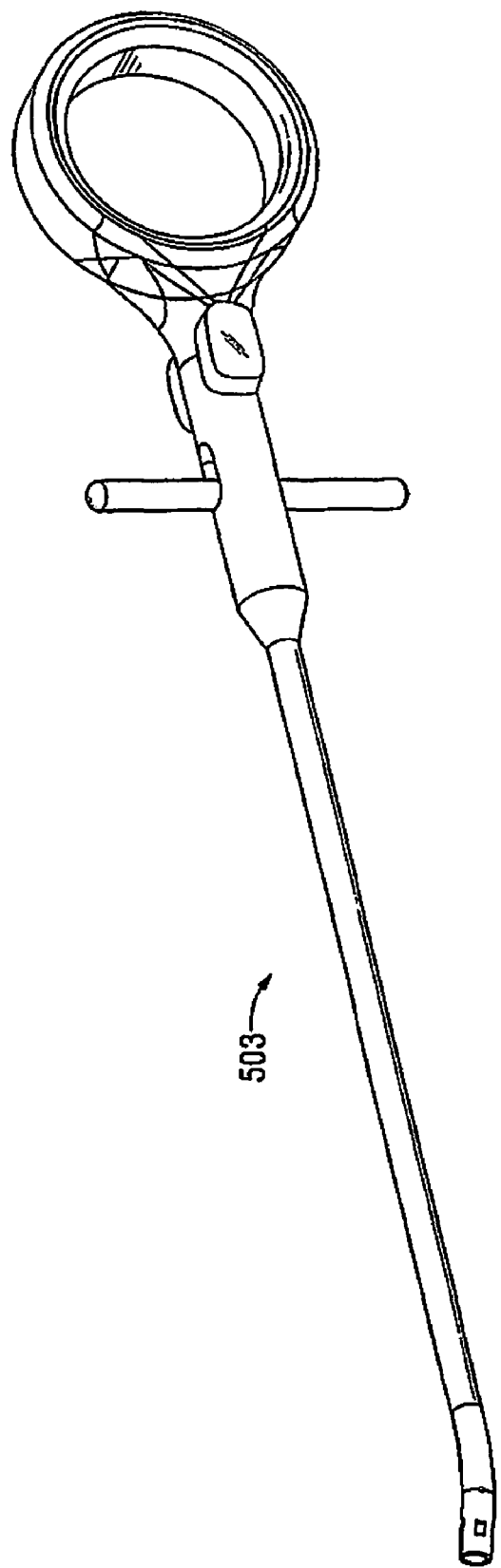

Then, and looking now at FIGS. 85 and 86, pusher/cutter 403 is advanced distally so as to bring pre-formed, un-cinched knot 460 to the near side surface of the meniscus. Next, as shown in FIGS. 87-89, the pre-formed knot is tightened. Then leading portion 445L of suture 445 is trimmed away by pusher/cutter 403 (FIGS. 90 and 91). Finally, pusher/cutter 403 is removed, leaving suture 445 closing the tear in the meniscus with a low-profile suture fixation.

In one preferred form of the invention, and looking now at FIG. 88, pusher/cutter 403 comprises a shaft S having a central bore B, a counterbore CB and a side opening SO. A hollow ram R, having a ram side opening RSO, is slidably disposed within bore B of shaft S. Prior to knot deployment, the pre-formed, uncinched knot 460 is seated within counterbore CB; and after leading portion 445L of suture 445 is passed through pre-formed, uncinched knot 460, leading portion 445L is drawn through ram side opening RSO and shaft side opening SO; and when the knot is to be separated from shaft S, ram R is moved distally, first pushing the knot out of the shaft and, after cinching, thereafter cutting leading portion 445L of suture 445 by virtue of moving side opening SO out of alignment with ram side opening RSO.

In one preferred form of the invention, the cinched knot is separated from shaft S in a first discrete step, and then the suture is cut in a second discrete step.

Fifth Preferred Method and Apparatus

In yet another preferred form of the present invention, the pre-formed, uncinched knot can be stored in a disposable tip that is releasably mounted to the needles, with the needles themselves being releasably mounted to the handle, and with the disposable tip being connectable to a pusher after the suture has been passed through the tissue. This construction has the advantage that (i) a single handle can be used for both the needles and pusher, and (ii) a single handle and a single pusher can be provided even where a patient may require multiple stitches (i.e., multiple disposable tips with multiple pre-formed, uncinched knots).

More particularly, and looking now at FIGS. 92-97, there is shown an apparatus 500 for use in closing tear 20 in meniscus 5. Apparatus 500 generally comprises a handle 501, a needle cartridge 502, and a pusher 503. Needle cartridge 502 includes a disposable tip 504 which contains the pre-formed, uncinched knot 560. Specific details of the construction and function of handle 501, needle cartridge 502, pusher 503 and disposable tip 504 will be disclosed in the course of the following discussion of using apparatus 500 to close tear 20 in meniscus 5.

The apparatus 500 is prepared for use by mounting needle cartridge 502 mounted to handle 501, and mounting pusher 503 to handle 501 (FIG. 98).

Figure 99:
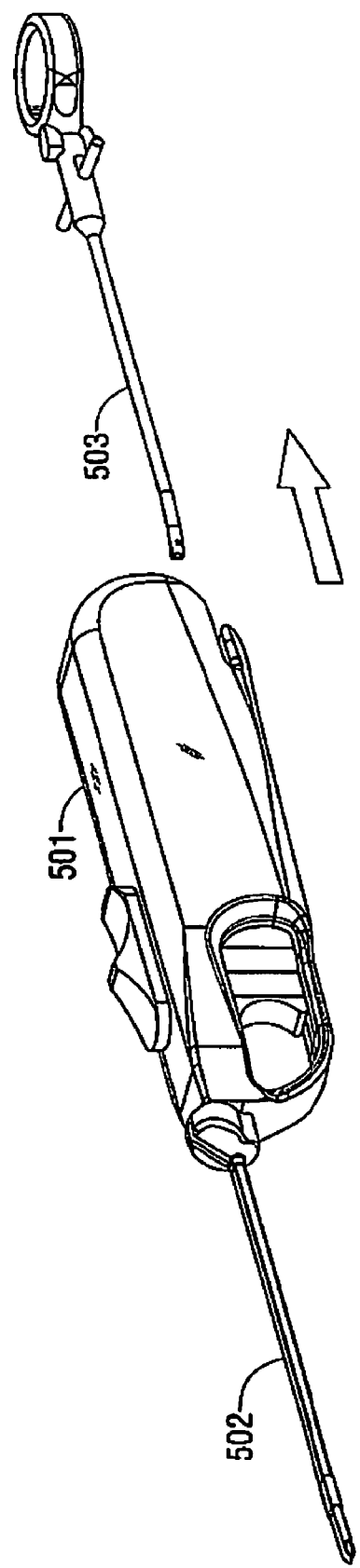
Figure 100:
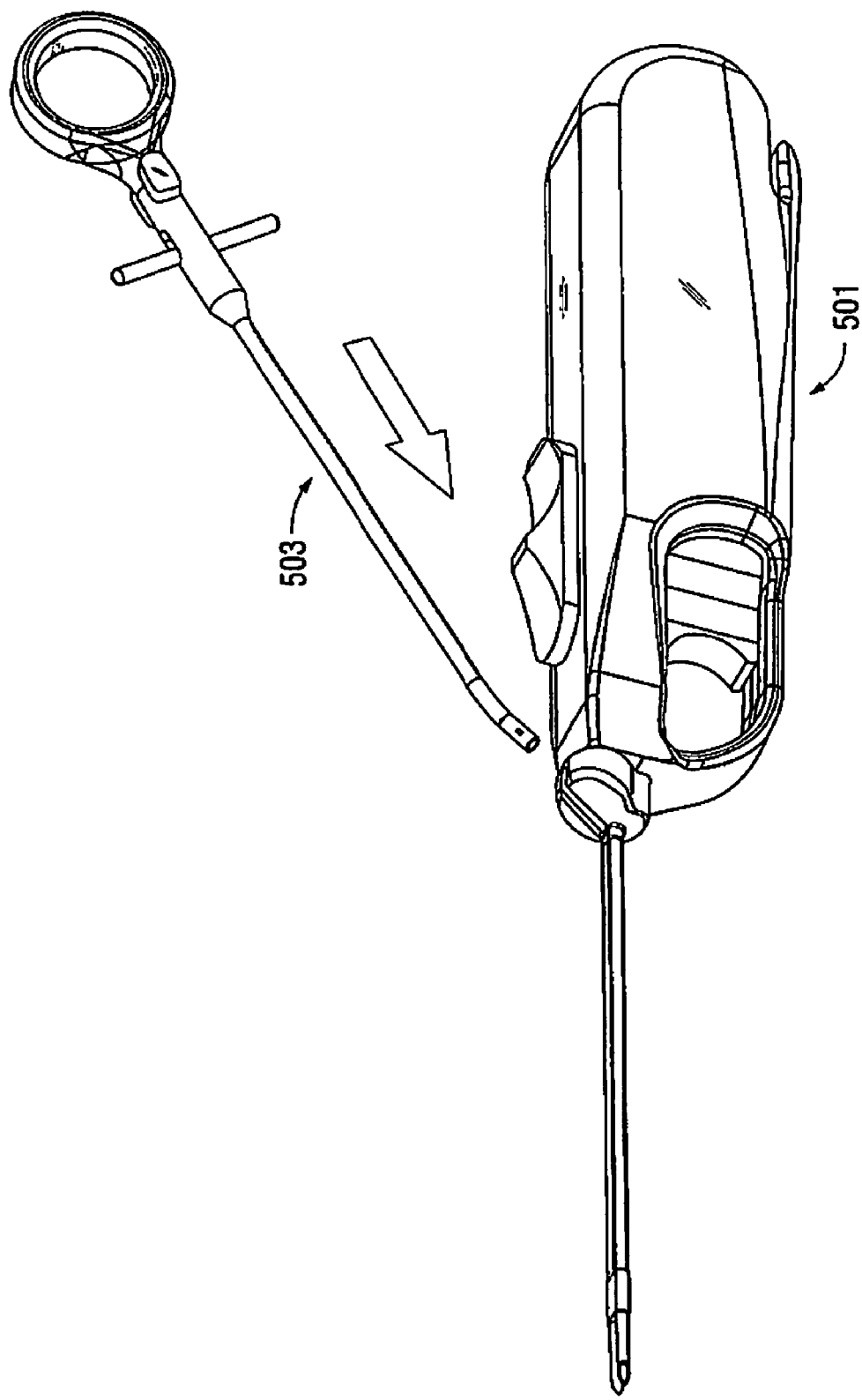
Figure 101:
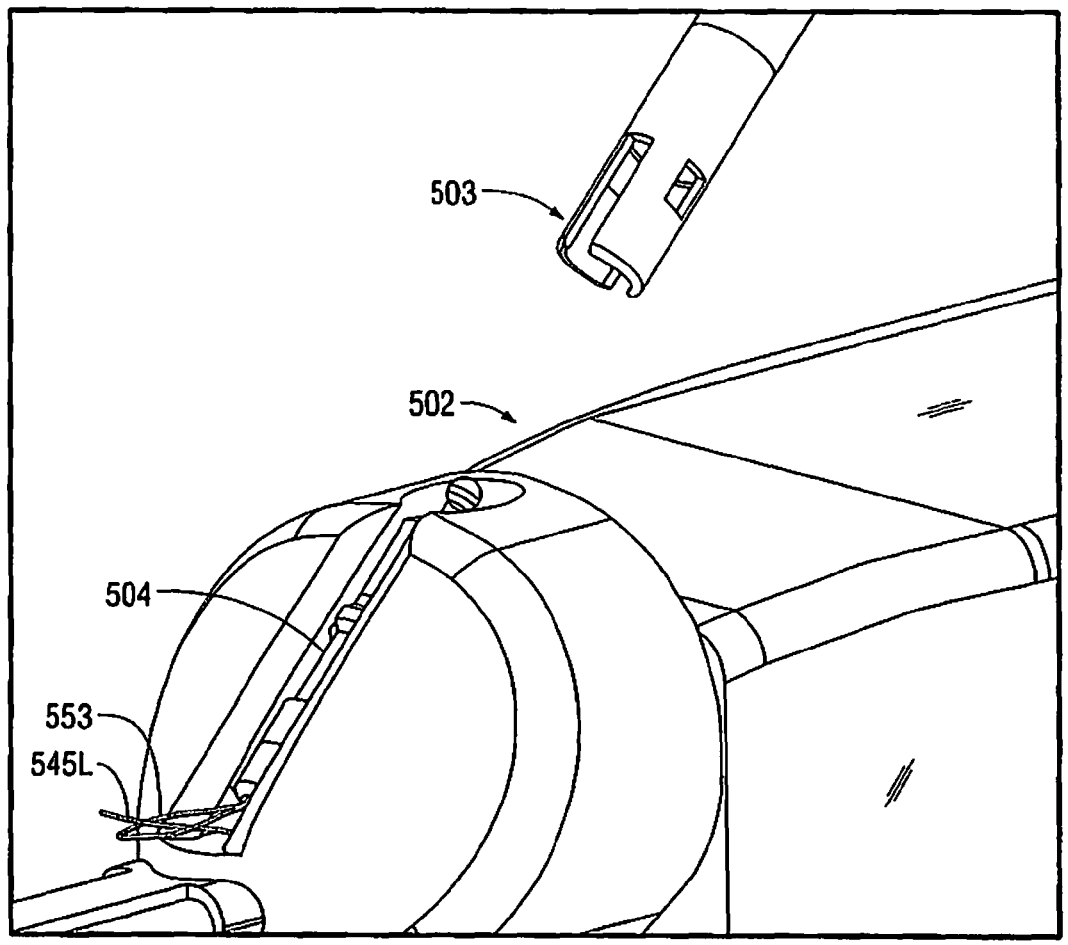
Figure 102:
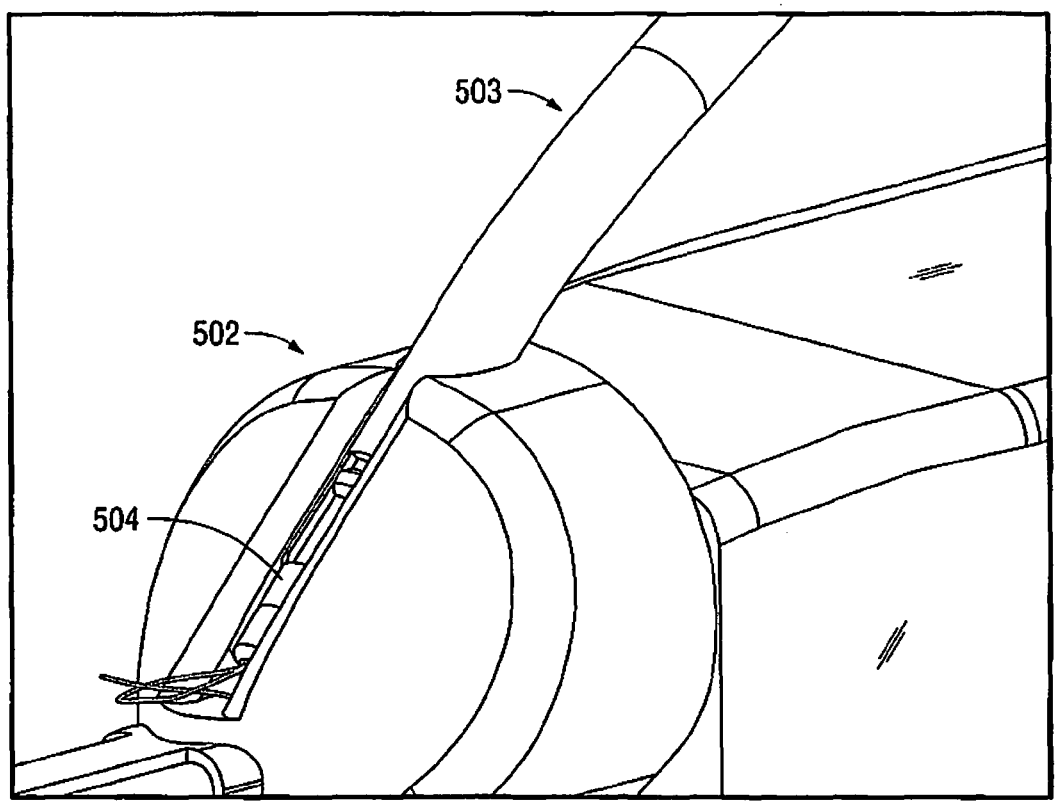
Figure 103:
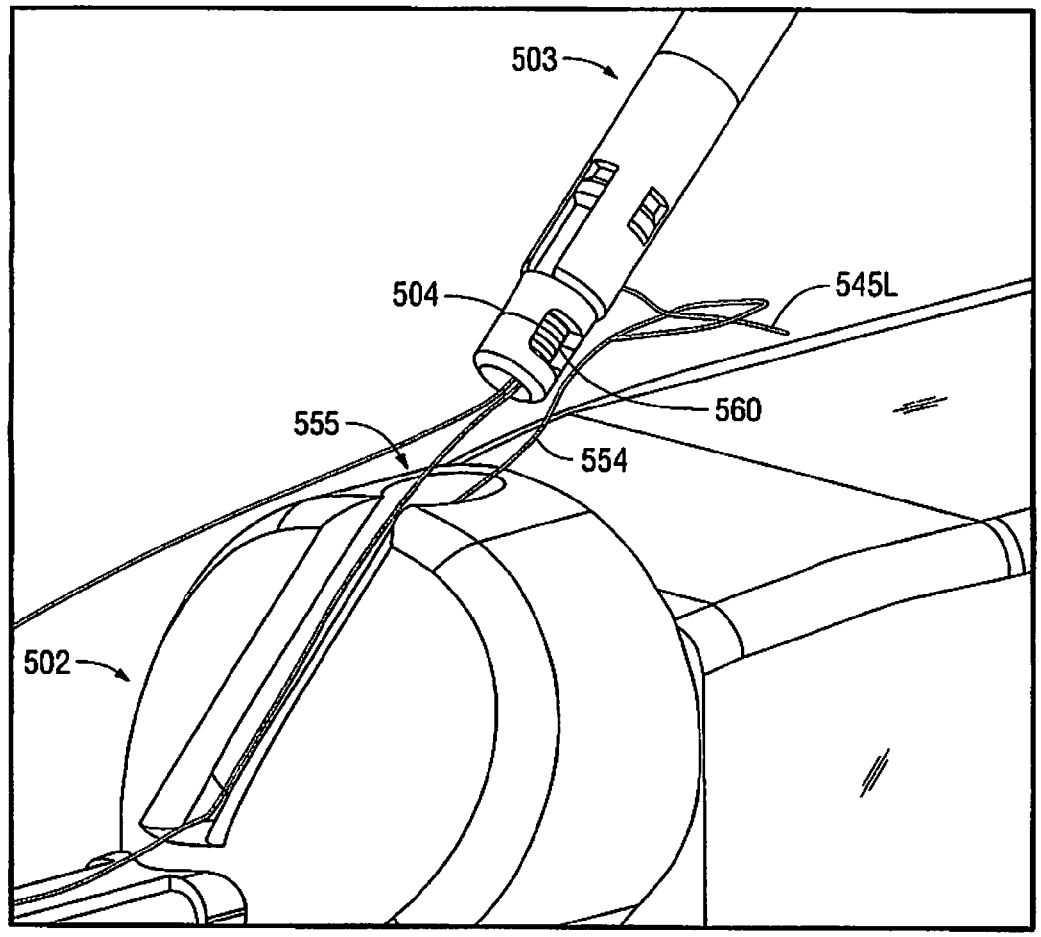

Apparatus 500 utilizes the same suture passing approach as apparatus 400 in order to pass and retract the leading portion of the suture from the near side of the meniscus to the far side of the meniscus and then back. Once the leading portion 545L of suture 545 is retracted to the near side of the meniscus, leading portion 545L of suture 545 is threaded into loop 553 of a snare 554. Snare 554 in turn extends through the body of disposable tip 504, including through pre-formed, uncinched knot 560, and exits disposable tip 504 before being attached to needle cartridge 502 at 555. Then, pusher 503 is detached from handle 501 (FIG. 99) and is brought down into engagement with disposable tip 504 (FIGS. 100-102). Pusher 503 is then withdrawn, carrying disposable tip 504 with it. As disposable tip 504 is withdrawn from needle cartridge 502, snare 554 is pulled back through the retreating disposable tip 504 thereby threading suture 545L through pre-formed, uncinched knot 560. Thereafter, suture 545 is secured in the manner previously discussed.

Additional Aspects of the Invention

It will be appreciated that needles 105, 115, 205, 215, 305, 315, 405, 415, etc. may be straight (as shown) or curved as desired.

Furthermore, the apparatus 100, 200, 300, 400, 500 may be used with either a medial or lateral approach.

Modifications

It is to be understood that the present invention is by no means limited to the particular constructions herein disclosed and/or shown in the drawings, but also comprises any modifications or equivalents within the scope of the invention.

What is claimed is:

1. Apparatus for suturing tissue, wherein the apparatus comprises:
   a housing;
   a first needle mounted to the housing;
   a second needle mounted to the housing, the second needle defining a slot that extends completely through the second needle, the slot being positioned such that a distalmost end of the slot is positioned proximal to a distalmost end of the second needle;
   a suture having a leading portion and a trailing portion, the leading portion mounted to the first needle when the leading portion is in an initial position;
   a first structure associated with the first needle for passing the leading portion of the suture from the first needle to the second needle after the first needle, with the leading portion of the suture mounted thereto, has been positioned within the tissue; and
   a second structure associated with the second needle, the second structure configured to retain the leading portion of the suture within the slot such that, when the apparatus is removed from the tissue, the leading portion of the suture is carried by the second needle out of the tissue.

2. Apparatus according to claim 1 wherein the first structure comprises a suture holder extendable out of the first needle and comprising a suture engager formed at the end of an angled shaft.

3. Apparatus according to claim 1 wherein the apparatus further comprises a pre-formed, uncinched knot formed in the trailing portion of the suture.

4. Apparatus according to claim 3 wherein the pre-formed, uncinched knot is supported relative to the housing on the near side of the tissue.

5. Apparatus according to claim 3 wherein the pre-formed, uncinched knot is supported about the exterior of the second needle.

6. Apparatus according to claim 3 wherein the apparatus further comprises a support, and wherein the pre-formed, uncinched knot is releasably supported on the support on the near side of the tissue.

7. Apparatus according to claim 6 wherein the support is releasably mounted to the housing.

8. Apparatus according to claim 6 wherein the apparatus further comprises a suture threader movably mounted to the support, wherein the suture threader is configured to selectively pass the leading portion of the suture through the pre-formed. uncinched knot.

9. Apparatus according to claim 8 wherein the suture threader comprises a collapsible loop.

10. Apparatus according to claim 6 wherein the support further comprises a shaft for pushing the pre-formed, uncinched knot off the support.

11. Apparatus according to claim 10 wherein the support further comprises cutting structure for cutting the suture after the pre-formed, uncinched knot is pushed off the support.

12. Apparatus according to claim 11 wherein the cutting structure is configured to cut the suture after the pre-formed, uncinched knot is cinched.

13. Apparatus according to claim 11 wherein the cutting structure comprises an opening in the support and an opening in the shaft, and wherein cutting is effected when the opening in the support and the opening in the shaft are moved out of alignment with one another.

* * * * *

UNITED STATES PATENT AND TRADEMARK OFFICE
CERTIFICATE OF CORRECTION

PATENT NO. : 7,918,868 B2
APPLICATION NO. : 11/805223
DATED : April 5, 2011
INVENTOR(S) : Peter Marshall et al.

Page 1 of 1

It is certified that error appears in the above-identified patent and that said Letters Patent is hereby corrected as shown below:

The Title page of U.S. Patent 7,918,868 incorrectly shows the Assignee's name as: Scandius Biomendical, Inc.

The correct spelling of the Assignee's name is: Scandius Biomedical, Inc.

Signed and Sealed this
Twenty-third Day of August, 2011

David J. Kappos
*Director of the United States Patent and Trademark Office*